(12) United States Patent
Masuyama et al.

(10) Patent No.: US 8,426,106 B2
(45) Date of Patent: Apr. 23, 2013

(54) PHOTORESIST COMPOSITION

(75) Inventors: Tatsuro Masuyama, Toyonaka (JP);
Kazuhiko Hashimoto, Toyonaka (JP);
Junji Shigematsu, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 198 days.

(21) Appl. No.: 12/903,146

(22) Filed: Oct. 12, 2010

(65) Prior Publication Data
US 2011/0091807 A1 Apr. 21, 2011

(30) Foreign Application Priority Data

Oct. 15, 2009 (JP) ................. 2009-238052

(51) Int. Cl.
*G03F 7/039* (2006.01)
*G03F 7/20* (2006.01)
*G03F 7/30* (2006.01)
*G03F 7/38* (2006.01)

(52) U.S. Cl.
USPC ........ 430/270.1; 430/311; 430/326; 430/330; 430/910; 430/921; 430/925; 560/221; 560/222; 560/223; 560/193; 560/196; 560/197; 526/245; 526/248; 526/292.2; 526/292.4; 526/292.5; 526/323.1; 526/326; 526/328

(58) Field of Classification Search ............. None
See application file for complete search history.

(56) References Cited

U.S. PATENT DOCUMENTS

| 5,015,559 | A | 5/1991 | Ogawa |
| 5,965,325 | A | 10/1999 | Matsuo et al. |
| 2008/0057436 | A1 | 3/2008 | Kim et al. |
| 2008/0166660 | A1 | 7/2008 | Takata et al. |

FOREIGN PATENT DOCUMENTS

| JP | 06-295063 A | 10/1994 |
| JP | 2001-305735 A | 2/2001 |

OTHER PUBLICATIONS

Richter et al "Negative Tone Resist for Phase-Shifting Mask Technology: A Progress Report", Proceedings of SPIE, vol. 3999 (2000), p. 91-101.*

* cited by examiner

*Primary Examiner* — Sin J. Lee
(74) *Attorney, Agent, or Firm* — Hogan Lovells US LLP

(57) ABSTRACT

A Photoresist composition comprising a polymer comprising a structural unit derived from a compound represented by the formula (I):

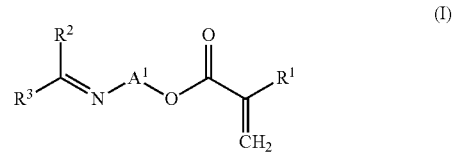

wherein $R^1$ represents a hydrogen atom or a methyl group, $R^2$ represents a C6-C12 aromatic hydrocarbon group which can have one or more substituents, $R^3$ represents a cyano group or a C1-C12 hydrocarbon group which can have one or more substituents and which can contain one or more heteroatoms, $A^1$ represents a single bond, $-(CH_2)_g-CO-O-*$ or $-(CH_2)_h-O-CO-(CH_2)_i-CO-O-*$ wherein g, h and i each independently represent an integer of −1 to 6 and * represents a binding position to the nitrogen atom, a resin having an acid-labile group and being insoluble or poorly soluble in an aqueous alkali solution but becoming soluble in an aqueous alkali solution by the action of an acid, and an acid generator.

12 Claims, No Drawings

PHOTORESIST COMPOSITION

This nonprovisional application claims priority under 35 U.S.C. §119(a) on Patent Application No. 2009-238052 filed in JAPAN on Oct. 15, 2009, the entire contents of which are hereby incorporated by reference.

FIELD OF THE INVENTION

The present invention relates to a photoresist composition.

BACKGROUND OF THE INVENTION

A photoresist composition is used for semiconductor microfabrication employing a lithography process.

US 2008/0166660 A1 discloses a photoresist composition comprising a resin having a structural unit derived from 2-ethyl-2-adamantyl methacrylate, a structural unit derived from 3-hydroxy-1-adamantyl methacrylate, a structural unit derived from 2-(5-oxo-4-oxatricyclo[4.2.1.0$^{3,7}$]nonan-2-yloxy)-2-oxoethyl methacrylate and a structural unit derived from α-methacryloyloxy-γ-butyrolactone, an acid generator comprising triphenylsulfonium 4-oxoadamantan-1-yloxy-carbonyl(difluoro)methanesulfonate, a basic compound comprising 2,6-diisopropylaniline and solvents.

SUMMARY OF THE INVENTION

The present invention is to provide a photoresist composition.

The present invention relates to the followings:

<1> A photoresist composition comprising a polymer comprising a structural unit derived from a compound represented by the formula (I):

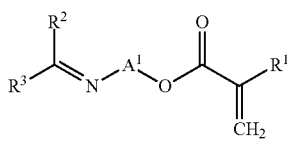

wherein $R^1$ represents a hydrogen atom or a methyl group, $R^2$ represents a C6-C12 aromatic hydrocarbon group which can have one or more substituents, $R^3$ represents a cyano group or a C1-C12 hydrocarbon group which can have one or more substituents and which can contain one or more heteroatoms, $A^1$ represents a single bond, —(CH$_2$)$_g$—CO—O—* or —(CH$_2$)$_h$—O—CO—(CH$_2$)$_i$—CO—O—* wherein g, h and i each independently represent an integer of 1 to 6 and * represents a binding position to the nitrogen atom, a resin having an acid-labile group and being insoluble or poorly soluble in an aqueous alkali solution but becoming soluble in an aqueous alkali solution by the action of an acid, and an acid generator;

<2> The photoresist composition according to <1>, wherein $R^2$ is a phenyl group;

<3> The photoresist composition according to <1> or <2>, wherein the resin comprises a structural unit derived from a monomer having an acid-labile group and at least one structural unit selected from the group consisting of a structural unit derived from an acrylate monomer having a hydroxyl-containing adamantyl group, a structural unit derived from a methacrylate monomer having a hydroxyl-containing adamantyl group, a structural unit derived from an acrylate monomer having a lactone ring and a structural unit derived from a methacrylate monomer having a lactone ring;

<4> The photoresist composition according to <1>, <2> or <3>, wherein the resin comprises a copolymer obtained by polymerizing at least a (meth)acrylate monomer having a hydroxyl-containing adamantyl group;

<5> The photoresist composition according to any one of <1> to <4>, wherein the resin comprises a copolymer obtained by polymerizing at least a (meth)acrylate monomer having a lactone ring;

<6> The photoresist composition according to any one of <1> to <5>, wherein the acid generator is a salt represented by the formula (B1):

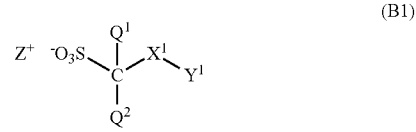

wherein $Q^1$ and $Q^2$ each independently represent a fluorine atom or a C1-C6 perfluoroalkyl group, $X^1$ represents a single bond or a C1-C17 divalent saturated hydrocarbon group in which one or more —CH$_2$— can be replaced by —O— or —CO—, $Y^1$ represents a C1-C36 aliphatic hydrocarbon group which can have one or more substituents, a C3-C36 saturated cyclic hydrocarbon group which can have one or more substituents, or a C6-C36 aromatic hydrocarbon group which can have one or more substituents, and one or more —CH$_2$— in the aliphatic hydrocarbon group and the saturated cyclic hydrocarbon group can be replaced by —O— or —CO—, and $Z^+$ represents an organic counter cation;

<7> A process for producing a photoresist pattern comprising the following steps (1) to (5):

(1) a step of applying the photoresist composition according to any one of <1> to <6> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern;

<8> A compound represented by the formula (I-A):

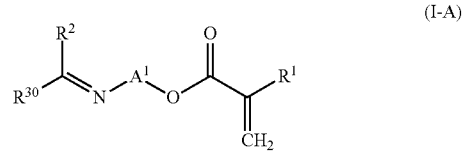

wherein $R^1$ represents a hydrogen atom or a methyl group, $R^2$ represents a C6-C12 aromatic hydrocarbon group which can have one or more substituents, $R^{30}$ represents a C1-C4 fluorinated alkyl group, $A^1$ represents a single bond, —(CH$_2$)$_g$—CO—O—* or —(CH$_2$)$_h$—O—CO—(CH$_2$)$_i$—CO—O—* wherein g, h and i each independently represent an integer of 1 to 6 and * represents a binding position to the nitrogen atom;

<9> A polymer comprising a structural unit derived from a compound represented by the formula (I-A):

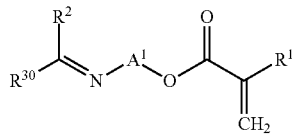

wherein $R^1$ represents a hydrogen atom or a methyl group, $R^2$ represents a C6-C12 aromatic hydrocarbon group which can have one or more substituents, $R^{30}$ represents a C1-C4 fluorinated alkyl group, $A^1$ represents a single bond, $-(CH_2)_g-CO-O-*$ or $-(CH_2)_h-O-CO-(CH_2)_i-CO-O-*$ wherein g, h and i each independently represent an integer of 1 to 6 and * represents a binding position to the nitrogen atom;

<10> A photoresist composition comprising a copolymer comprising a structural unit derived from a compound represented by the formula (I):

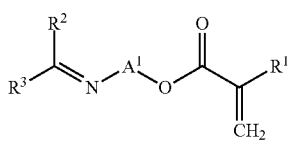

wherein $R^1$ represents a hydrogen atom or a methyl group, $R^2$ represents a C6-C12 aromatic hydrocarbon group which can have one or more substituents, $R^3$ represents a cyano group or a C1-C12 hydrocarbon group which can have one or more substituents and which can contain one or more heteroatoms, $A^1$ represents a single bond, $-(CH_2)_g-CO-O-*$ or $-(CH_2)_h-O-CO-(CH_2)_i-CO-O-*$ wherein g, h and i each independently represent an integer of 1 to 6 and * represents a binding position to the nitrogen atom, and a structural unit having an acid-labile group, and being insoluble or poorly soluble in an aqueous alkali solution but becoming soluble in an aqueous alkali solution by the action of an acid, and an acid generator;

<11> The photoresist composition according to <10>, wherein $R^2$ is a phenyl group;

<12> The photoresist composition according to <10> or <11>, wherein the copolymer further comprises at least one structural unit selected from the group consisting of a structural unit derived from an acrylate monomer having a hydroxyl-containing adamantyl group, a structural unit derived from a methacrylate monomer having a hydroxyl-containing adamantyl group, a structural unit derived from an acrylate monomer having a lactone ring and a structural unit derived from a methacrylate monomer having a lactone ring;

<13> The photoresist composition according to any one of <10> to <12>, wherein the acid generator is a salt represented by the formula (B1):

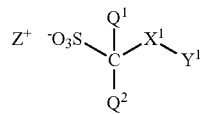

wherein $Q^1$ and $Q^2$ each independently represent a fluorine atom or a C1-C6 perfluoroalkyl group, $X^1$ represents a single bond or a C1-C17 divalent saturated hydrocarbon group in which one or more $-CH_2-$ can be replaced by $-O-$ or $-CO-$, $Y^1$ represents a C1-C36 aliphatic hydrocarbon group which can have one or more substituents, a C3-C36 saturated cyclic hydrocarbon group which can have one or more substituents, or a C6-C36 aromatic hydrocarbon group which can have one or more substituents, and one or more $-CH_2-$ in the aliphatic hydrocarbon group and the saturated cyclic hydrocarbon group can be replaced by $-O-$ or $-CO-$, and $Z^+$ represents an organic counter cation;

<14> A process for producing a photoresist pattern comprising the following steps (1) to (5):

(1) a step of applying the photoresist composition according to any one of <10> to <13> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The first photoresist composition of the present invention comprises a photoresist composition comprising a polymer comprising a structural unit derived from a compound represented by the formula (I):

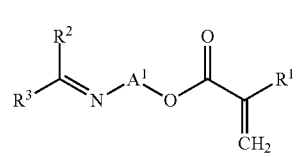

(hereinafter, simply referred to as Compound (I)), a resin having an acid-labile group and being insoluble or poorly soluble in an aqueous alkali solution but becoming soluble in an aqueous alkali solution by the action of an acid (hereinafter, simply referred to as Resin (A)), and an acid generator.

First, Resin (A) will be illustrated.

Resin (A) is insoluble or poorly soluble in an alkali aqueous solution but becomes soluble in an alkali aqueous solution by the action of an acid. Resin (A) has a structural unit derived from a monomer having an acid-labile group, and can be produced by polymerizing one or more monomers having an acid-labile group.

In this specification, "an acid-labile group" means a group capable of being eliminated by the action of an acid.

Examples of the acid-labile group include a group represented by the formula (1):

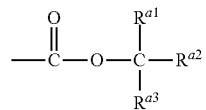

(1)

wherein $R^{a1}$, $R^{a2}$ and $R^{a3}$ independently each represent an aliphatic hydrocarbon group or a saturated cyclic hydrocarbon group, and $R^{a1}$ and $R^{a2}$ can be bonded each other to form a ring together with a carbon atom to which $R^{a1}$ and $R^{a2}$ are bonded.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and preferably has 3 to 20 carbon atoms. Examples of the saturated cyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

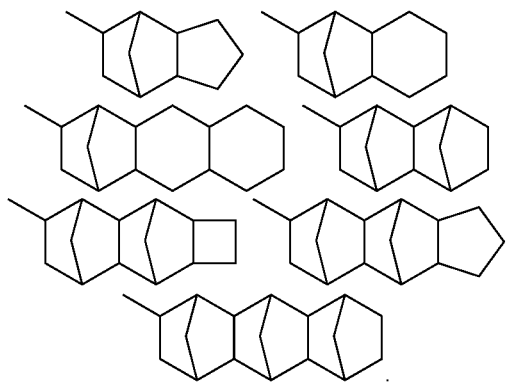

Examples of the ring formed by bonding $R^{a1}$ and $R^{a2}$ each other include the following groups and the ring preferably has 5 to 20 carbon atoms.

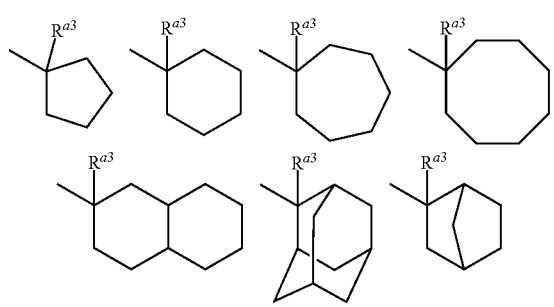

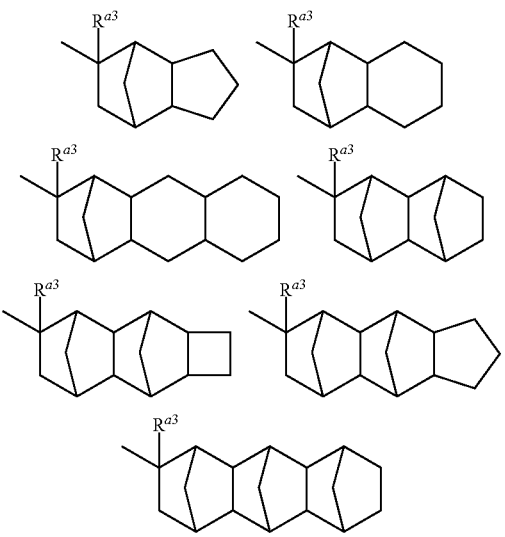

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The monomer having an acid-labile group is preferably an acrylate monomer having an acid-labile group in its side chain or a methacryalte monomer having an acid-labile group in its side chain. In this specification, "(meth)acrylate monomer" means a monomer having a structure represented by $CH_2=CH-CO-$ or $CH_2=C(CH_3)-CO-$, and "acrylate monomer" means a monomer having a structure represented by $CH_2=CH-CO-$, and "methacrylate monomer" means a monomer having a structure represented by $CH_2=C(CH_3)-CO-$.

Preferable examples of the monomer having an acid-labile group include (meth)acrylate monomers having C5-C20 saturated cyclic hydrocarbon group. As (meth)acrylate monomers having C5-C20 saturated cyclic hydrocarbon group, preferred are monomers represented by the formulae (a1-1) and (a1-2):

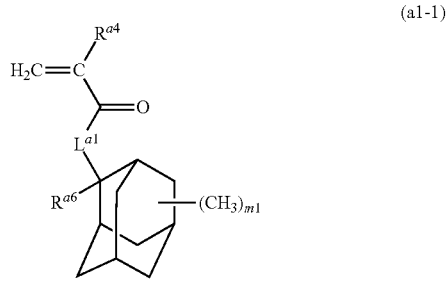

(a1-1)

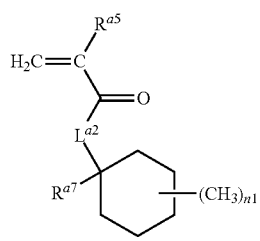

(a1-2)

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 saturated cyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

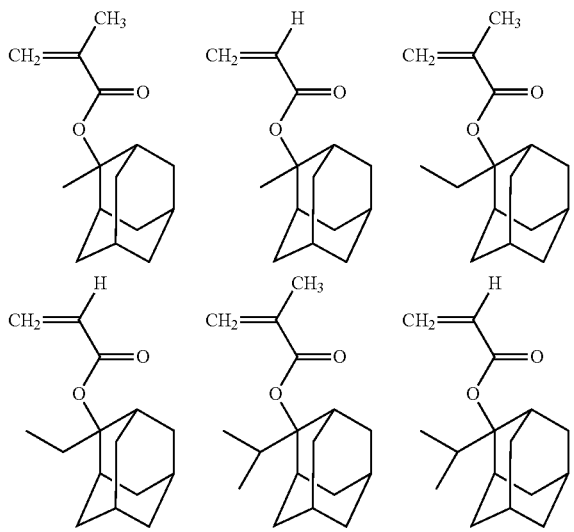

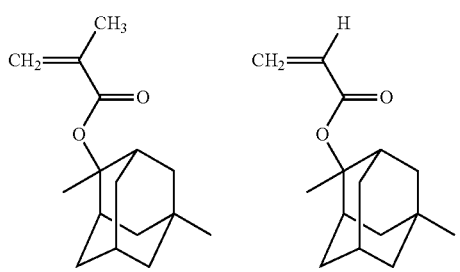

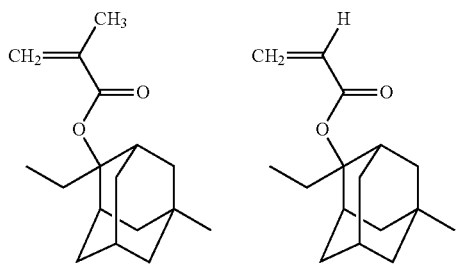

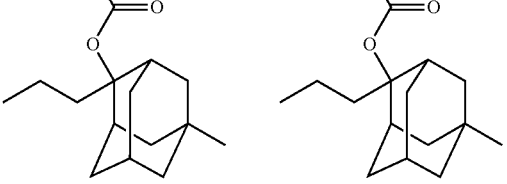

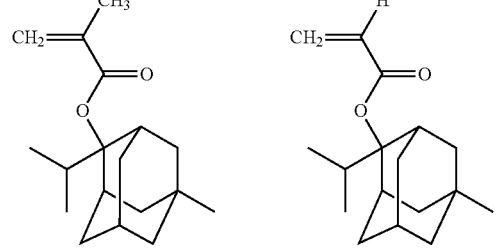

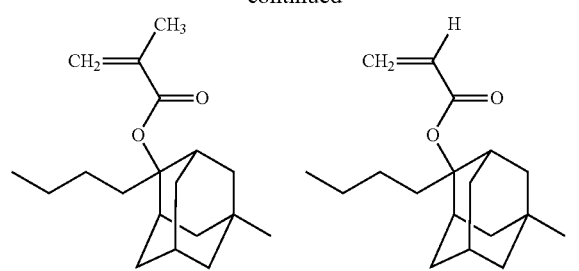
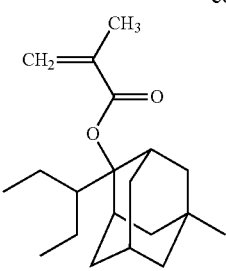
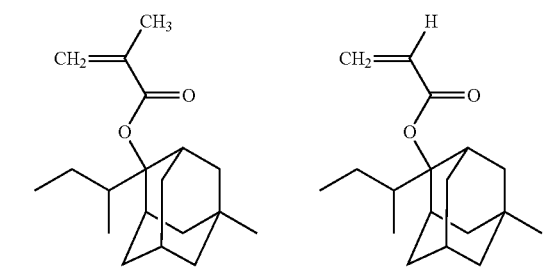
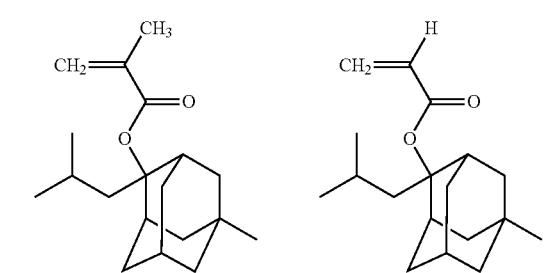
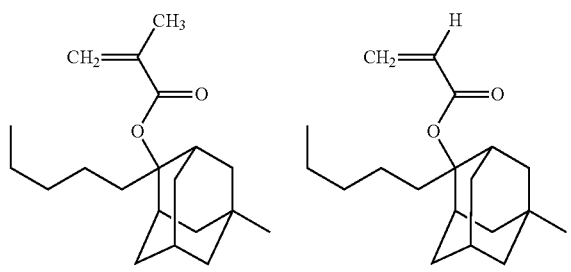
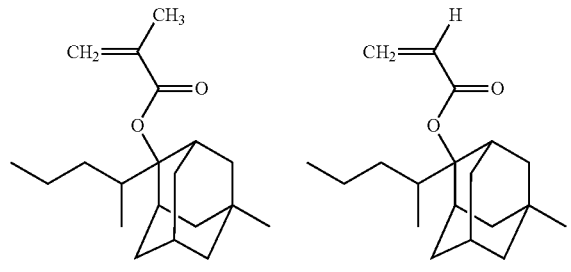
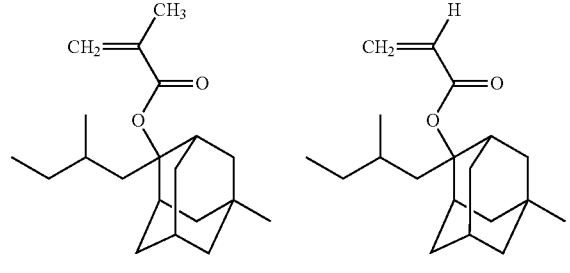

11
-continued
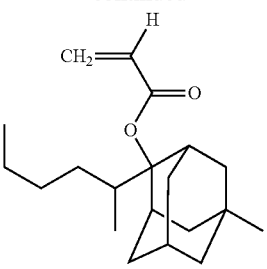
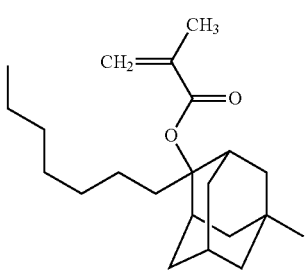
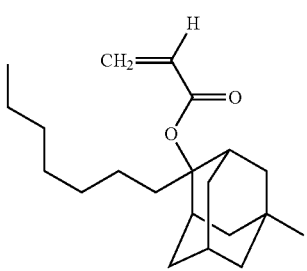
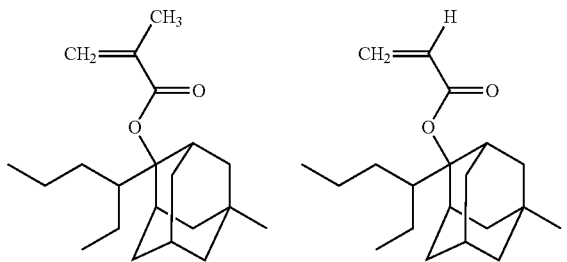
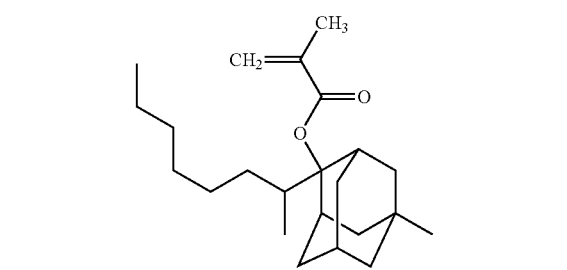
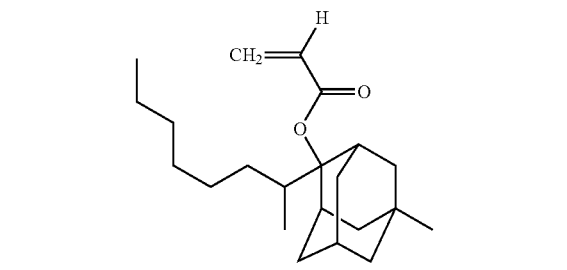
12
-continued
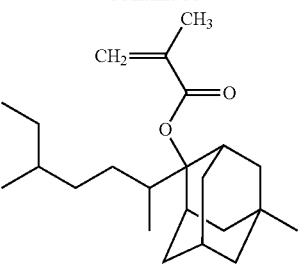
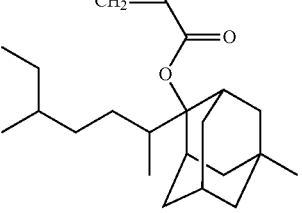
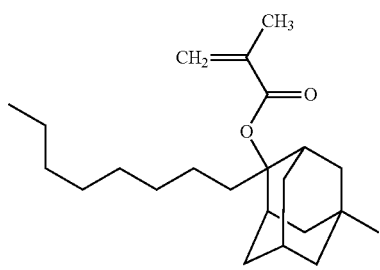
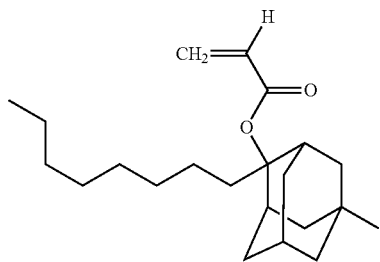
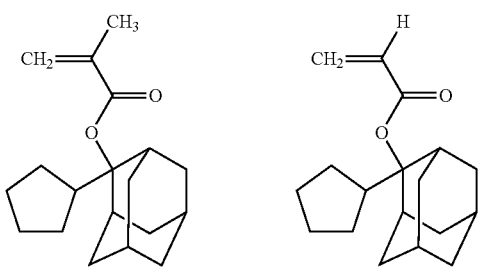
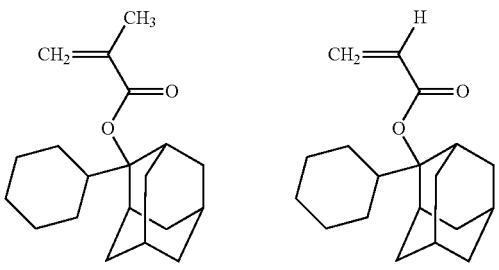

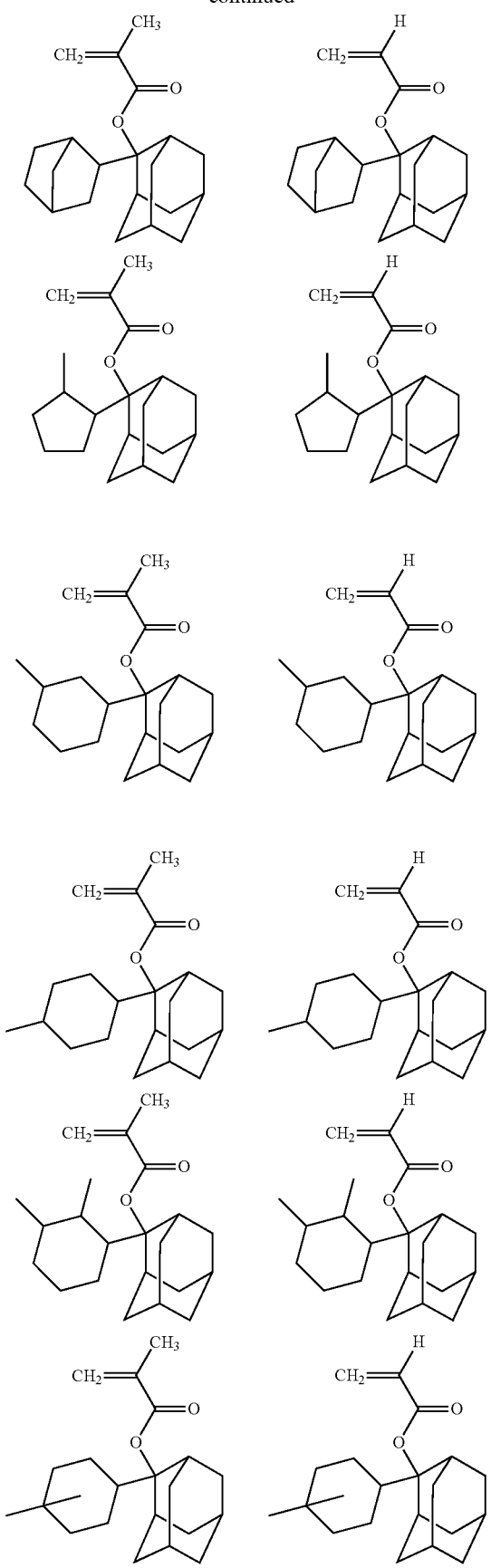
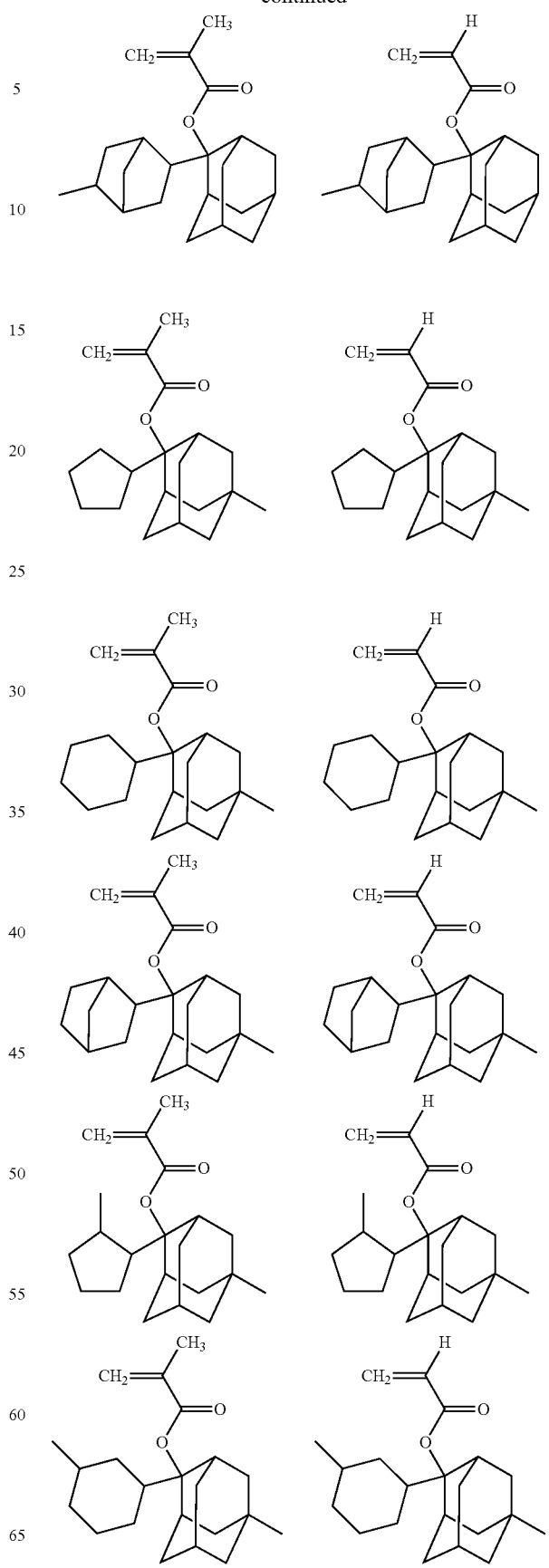

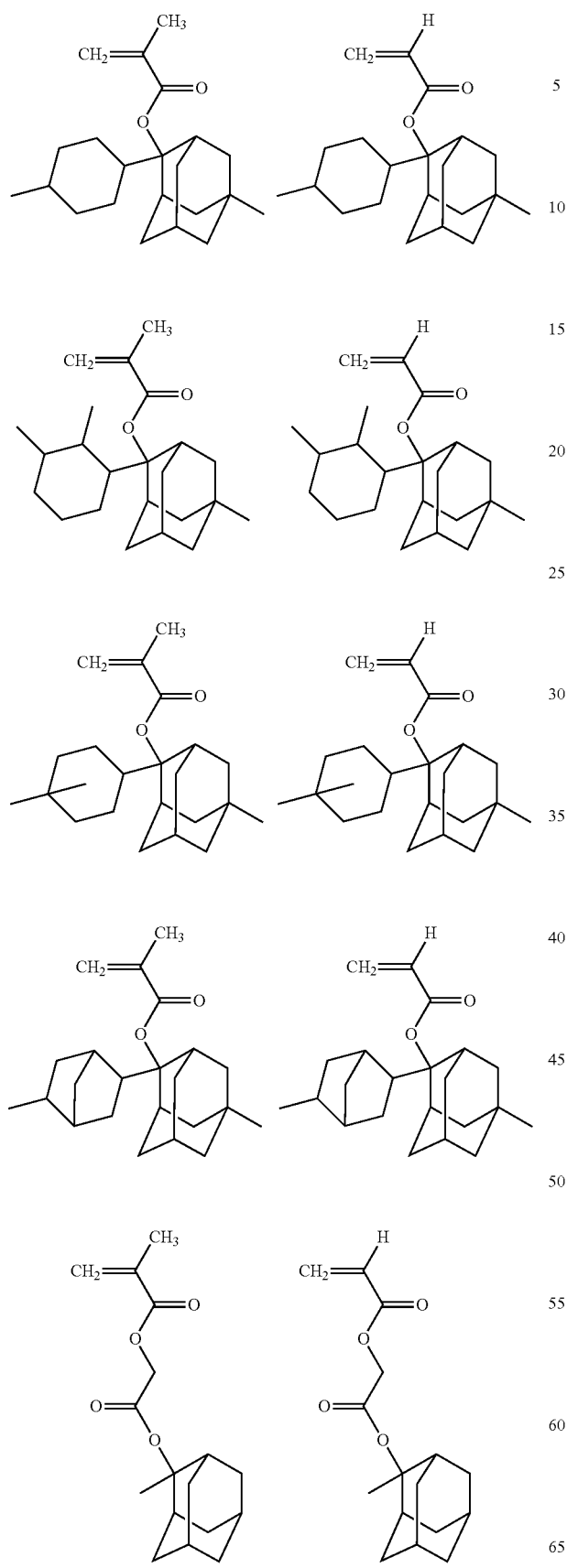
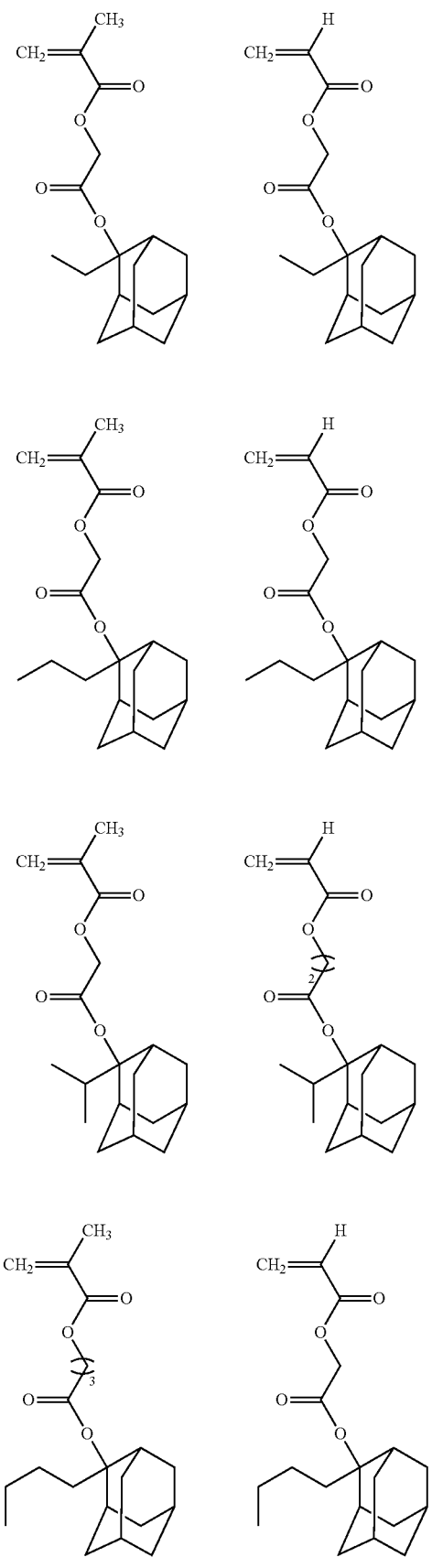

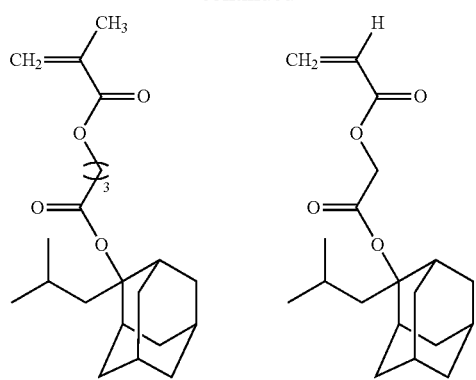
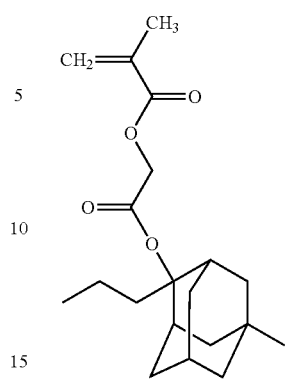
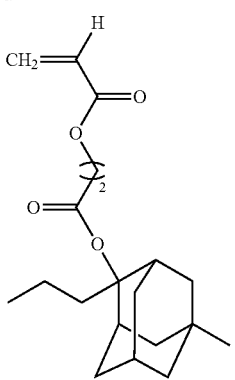
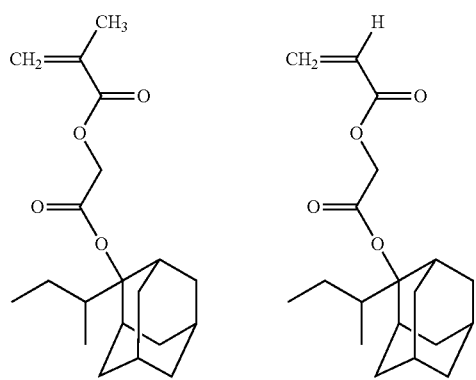
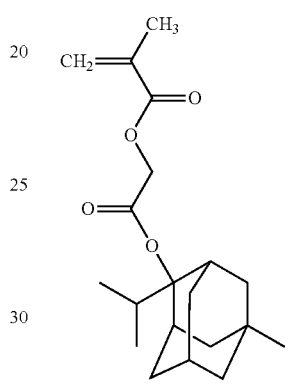
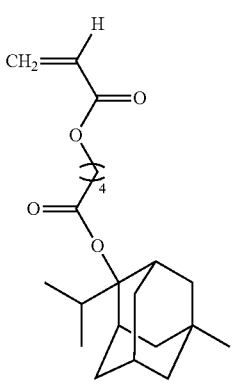
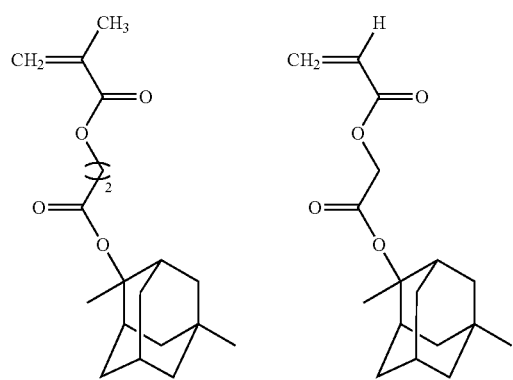
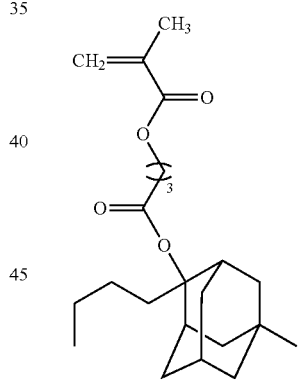
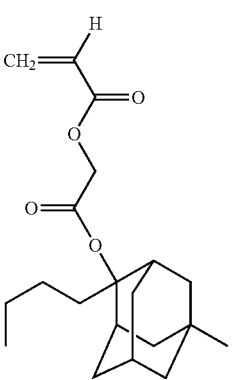
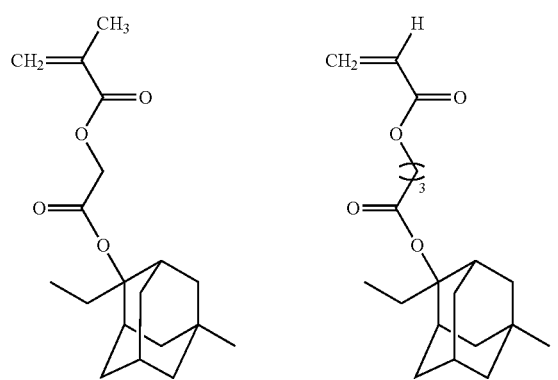
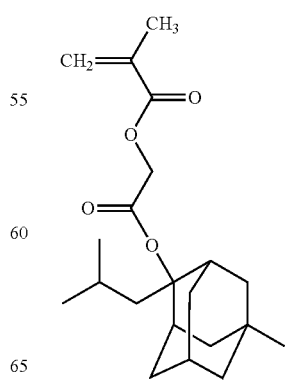
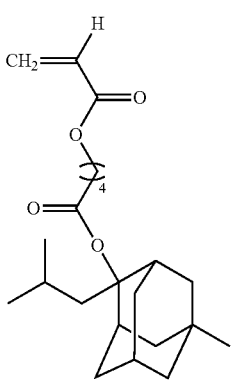

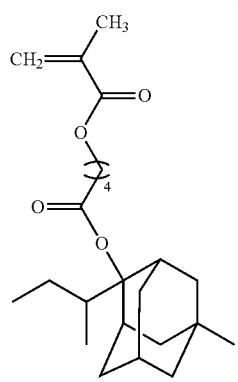 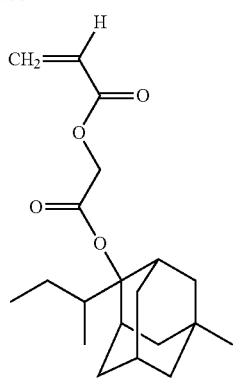 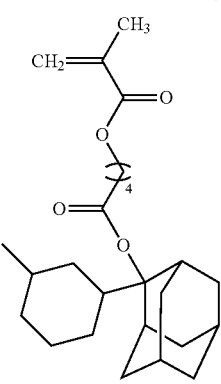 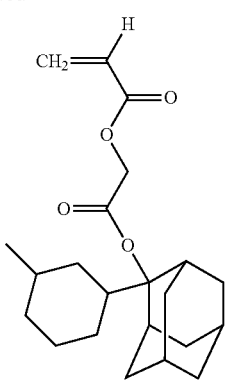
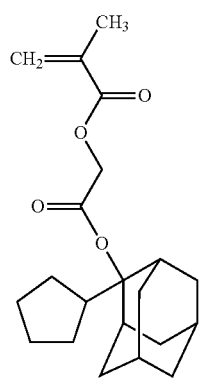 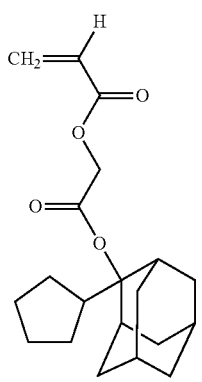 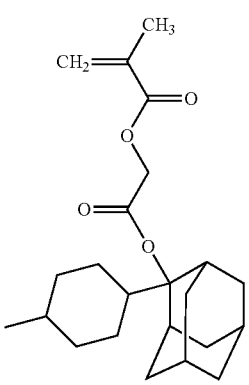 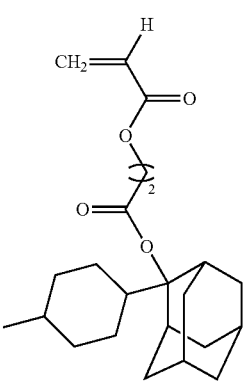
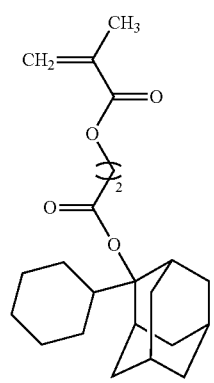 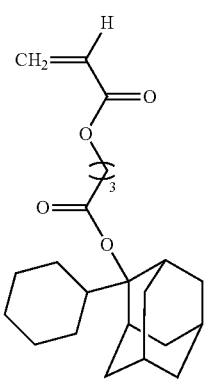 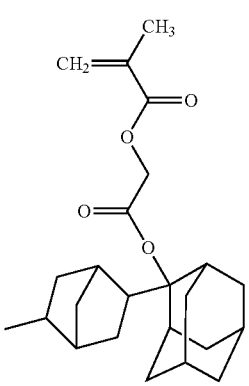 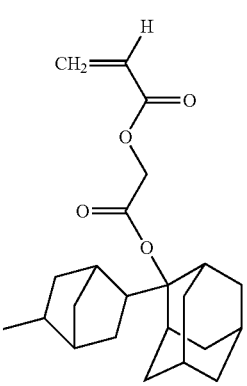
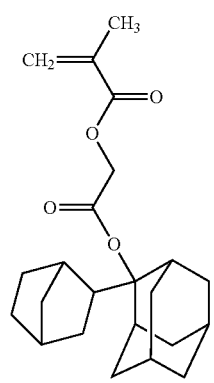 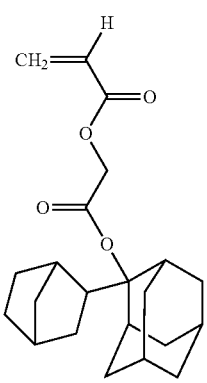 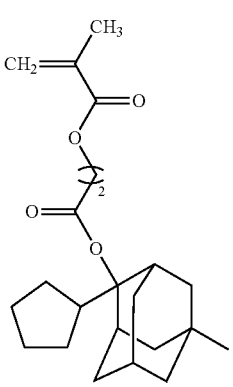 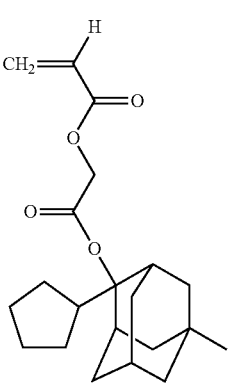

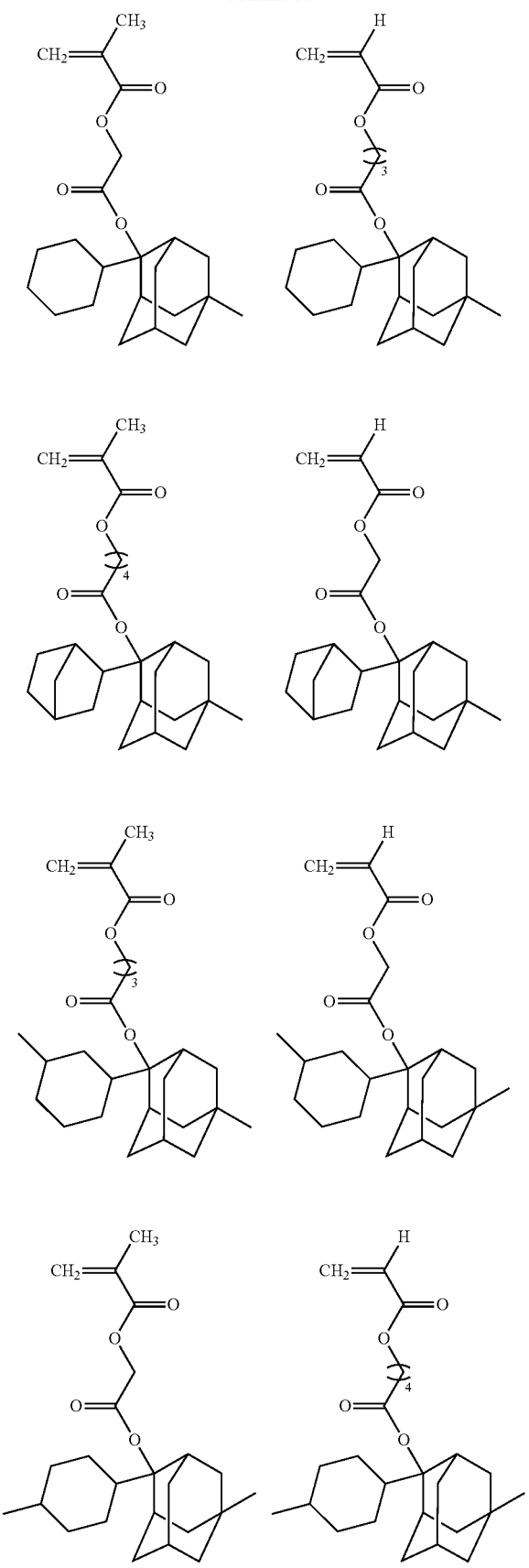
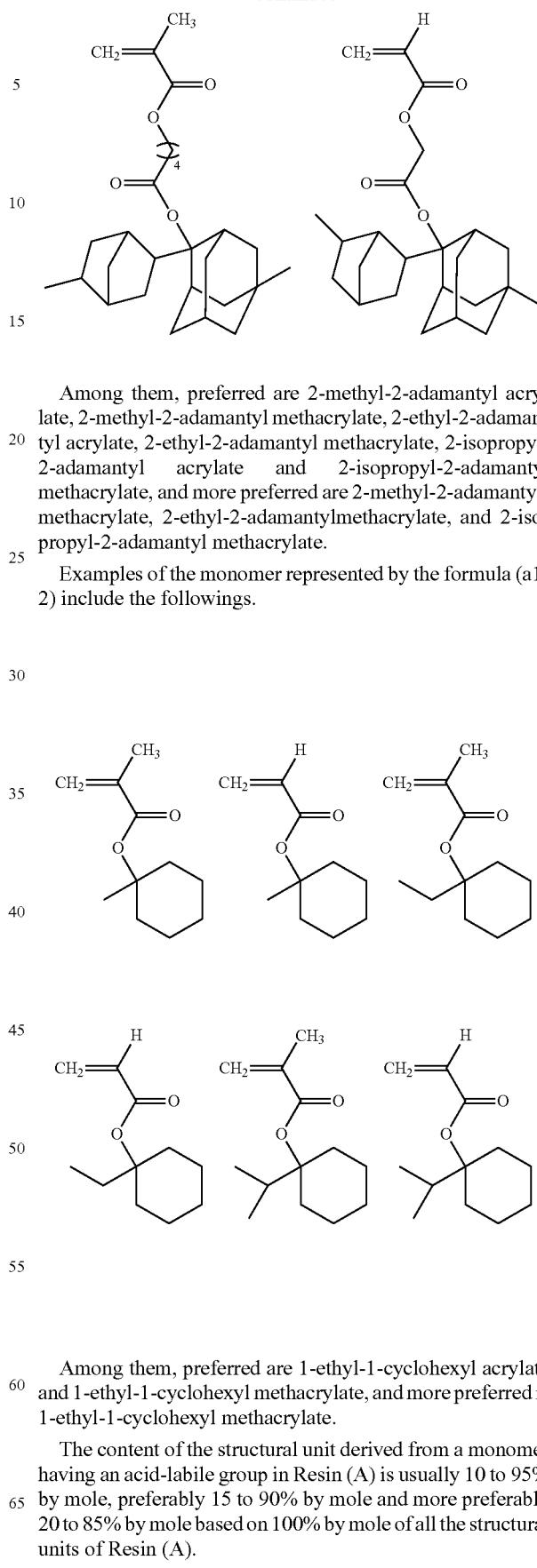

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantylmethacrylate, 2-ethyl-2-adamantylmethacrylate, and 2-isopropyl-2-adamantyl methacrylate.

Examples of the monomer represented by the formula (a1-2) include the followings.

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a monomer having an acid-labile group in Resin (A) is usually 10 to 95% by mole, preferably 15 to 90% by mole and more preferably 20 to 85% by mole based on 100% by mole of all the structural units of Resin (A).

Other examples of the monomer having an acid-labile group include a monomer represented by the formula (a1-3):

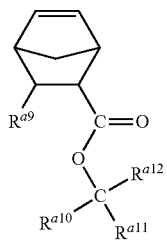

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When Resin (A) has a structural unit derived from the monomer represented by the formula (a1-3), the photoresist composition having excellent resolution and higher dry-etching resistance tends to be obtained.

When Resin (A) contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of Resin (A).

Other examples of the monomer having an acid-labile group include a monomer represented by the formula (a1-4):

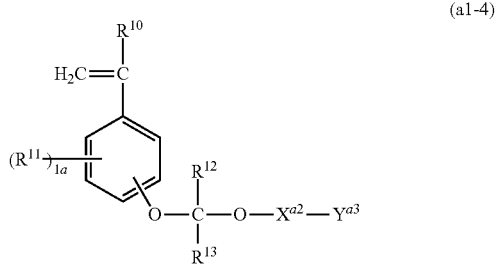

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, la represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein $R^c$ represents a hydrogen atom or a C1-C6 alkyl group, and which can have one or more substituents, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, and a cyclohexane-1,4-diyl group. Examples of the substituents of the C1-C17 divalent saturated hydrocarbon group include a halogen atom such as a fluorine atom, and a hydroxyl group. Examples of the substituted C1-C17 divalent saturated hydrocarbon group include the followings.

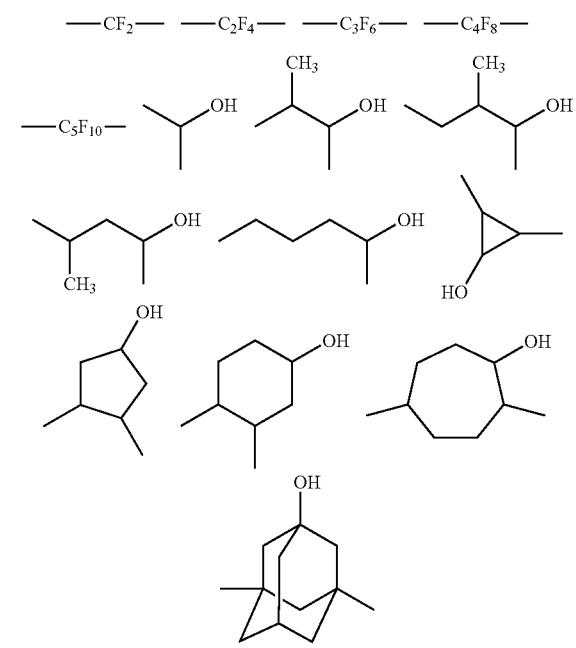

Examples of the C1-C17 divalent saturated hydrocarbon group in which one or more —CH$_2$— are replaced by —O—, —CO—, —S—, —SO$_2$— or —N(R$^c$)— include the followings.

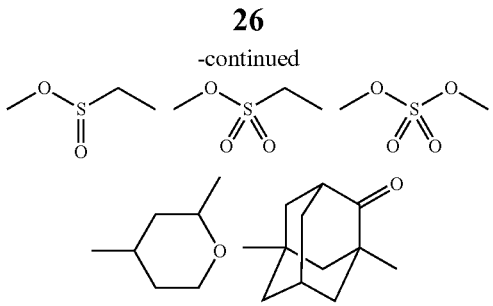

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups.

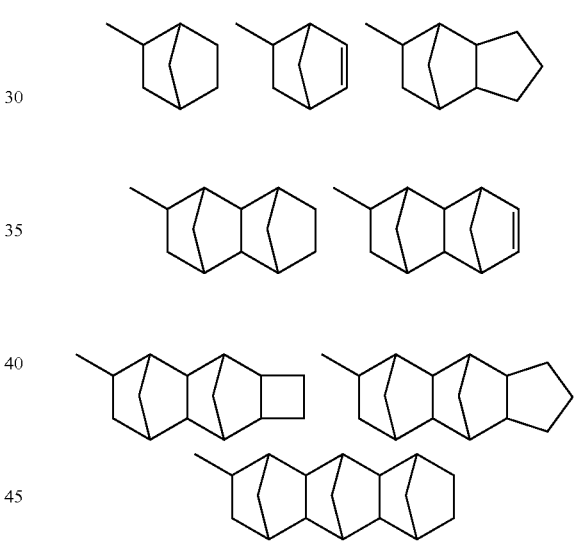

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

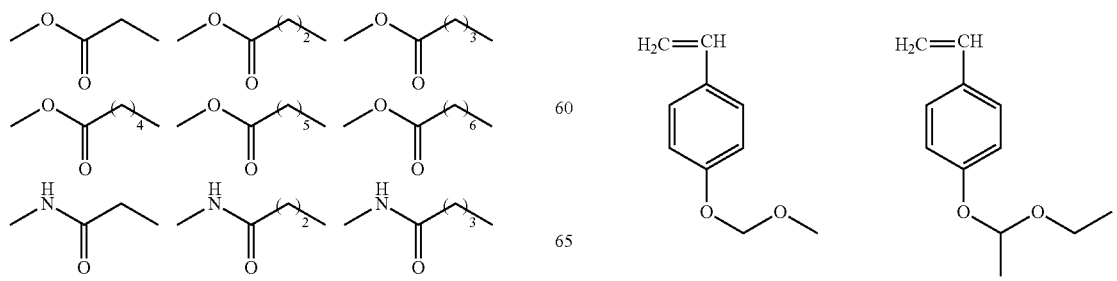

-continued
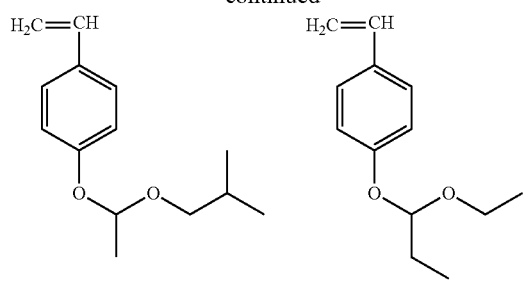
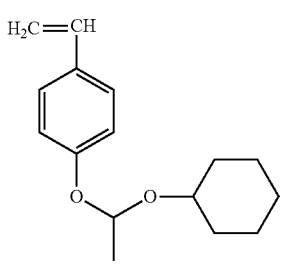
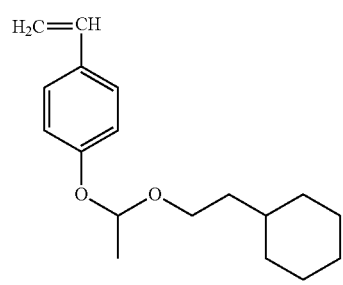
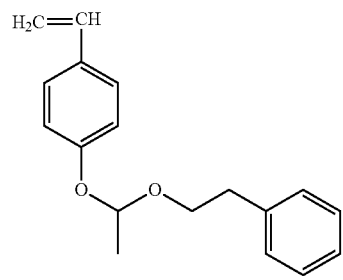
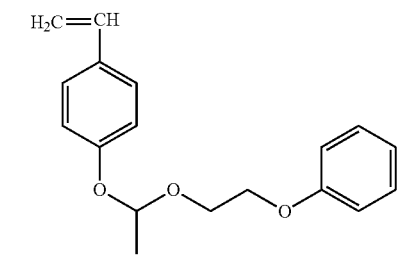
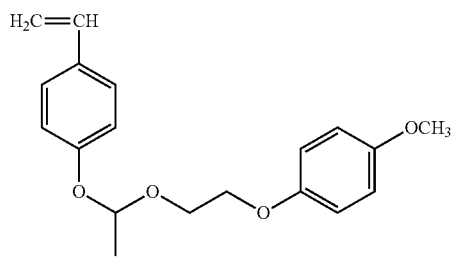
-continued
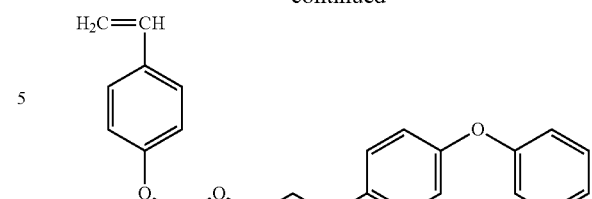
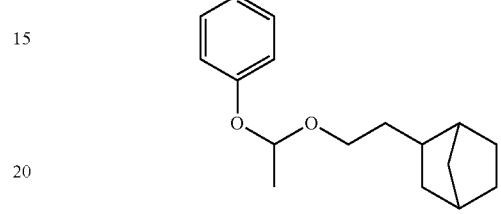
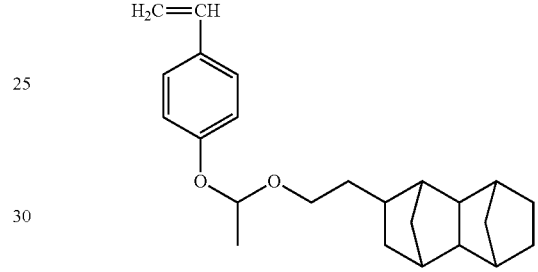
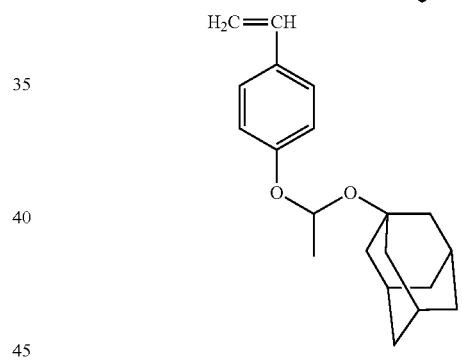
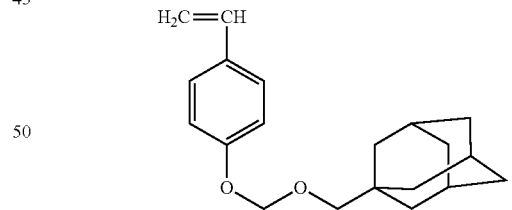
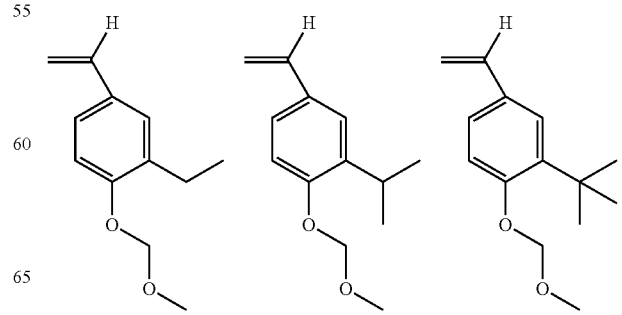

-continued

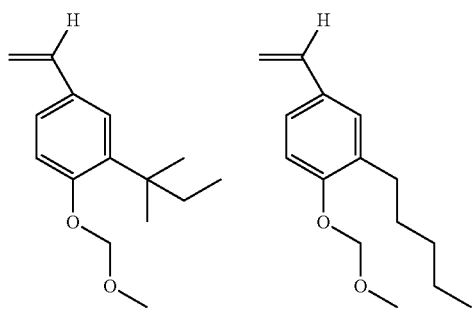

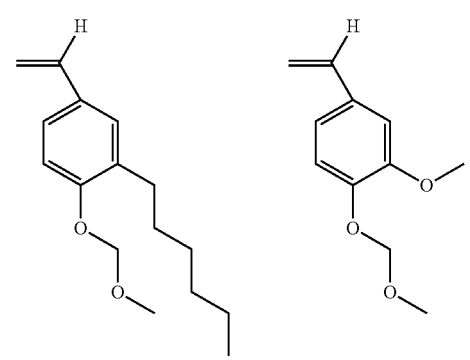

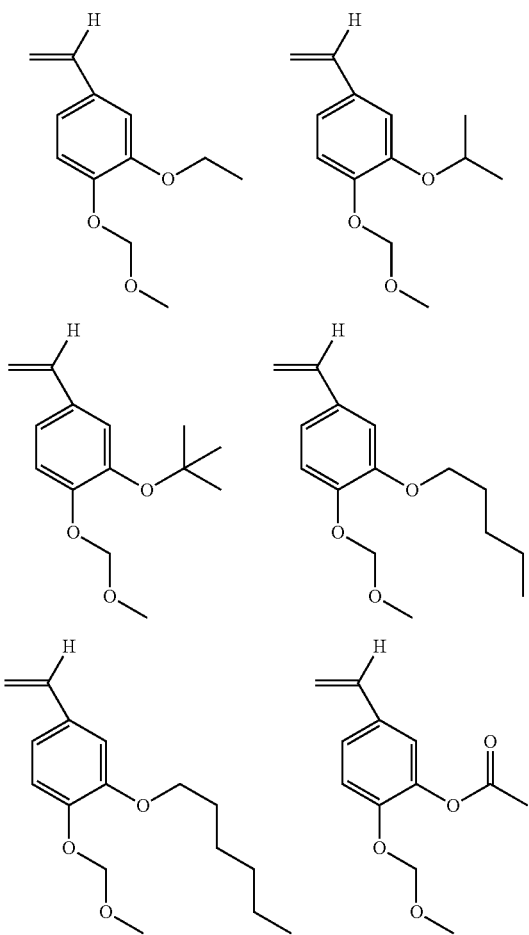

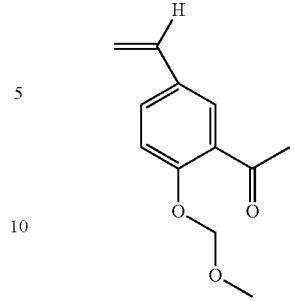

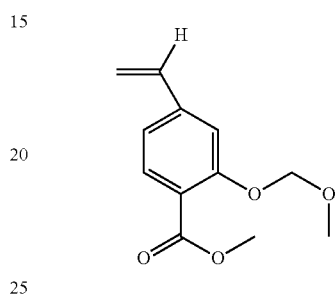

When Resin (A) contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of Resin (A).

Resin (A) can have two or more kinds of structural units derived from the monomers having an acid-labile group.

Resin (A) preferably contains the structural unit derived from the monomer having an acid-labile group and a structural unit derived from the monomer having no acid-labile group. Resin (A) can have two or more kinds of structural units derived from the monomers having no acid-labile group. When Resin (A) contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of Resin (A). The content of the structural unit derived from a monomer having an adamantyl group, especially the monomer represented by the formula (a1-1) in the structural unit derived from the monomer having no acid-labile group, is preferably 15% by mole or more from the viewpoint of dry-etching resistance of the photoresist composition.

The monomer having no acid-labile group preferably contains one or more hydroxyl groups or a lactone ring. When Resin (A) contains the structural unit derived from the monomer having no acid-labile group and having one or more hydroxyl groups or a lactone ring, a photoresist composition having good resolution and adhesiveness of photoresist to a substrate tends to be obtained.

Examples of the monomer having no acid-labile group and having one or more hydroxyl groups include a monomer represented by the formula (a2-0):

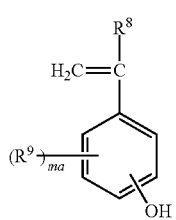

(a2-0)

wherein R⁸ represents a hydrogen atom, a halogen atom, a C1-C6 alkyl group or a C1-C6 halogenated alkyl group, R⁹ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

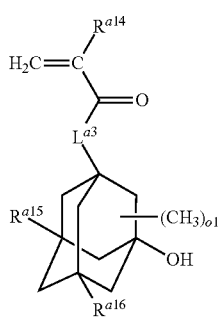

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—(CH$_2$)$_{k2}$—CO—O— in which * represents a binding position to —CO—, and k2 represents an integer of 1 to 7, and o1 represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

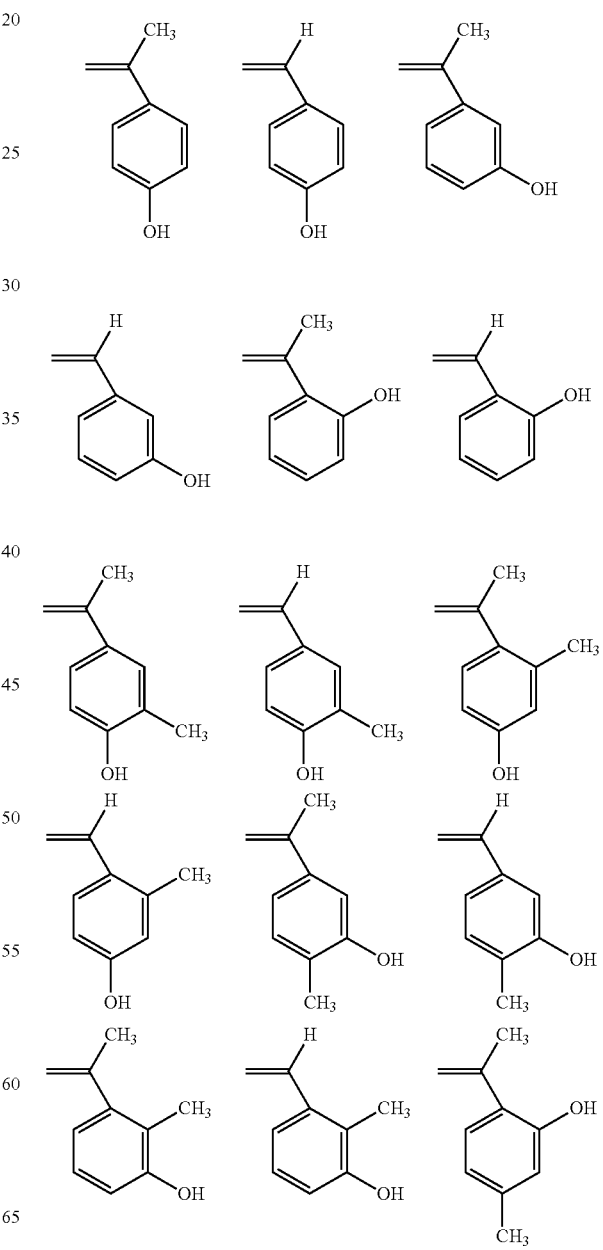

-continued
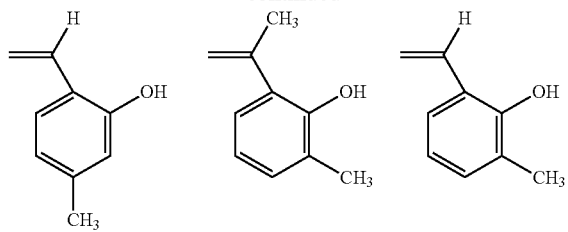
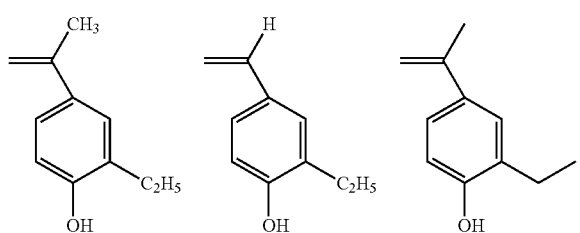
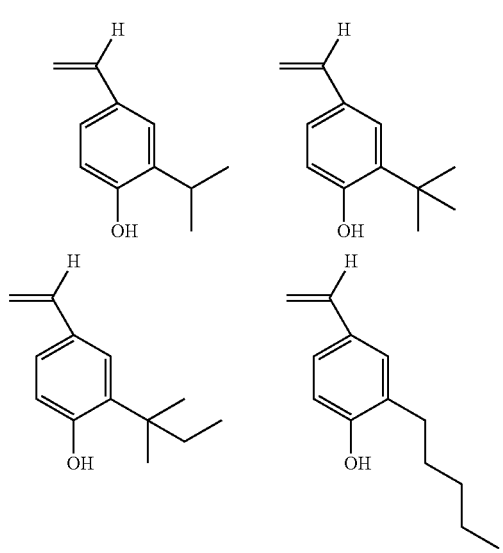
-continued
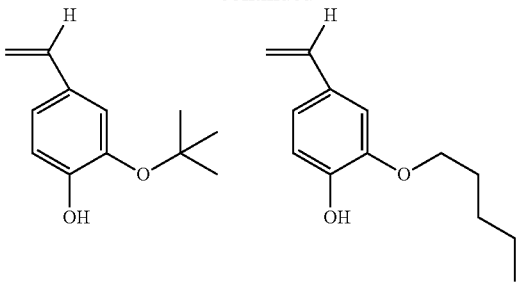
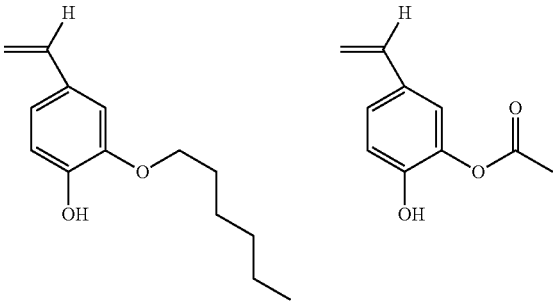
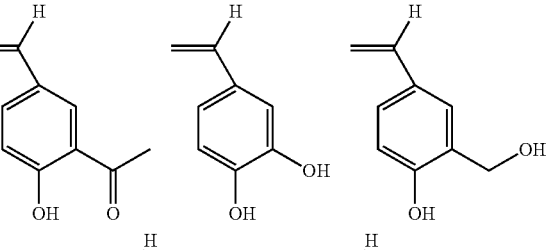
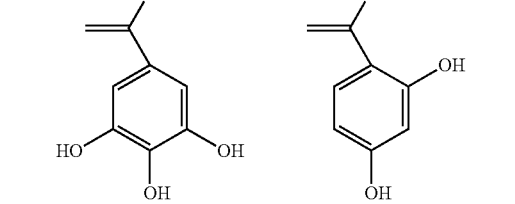
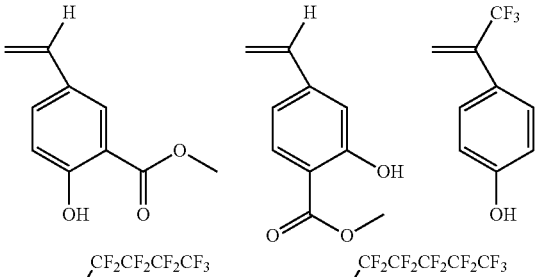
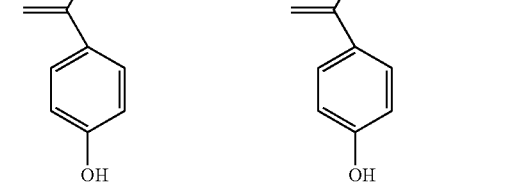
Among them, preferred are 4-hydroxystyrene and 4-hydroxy-α-methylstyrene.
When Resin (A) contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of Resin (A).

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

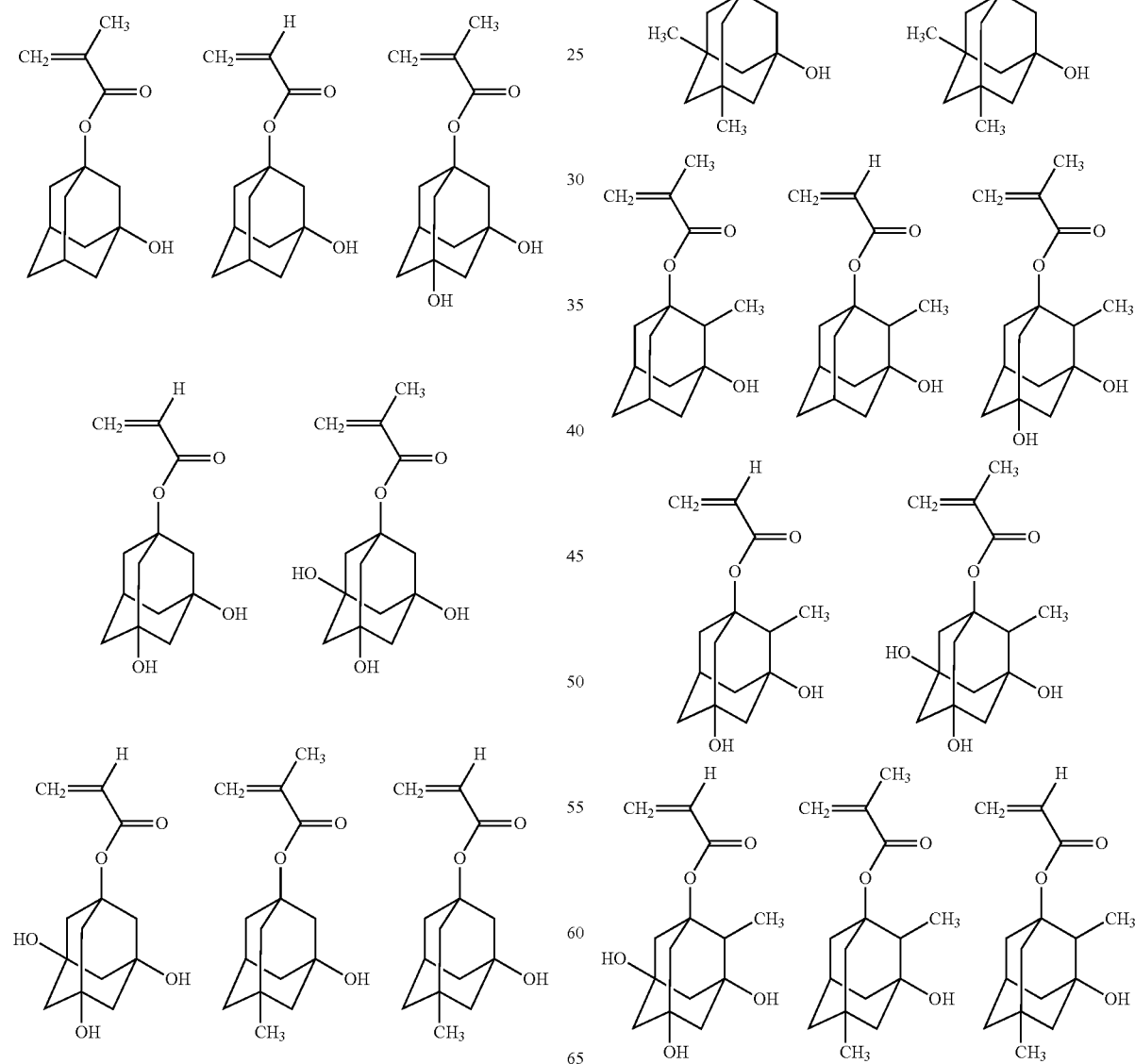

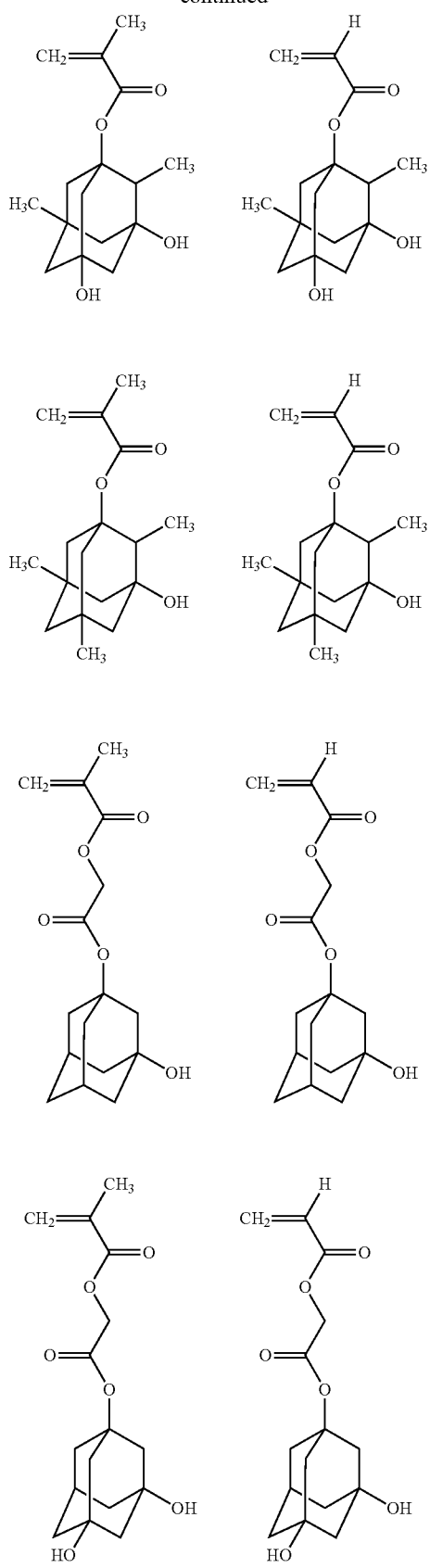
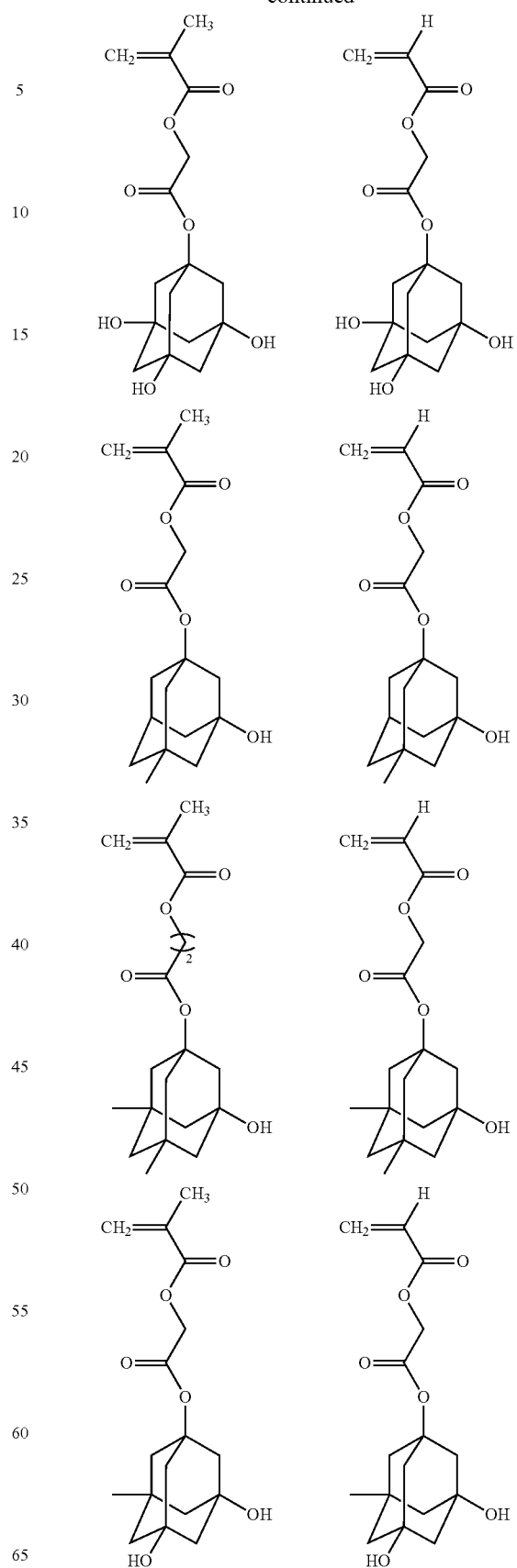

-continued

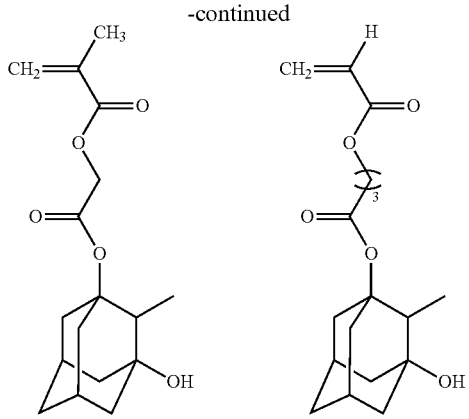

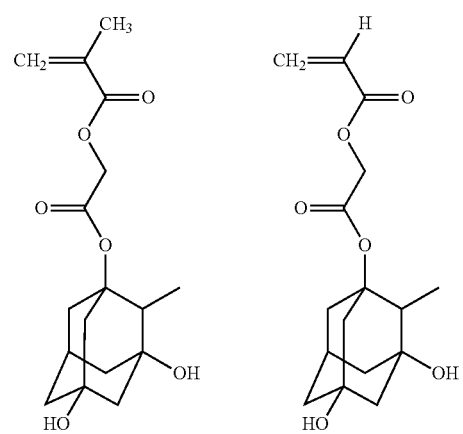

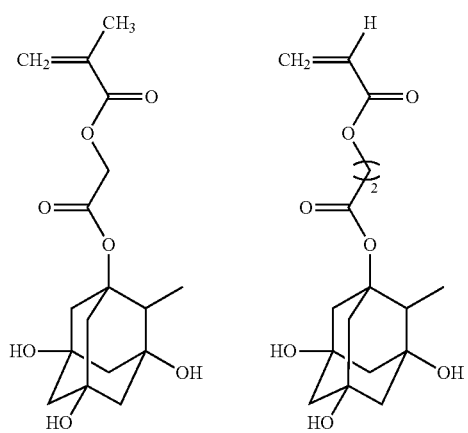

When Resin (A) contains the structural unit derived from the monomer represented by the formula (a2-1), the content of the structural unit derived from the monomer represented by the formula (a2-1) is usually 5 to 50% by mole and preferably 10 to 45% by mole and more preferably 15 to 40% by mole based on total molar of all the structural units of Resin (A).

Examples of the lactone ring of the monomer having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

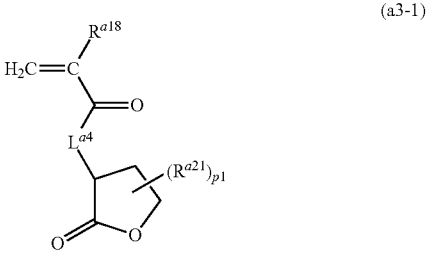

(a3-1)

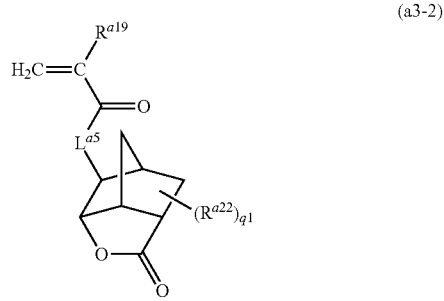

(a3-2)

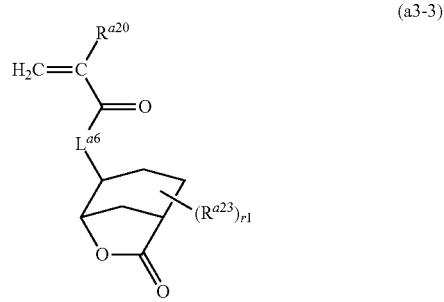

(a3-3)

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a23}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.
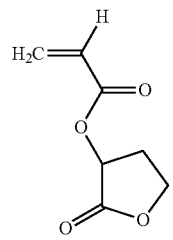 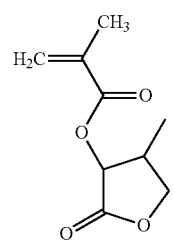 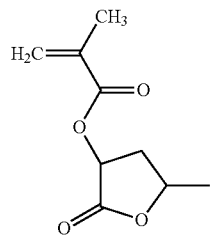
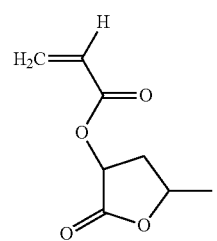 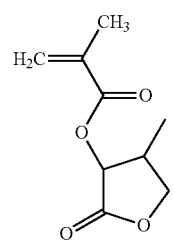 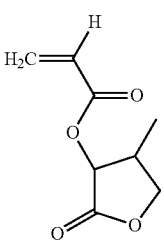
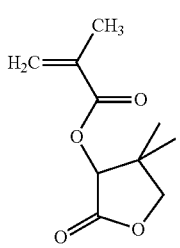 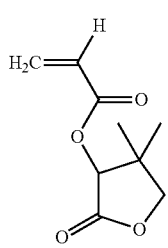 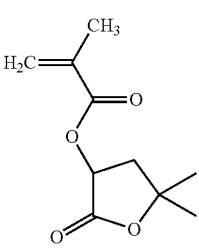
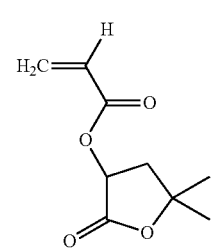 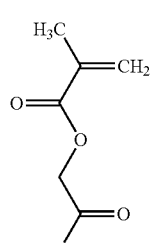 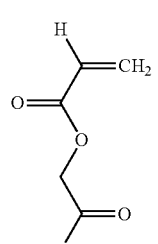
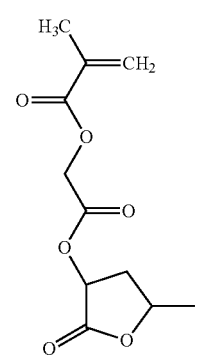 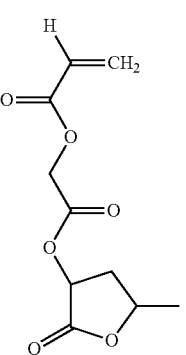 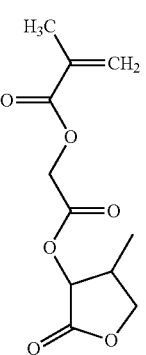
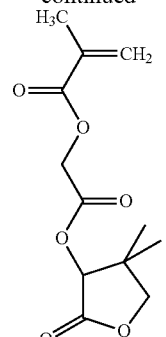 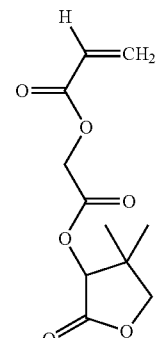
-continued
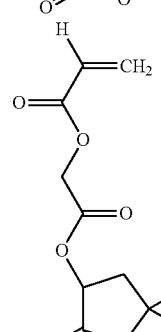 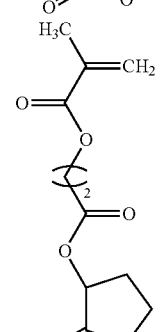
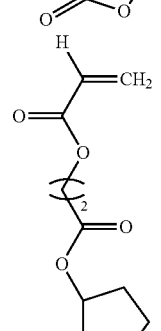 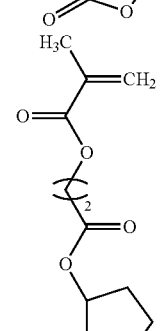
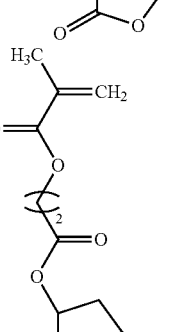 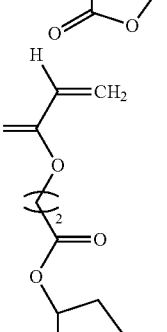
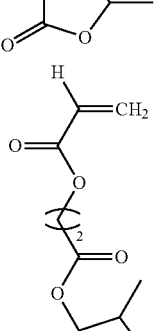 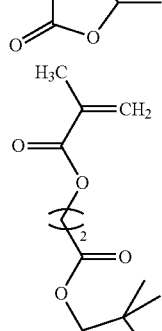

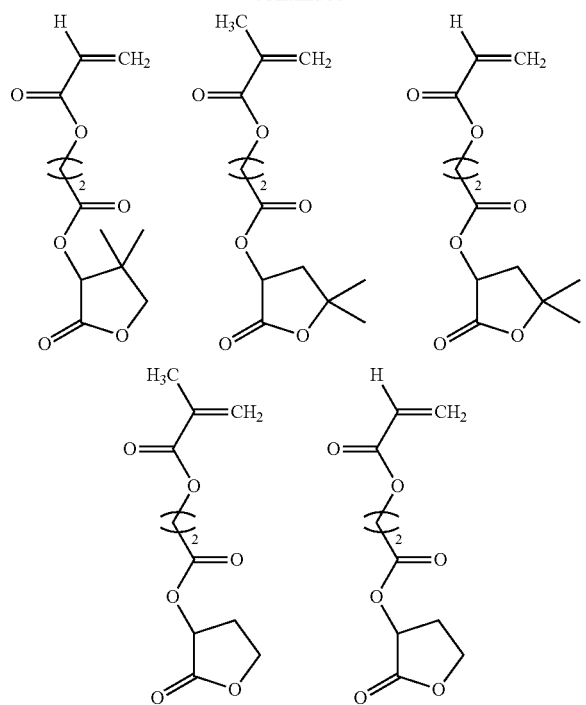
Examples of the monomer represented by the formula (a3-2) include the followings.
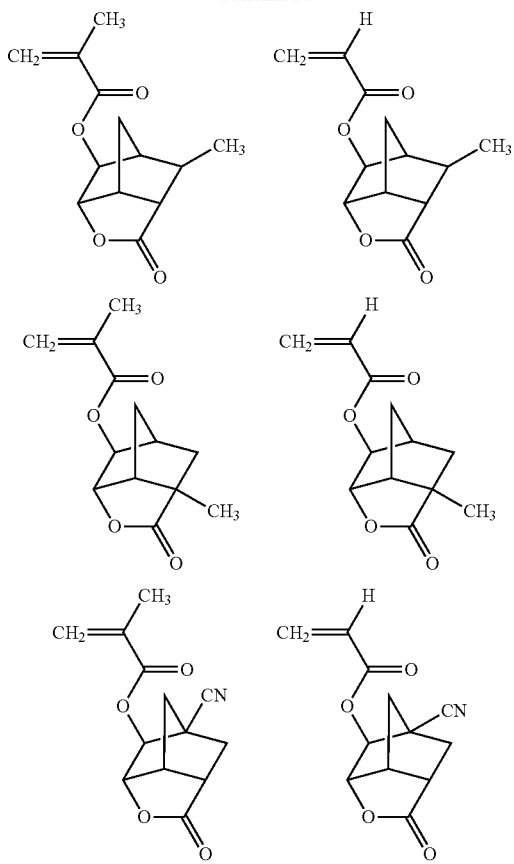
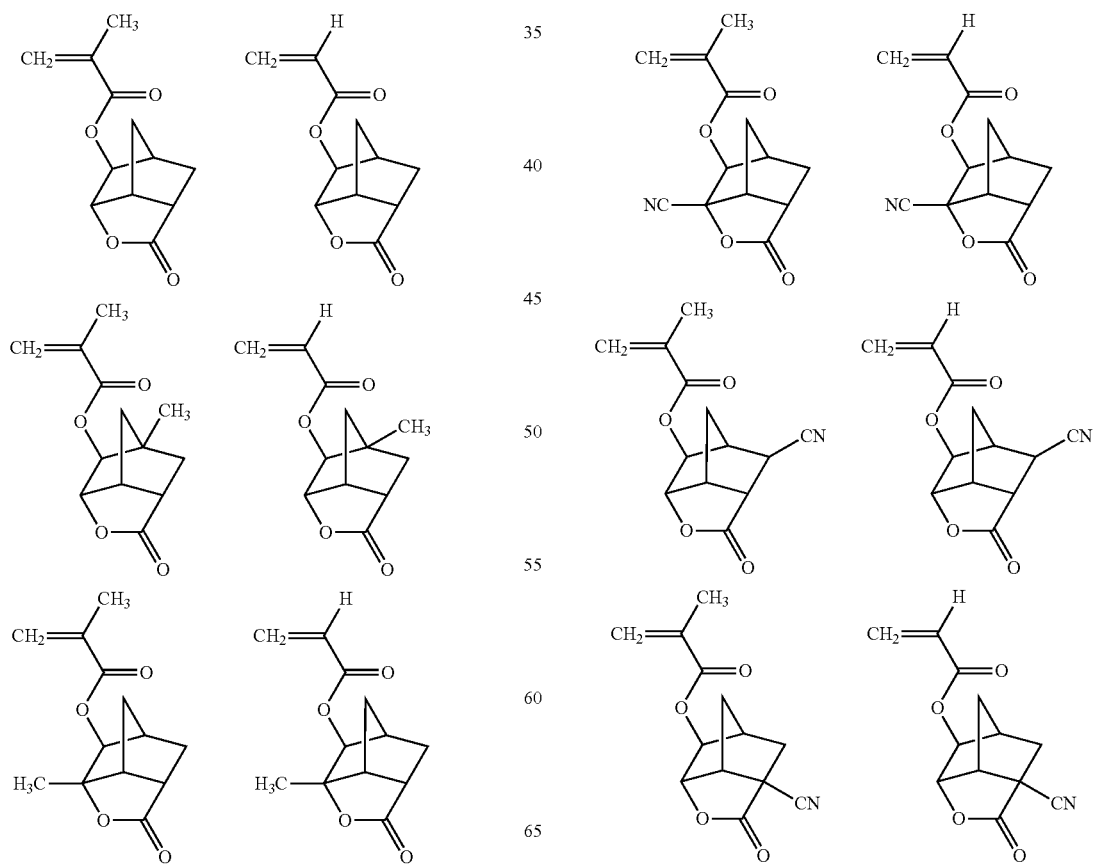

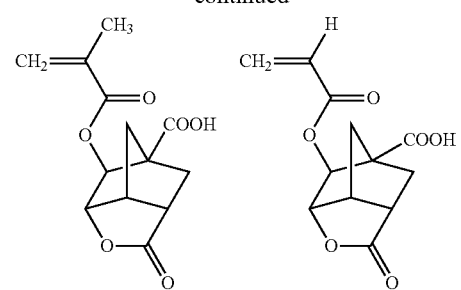
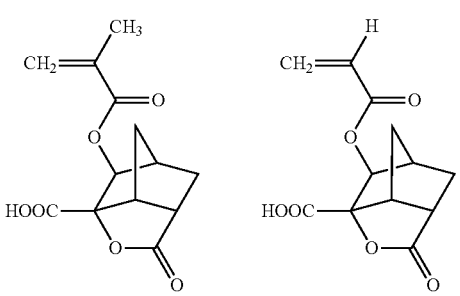
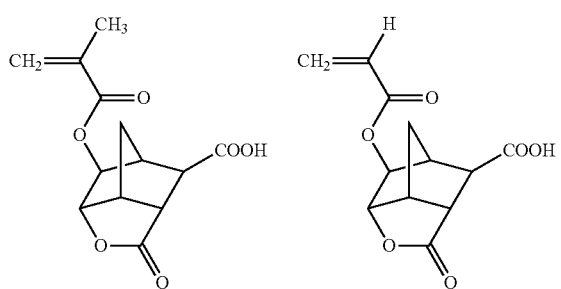
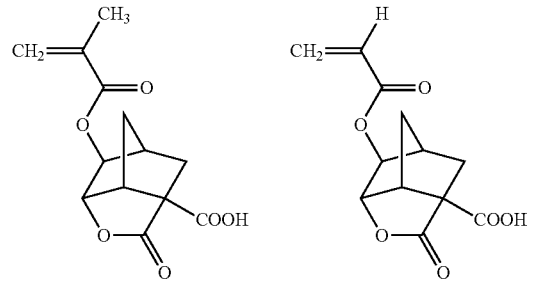
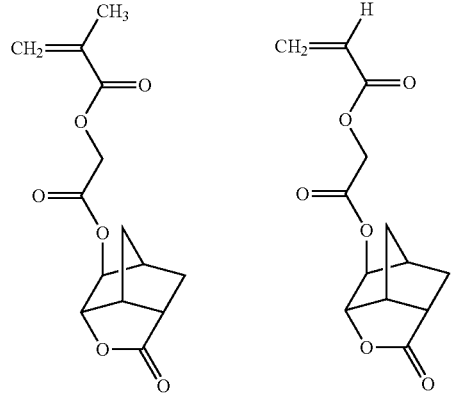
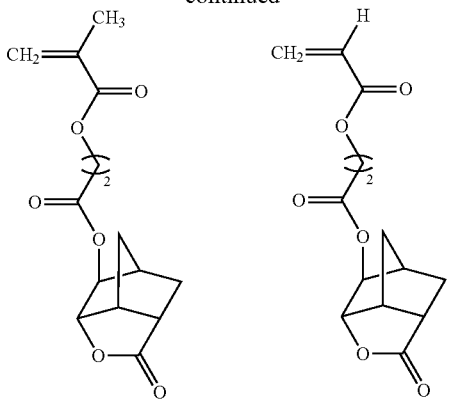
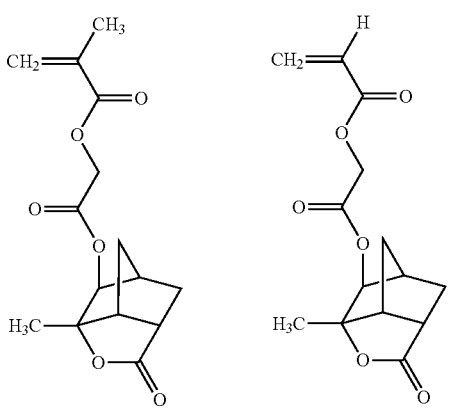
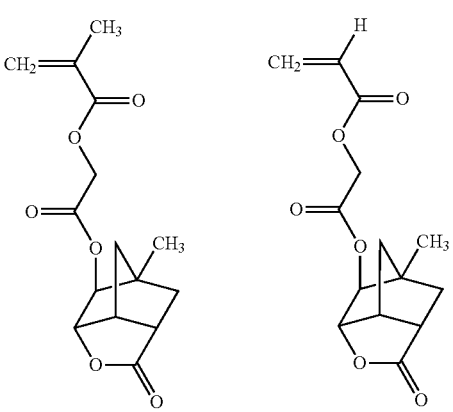
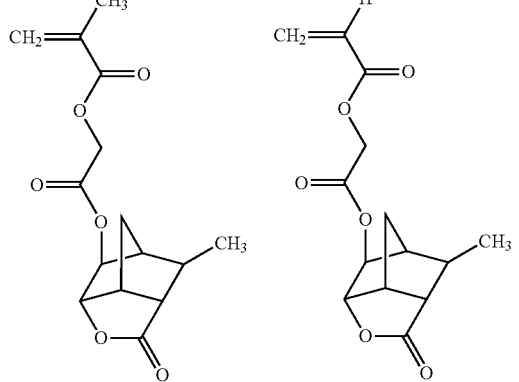

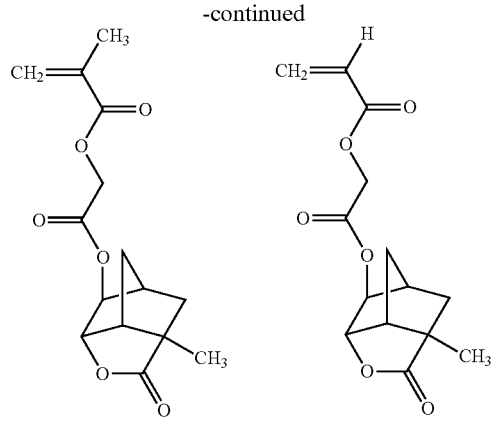
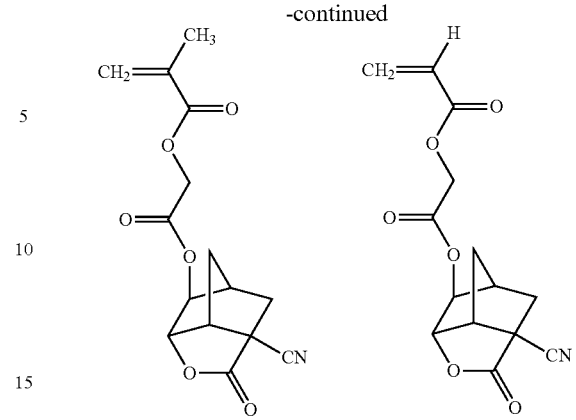
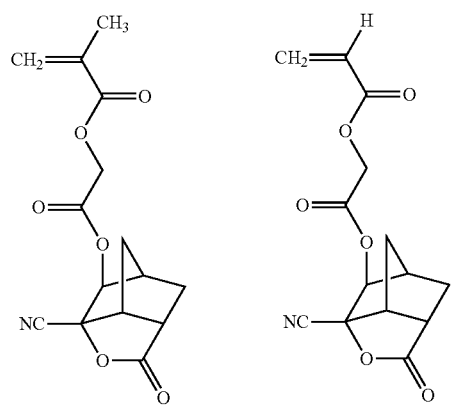
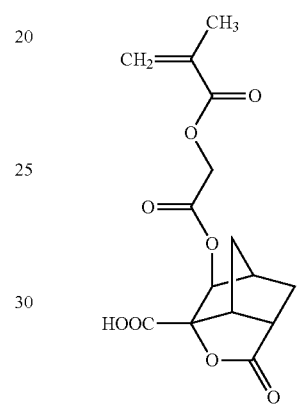
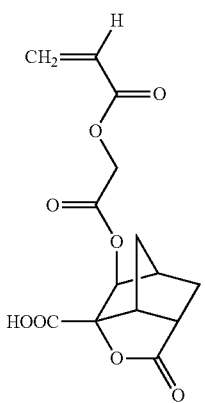
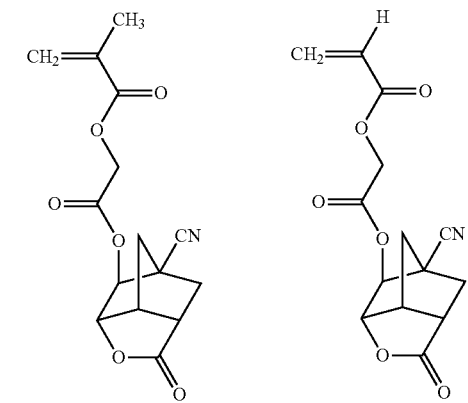
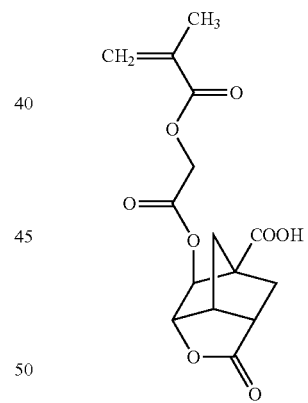
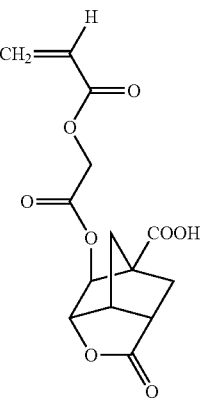
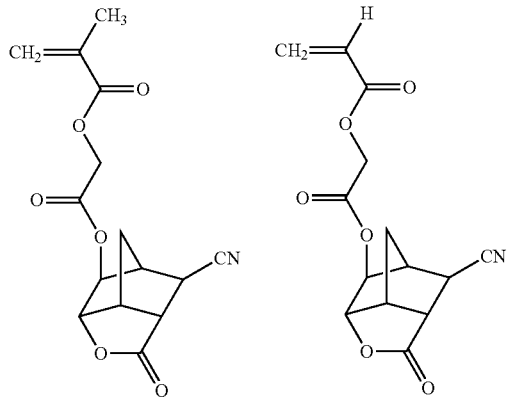
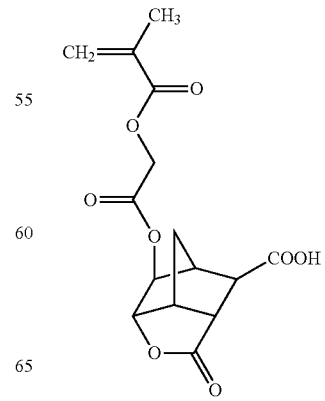
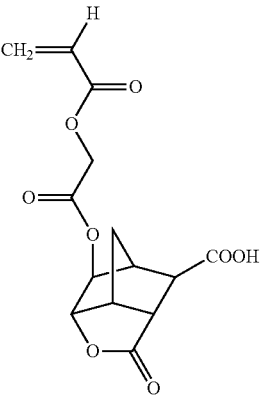

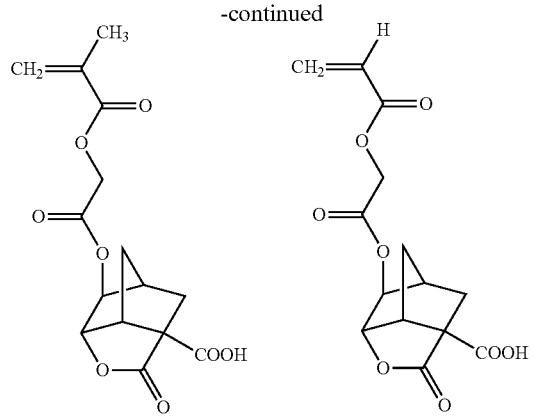
Examples of the monomer represented by the formula (a3-3) include the followings.
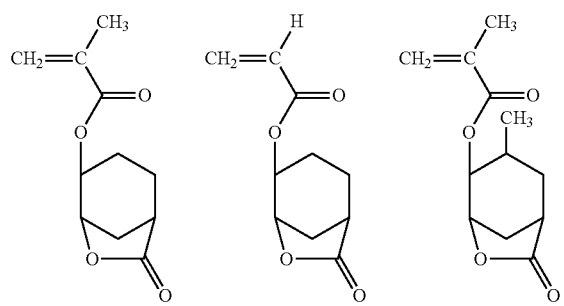
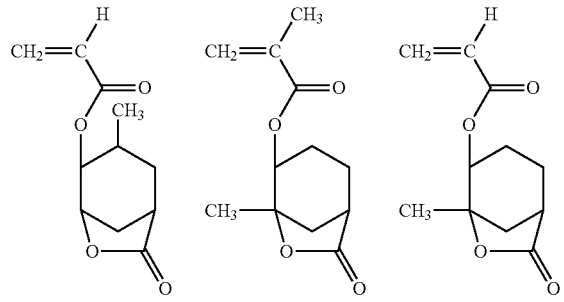
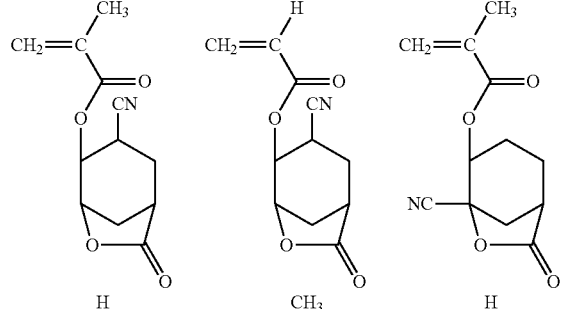
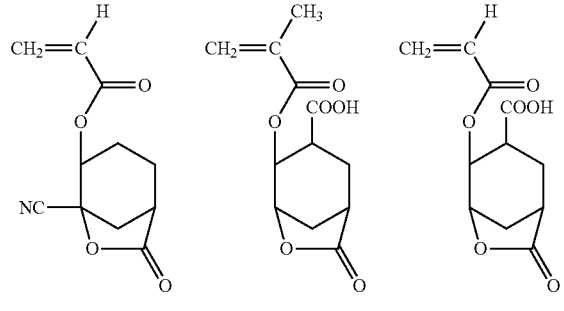
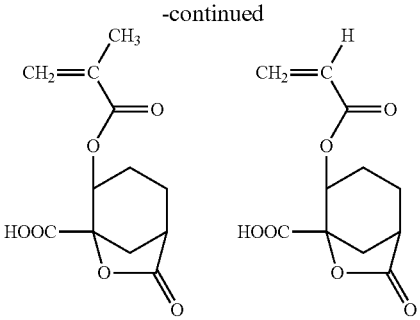
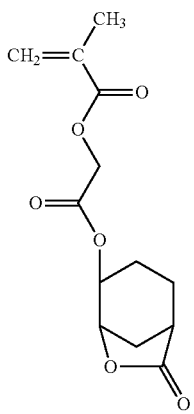
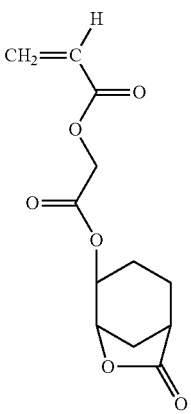
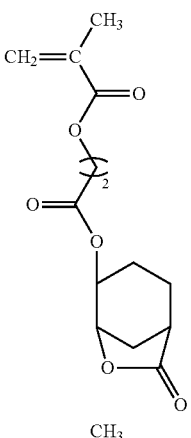
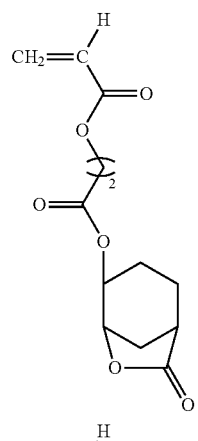
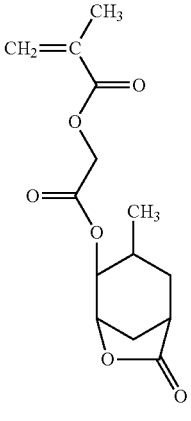
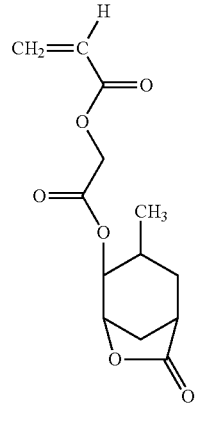

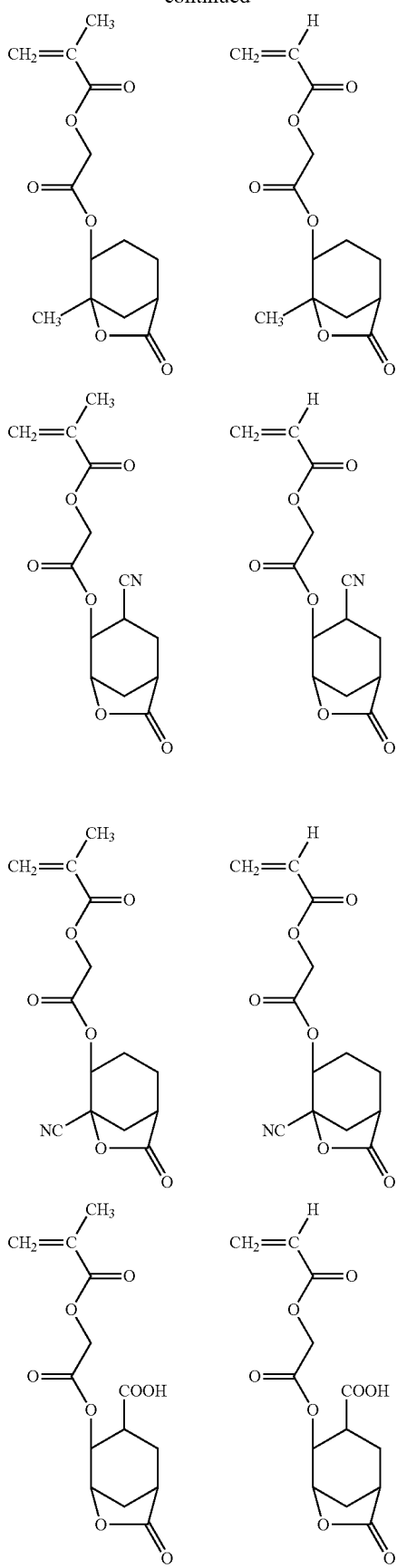

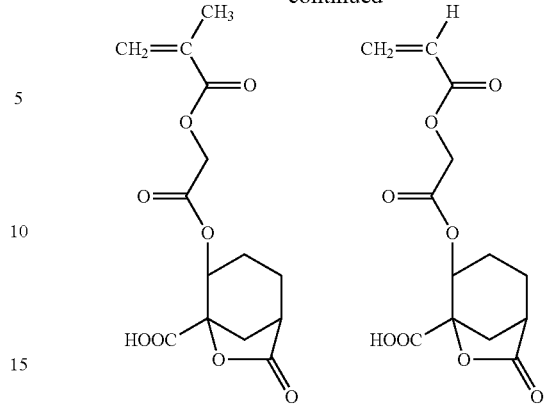

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When Resin (A) contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of Resin (A).

Resin (A) can contain a structural unit derived from a monomer having an acid-labile group containing a lactone ring. Examples of the monomer having an acid-labile group containing a lactone ring include the followings.

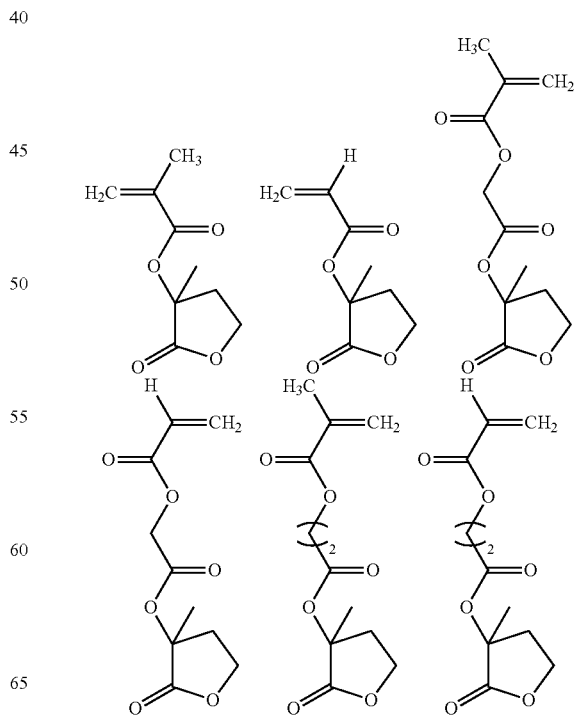

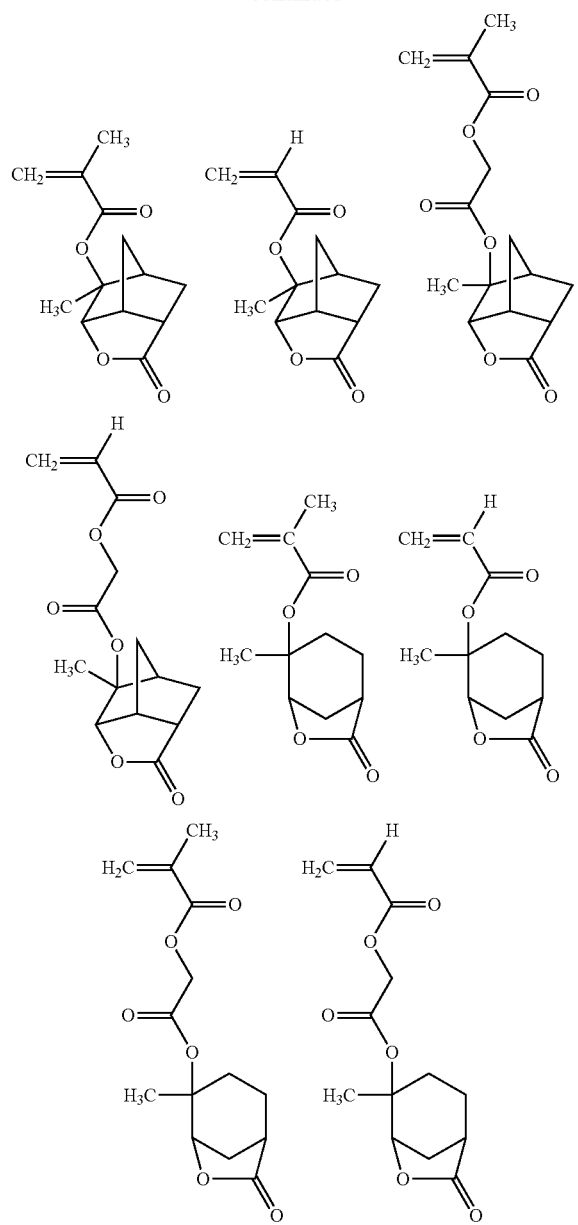

Examples of the other monomer having no acid-labile group include the monomers represented by the formulae (a4-1), (a4-2), (a4-3) and (a4-4):

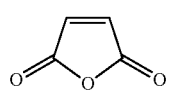
(a4-1)

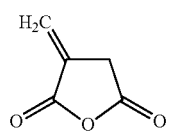
(a4-2)

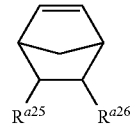
(a4-3)

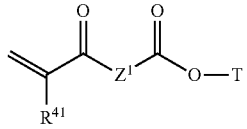
(a4-4)

wherein $R^{a25}$ and $R^{a26}$ each independently represents a hydrogen atom, a C1-C3 aliphatic hydrocarbon group which can have one or more substituents, a carboxyl group, a cyano group or a —COOR$^{a27}$ group in which $R^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)OC(=O)—, T represents a heterocyclic group containing —SO$_2$— as skeleton, one or more hydrogen atoms contained in the heterocyclic group can be replaced by a halogen atom, a hydroxy group, a C1-C12 alkyl group, a C1-C12 alkoxyl group, a C6-C12 aryl group, a C7-C13 aralkyl group or a C2-C4 acyl group, and one or more —CH$_2$— contained in the heterocyclic group may be replaced by —CO— or —O—, $R^{41}$ represents a hydrogen atom or a methyl group and $Z^1$ represents a divalent C1-C17 saturated hydrocarbon group, and one or more —CH$_2$— contained in the saturated hydrocarbon group may be replaced by —O— or —CO—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by $R^{a27}$ is preferably a C1-C8 aliphatic hydrocarbon group and is more preferably a C1-C6 aliphatic hydrocarbon group. The C3-C36 saturated cyclic hydrocarbon group represented by $R^{a27}$ is preferably a C4-C36 saturated cyclic hydrocarbon group, and is more preferably C4-C12 saturated cyclic hydrocarbon group. Examples of $R^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

In the formula (a4-4), $Z^1$ is preferably an alkylene group in which one or more —CH$_2$— is replaced by —O— or —CO. Examples of $Z^1$ include —O—X$^{11}$—, —X$^{11}$—O—, —X$^{11}$—CO—O—, —X$^{11}$—O—CO— and —X$^{11}$—O—X$^{12}$—, preferably —O—X$^{11}$—, —X$^{11}$—O— and —X$^{11}$—CO—O—, and more preferably —O—X$^{11}$—. Among these, —O—CH$_2$— is still more preferable as $Z^1$. $X^{11}$ and $X^{12}$ each independently represents a single bond or a C1-C6 alkylene group, provided that main chain constituting the groups in which one or more —CH$_2$— contained in the alkylene group replaced by —CO— or —O— suitably have 1 to 17 atoms, preferably 1 to 11 atoms, and more preferably 1 to 5 atoms. Examples of the aralkyl group include a benzyl group and a phenethyl group. Examples of the aryl group include a phenyl group, a naphthyl group, an anthranyl group, a p-methylphenyl group, a p-tert-butylphenyl group and a p-adamantylphenyl group. In the formula (a4-4), T is preferably a group having a norbornane skeleton. T is preferably a group represented by the formula (T3), and more preferably a group represented by the formula (T4).

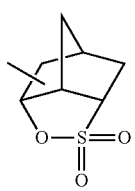
(T3)

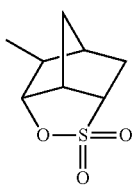
(T4)

wherein one or more hydrogen atoms contained in the ring can be replaced by a halogen atom, a hydroxyl group, a C1-C12 alkyl group, a C1-C12 alkoxyl group, a C6-C12 aryl group, a C7-C13 aralkyl group or a C2-C4 acyl group, and one or more —CH$_2$— contained in the ring may be replaced by —CO— or —O—.

Examples of the C1-C12 alkyl group, the C1-C12 alkoxyl group, the C6-C12 aryl group, the C7-C13 aralkyl group and the C2-C4 acyl group include the same as described above, respectively.

Examples of the monomer represented by the formula (a4-4) include the followings.

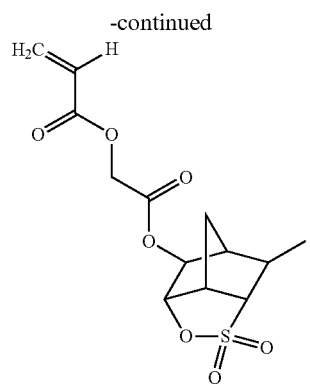

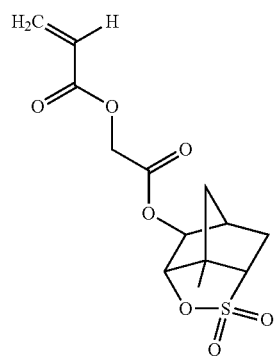

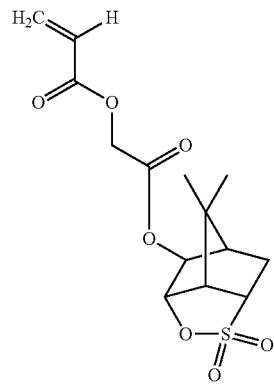

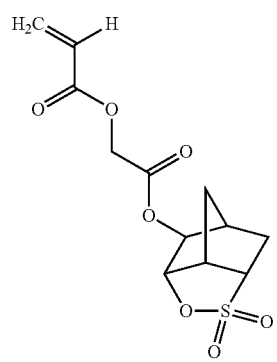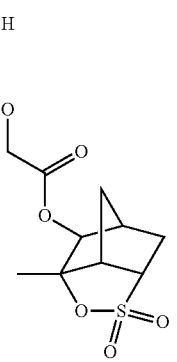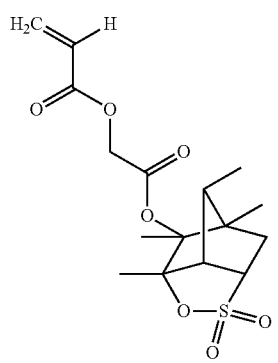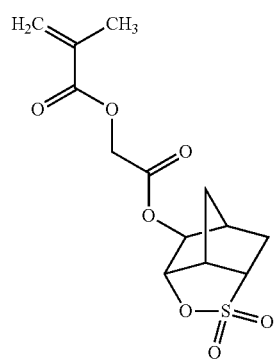

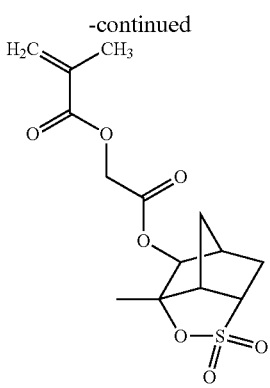
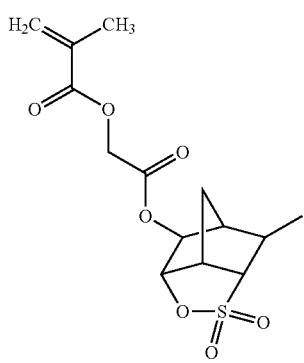
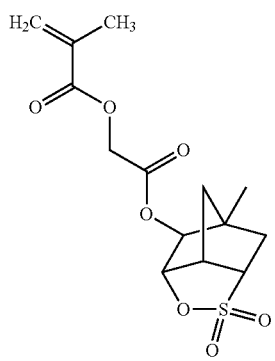
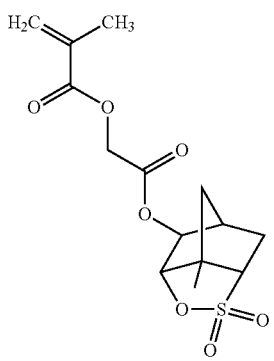
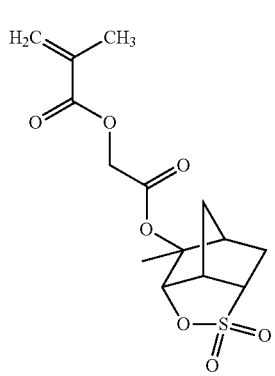
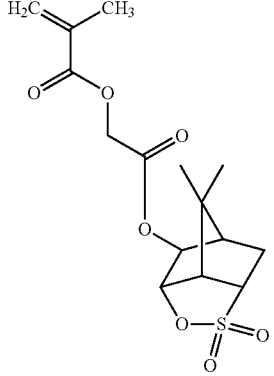

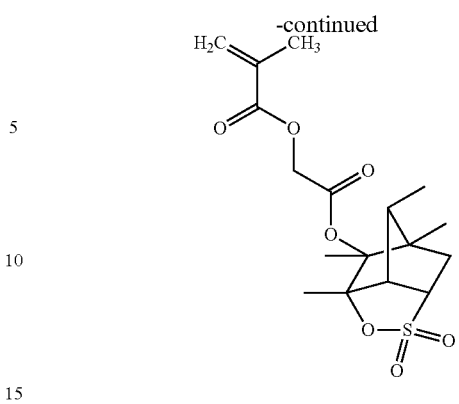

The content of the structural unit derived from a monomer represented by the formula (a4-1), (a4-2) or (a4-3) is usually 0 to 10% by mole based on total molar of all the structural units of Resin (A).

When Resin (A) contains the structural unit derived from the monomer represented by the formula (a4-4), the content of the structural unit derived from the monomer represented by the formula (a4-4) is usually 5 to 50% by mole and preferably 10 to 45% by mole and more preferably 15 to 40% by mole based on total molar of all the structural units of Resin (A).

Preferable Resin (A) is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1). The monomer having one or more hydroxyl groups is preferably the monomer represented by the formula (a2-1), and the monomer having a lactone ring is preferably the monomer represented by the formula (a3-1) or (a3-2).

Resin (A) can be produced according to known polymerization methods such as radical polymerization.

Resin (A) usually has 2,500 or more of the weight-average molecular weight, and preferably 3,000 or more of the weight-average molecular weight. Resin (A) usually has 50,000 or less of the weight-average molecular weight, and preferably has 30,000 or less of the weight-average molecular weight. The weight-average molecular weight can be measured with gel permeation chromatography.

The content of Resin (A) in the first photoresist composition of the present invention is preferably 80% by weight or more based on 100% by weight of the solid component. In this specification, "solid component" means components other than solvent in the photoresist composition.

Next, Compound (I) will be illustrated.

In the formula (I), $R^1$ represents a hydrogen atom or a methyl group, $R^2$ represents a C6-C12 aromatic hydrocarbon group which can have one or more substituents, $R^3$ represents a cyano group or a C1-C12 hydrocarbon group which can have one or more substituents and which can contain one or more heteroatoms, $A^1$ represents a single bond, —$(CH_2)_g$—CO—O—* or —$(CH_2)_h$—O—CO—$(CH_2)_i$—CO—O—* wherein g, h and i each independently represent an integer of 1 to 6 and * represents a binding position to the nitrogen atom.

Examples of the C6-C12 aromatic hydrocarbon group include a phenyl group, a fluorenyl group, a naphthyl group and an anthryl group. Examples of the substituents of the aromatic hydrocarbon group include a C1-C4 alkyl group such as a methyl group, an ethyl group, a propyl group, an isopropyl group, a butyl group, an isobutyl group, a sec-butyl group and a tert-butyl group, a halogen atom such as a fluorine atom, a chlorine atom, a bromine atom and an iodine atom, a phenyl group, a nitro group, a cyano group, a hydroxyl group, a phenoxy group and an alkyl-substituted phenyl group such as a tert-butylphenyl group.

Specific examples of $R^2$ include the followings.

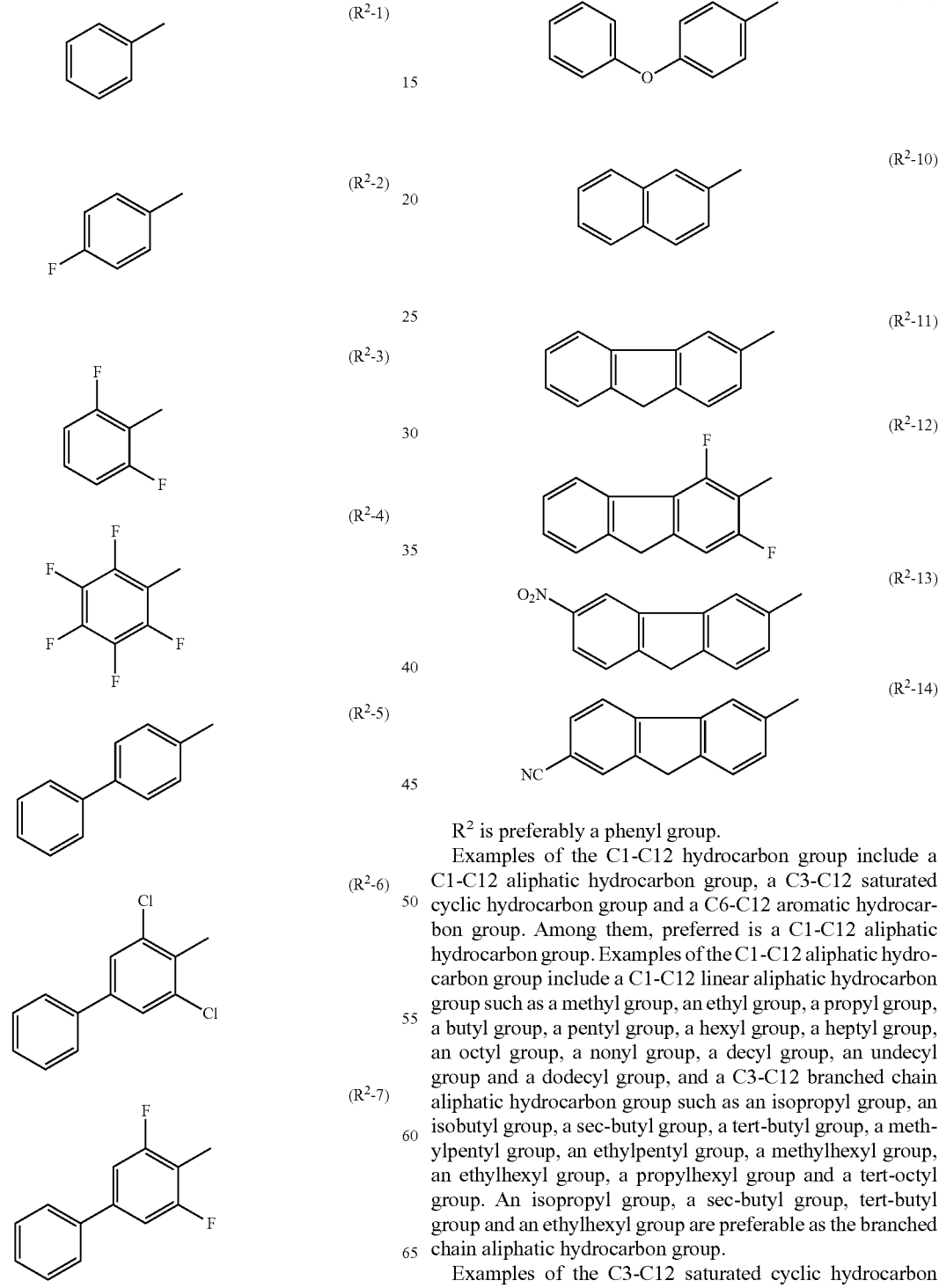

$R^2$ is preferably a phenyl group.

Examples of the C1-C12 hydrocarbon group include a C1-C12 aliphatic hydrocarbon group, a C3-C12 saturated cyclic hydrocarbon group and a C6-C12 aromatic hydrocarbon group. Among them, preferred is a C1-C12 aliphatic hydrocarbon group. Examples of the C1-C12 aliphatic hydrocarbon group include a C1-C12 linear aliphatic hydrocarbon group such as a methyl group, an ethyl group, a propyl group, a butyl group, a pentyl group, a hexyl group, a heptyl group, an octyl group, a nonyl group, a decyl group, an undecyl group and a dodecyl group, and a C3-C12 branched chain aliphatic hydrocarbon group such as an isopropyl group, an isobutyl group, a sec-butyl group, a tert-butyl group, a methylpentyl group, an ethylpentyl group, a methylhexyl group, an ethylhexyl group, a propylhexyl group and a tert-octyl group. An isopropyl group, a sec-butyl group, tert-butyl group and an ethylhexyl group are preferable as the branched chain aliphatic hydrocarbon group.

Examples of the C3-C12 saturated cyclic hydrocarbon group include the followings.

(R³-20) 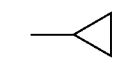

(R³-21) 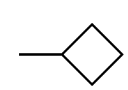

(R³-22) 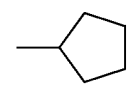

(R³-23) 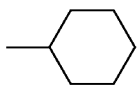

(R³-24) 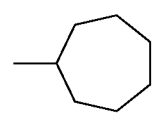

(R³-25) 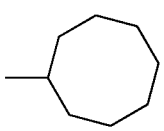

(R³-26) 

(R³-27) 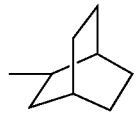

(R³-28) 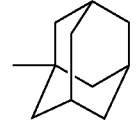

(R³-29) 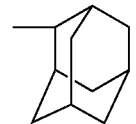

Examples of the C6-C12 aromatic hydrocarbon group include the same as described above.

Examples of the substituents of the C1-C12 hydrocarbon group include a halogen atom such as a fluorine atom, a chlorine atom, a bromine atom and an iodine atom, a nitro group, a cyano group and a hydroxyl group, and a halogen atom is preferable.

$R^3$ is preferably a cyano group, a C1-C12 aliphatic hydrocarbon group or a C1-C12 halogenated aliphatic hydrocarbon group.

The C1-C12 hydrocarbon group can contain one or more heteroatoms such as an oxygen atom and a sulfur atom, and can contain —$SO_2$— or —$CO_2$— as a connecting group.

Examples of $R^3$ include the followings.

—$CF_3$ (R³-1)

—CN (R³-2)

—$CH_3$ (R³-3)

—$CF_2CH_3$ (R³-4)

—$CF_2CF_3$ (R³-5)

—$CF_2CF_2CF_3$ (R³-6)

—$CF_2C_2H_3$ (R³-7)

—$CF_2CF_2CF_2$—$CO_2$—$CH_3$ (R³-8)

(R³-9)
$$-CF_2-\overset{O}{\underset{O}{S}}-C_2H_5$$

(R³-10)
$$-CF_2-\overset{O}{\underset{O}{S}}-CF_2CF_3$$

(R³-11) 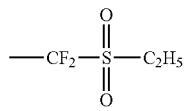

(R³-12) 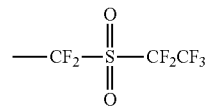

(R³-13) 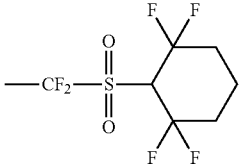

(R³-14) 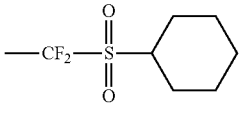

(R³-15) 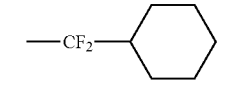

(R³-16) 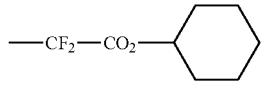

(R³-17) 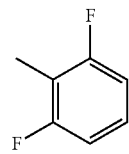

-continued

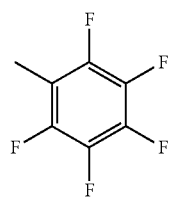
(R³-18)

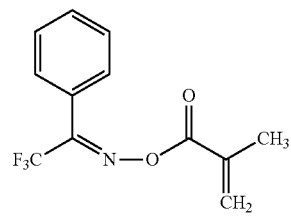
(I-1)

Examples of $A^1$ include the followings, and in the followings, ($A^1$-1) means a single bond.

(A¹-1) —

(A¹-2)

(A¹-3)

(A¹-4)

(A¹-5)

(A¹-6)

(A¹-7)

(A¹-8)

(A¹-9)

(A¹-10)

Specific examples of Compound (I) include the following Compound (I-1) to Compound (I-80) shown in Tables 1 to 3. For example, Compound (I-1) in Table 1 is a compound represented by the following formula:

TABLE 1

| Compound (I) | $A^1$ | $R^1$ | $R^2$ | $R^3$ |
|---|---|---|---|---|
| I-1 | $A^1$-1 | $CH_3$ | $R^2$-1 | $R^3$-1 |
| I-2 | $A^1$-1 | $CH_3$ | $R^2$-1 | $R^3$-3 |
| I-3 | $A^1$-1 | $CH_3$ | $R^2$-1 | $R^3$-5 |
| I-4 | $A^1$-1 | $CH_3$ | $R^2$-1 | $R^3$-13 |
| I-5 | $A^1$-1 | $CH_3$ | $R^2$-1 | $R^3$-17 |
| I-6 | $A^1$-1 | $CH_3$ | $R^2$-1 | $R^3$-18 |
| I-7 | $A^1$-1 | $CH_3$ | $R^2$-1 | $R^3$-22 |
| I-8 | $A^1$-1 | $CH_3$ | $R^2$-1 | $R^3$-23 |
| I-9 | $A^1$-1 | $CH_3$ | $R^2$-1 | $R^3$-28 |
| I-10 | $A^1$-1 | $CH_3$ | $R^2$-1 | $R^3$-29 |
| I-11 | $A^1$-1 | $CH_3$ | $R^2$-3 | $R^3$-4 |
| I-12 | $A^1$-1 | $CH_3$ | $R^2$-3 | $R^3$-5 |
| I-13 | $A^1$-1 | $CH_3$ | $R^2$-4 | $R^3$-6 |
| I-14 | $A^1$-1 | $CH_3$ | $R^2$-4 | $R^3$-7 |
| I-15 | $A^1$-1 | $CH_3$ | $R^2$-5 | $R^3$-8 |
| I-16 | $A^1$-1 | $CH_3$ | $R^2$-5 | $R^3$-9 |
| I-17 | $A^1$-1 | $CH_3$ | $R^2$-5 | $R^3$-10 |
| I-18 | $A^1$-1 | $CH_3$ | $R^2$-5 | $R^3$-11 |
| I-19 | $A^1$-1 | $CH_3$ | $R^2$-6 | $R^3$-12 |
| I-20 | $A^1$-1 | $CH_3$ | $R^2$-6 | $R^3$-14 |
| I-21 | $A^1$-1 | $CH_3$ | $R^2$-6 | $R^3$-15 |
| I-22 | $A^1$-1 | $CH_3$ | $R^2$-6 | $R^3$-16 |
| I-23 | $A^1$-1 | $CH_3$ | $R^2$-7 | $R^3$-17 |
| I-24 | $A^1$-1 | $CH_3$ | $R^2$-8 | $R^3$-17 |
| I-25 | $A^1$-1 | $CH_3$ | $R^2$-9 | $R^3$-17 |
| I-26 | $A^1$-1 | $CH_3$ | $R^2$-10 | $R^3$-1 |
| I-27 | $A^1$-1 | $CH_3$ | $R^2$-10 | $R^3$-2 |
| I-28 | $A^1$-1 | $CH_3$ | $R^2$-10 | $R^3$-3 |
| I-29 | $A^1$-1 | $CH_3$ | $R^2$-11 | $R^3$-1 |
| I-30 | $A^1$-1 | $CH_3$ | $R^2$-11 | $R^3$-2 |

TABLE 2

| Compound (I) | $A^1$ | $R^1$ | $R^2$ | $R^3$ |
|---|---|---|---|---|
| I-31 | $A^1$-1 | $CH_3$ | $R^2$-11 | $R^3$-3 |
| I-32 | $A^1$-1 | $CH_3$ | $R^2$-11 | $R^3$-12 |
| I-33 | $A^1$-1 | $CH_3$ | $R^2$-11 | $R^3$-13 |
| I-34 | $A^1$-1 | $CH_3$ | $R^2$-11 | $R^3$-14 |
| I-35 | $A^1$-1 | $CH_3$ | $R^2$-12 | $R^3$-14 |
| I-36 | $A^1$-1 | $CH_3$ | $R^2$-13 | $R^3$-14 |
| I-37 | $A^1$-1 | $CH_3$ | $R^2$-14 | $R^3$-14 |
| I-38 | $A^1$-1 | $CH_3$ | $R^2$-1 | $R^3$-1 |
| I-39 | $A^1$-1 | $CH_3$ | $R^2$-1 | $R^3$-13 |
| I-40 | $A^1$-2 | $CH_3$ | $R^2$-1 | $R^3$-2 |
| I-41 | $A^1$-2 | $CH_3$ | $R^2$-1 | $R^3$-1 |
| I-42 | $A^1$-2 | $CH_3$ | $R^2$-1 | $R^3$-2 |
| I-43 | $A^1$-2 | $CH_3$ | $R^2$-1 | $R^3$-3 |
| I-44 | $A^1$-2 | $CH_3$ | $R^2$-1 | $R^3$-13 |
| I-45 | $A^1$-2 | $CH_3$ | $R^2$-1 | $R^3$-17 |
| I-46 | $A^1$-2 | $CH_3$ | $R^2$-1 | $R^3$-18 |
| I-47 | $A^1$-2 | $CH_3$ | $R^2$-3 | $R^3$-4 |
| I-48 | $A^1$-3 | $CH_3$ | $R^2$-3 | $R^3$-5 |
| I-49 | $A^1$-3 | $CH_3$ | $R^2$-4 | $R^3$-6 |
| I-50 | $A^1$-3 | $CH_3$ | $R^2$-4 | $R^3$-7 |
| I-51 | $A^1$-4 | $CH_3$ | $R^2$-5 | $R^3$-8 |
| I-52 | $A^1$-4 | $CH_3$ | $R^2$-5 | $R^3$-9 |
| I-53 | $A^1$-4 | $CH_3$ | $R^2$-5 | $R^3$-10 |
| I-54 | $A^1$-5 | $CH_3$ | $R^2$-5 | $R^3$-11 |
| I-55 | $A^1$-5 | $CH_3$ | $R^2$-6 | $R^3$-12 |

TABLE 2-continued

| Compound (I) | A¹ | R¹ | R² | R³ |
|---|---|---|---|---|
| I-56 | A¹-5 | CH₃ | R²-6 | R³-14 |
| I-57 | A¹-6 | CH₃ | R²-6 | R³-15 |
| I-58 | A¹-6 | CH₃ | R²-6 | R³-16 |
| I-59 | A¹-6 | CH₃ | R²-7 | R³-17 |
| I-60 | A¹-7 | CH₃ | R²-8 | R³-17 |

TABLE 3

| Compound (I) | A¹ | R¹ | R² | R³ |
|---|---|---|---|---|
| I-61 | A¹-7 | CH₃ | R²-9 | R³-17 |
| I-62 | A¹-1 | H | R²-10 | R³-1 |
| I-63 | A¹-1 | H | R²-10 | R³-2 |
| I-64 | A¹-1 | H | R²-10 | R³-3 |
| I-65 | A¹-1 | H | R²-11 | R³-1 |
| I-66 | A¹-1 | H | R²-11 | R³-2 |
| I-67 | A¹-1 | H | R²-11 | R³-3 |
| I-68 | A¹-1 | H | R²-11 | R³-12 |
| I-69 | A¹-1 | H | R²-11 | R³-13 |
| I-70 | A¹-1 | CH₃ | R²-1 | R³-6 |
| I-71 | A¹-8 | CH₃ | R²-1 | R³-1 |
| I-72 | A¹-8 | CH₃ | R²-1 | R³-6 |
| I-73 | A¹-8 | CH₃ | R²-2 | R³-1 |
| I-74 | A¹-8 | CH₃ | R²-10 | R³-1 |
| I-75 | A¹-9 | CH₃ | R²-1 | R³-1 |
| I-76 | A¹-9 | CH₃ | R²-1 | R³-6 |
| I-77 | A¹-9 | CH₃ | R²-4 | R³-1 |
| I-78 | A¹-10 | CH₃ | R²-1 | R³-1 |
| I-79 | A¹-10 | CH₃ | R²-1 | R³-6 |
| I-80 | A¹-10 | CH₃ | R²-3 | R³-1 |

Compound (I) can be produced, for example, by reacting a compound represented by the formula (I-a):

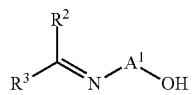

(I-a)

wherein $R^2$, $R^3$ and $A^1$ are the same as defined above, with a compound represented by the formula (I-b):

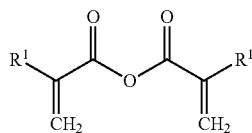

(I-b)

wherein $R^1$ is the same as defined above.

The polymer comprising a structural unit derived from Compound (I) (hereinafter, simply referred to as Polymer (II)) can be produce, for example, by polymerizing Compound (I) or by polymerizing Compound (I) with other monomers in the presence of an initiator in an inert solvent such as 1,4-dioxane, tetrahydrofuran, acetonitrile and dichloromethane to obtain a mixture containing Polymer (II), followed by mixing the obtained mixture with a polar solvent such as water and methanol or a non-polar solvent such as hexane and heptane to cause precipitation and then, isolating the precipitated Polymer (II). Examples of the initiator include 2,2'-azobisisobutyronitrile, 2,2'-azobis(2,4-dimethylvaleronitrile) and benzoyl peroxide. The polymerization temperature is usually room temperature to 100° C., and preferably 60 to 80° C.

The content of the structural unit derived from Compound (I) in Polymer (II) is usually 1 to 100% by mole based on 100% by mole of all the structural units of Polymer (II), preferably 10 to 100% by mole and more preferably 20 to 100% by mole.

Polymer (II) may be homopolymer of Compound (I), and may be copolymer of Compound (I) and at least one monomer having the different structure from Compound (I).

When Polymer (II) is a copolymer of Compound (I) and at least one monomer having the different structure from Compound (I), the content of the structural unit(s) derived from the monomer(s) having the different structure from Compound (I) is usually 1 to 95% by mole based on 100% by mole of all the structural units of Polymer (II), preferably 10 to 90% by mole and more preferably 20 to 80% by mole.

Examples of the monomer having the different structure from Compound (I) include the monomers used for preparing the above-mentioned Resin (A) and a monomer represented by the formula (L):

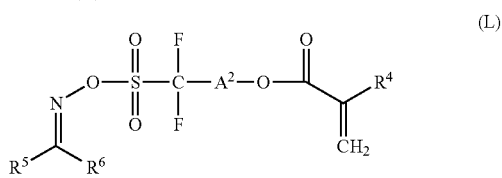

(L)

wherein $R^4$ represents a hydrogen atom or a methyl group, $R^5$ represents a C6-C12 aromatic hydrocarbon group which can have one or more substituents, $R^6$ represents a C1-C12 hydrocarbon group which can have one or more substituents and which can contain one or more heteroatoms, $A^2$ represents a single bond, —CO—O—(CH₂)ₑ—*, —O—(CH₂)ₑ—* or —O—CO—(CH₂)ₑ—* wherein e represents an integer of 1 to 8 and * represents a binding position to —CF₂—.

Examples of $R^5$ include the same as described in $R^2$ and examples of $R^6$ include the same as described in $R^3$.

Examples of the monomer represented by the formula (L) include the following compound (L1) to (L20) shown in Table 4. In Table 4, "A²-1" means —CO—O—(CH₂)ₑ—*, "A²-2" means —O—(CH₂)ₑ—* and "A²-3" means —O—CO—(CH₂)ₑ—*.

TABLE 4

| monomer represented by the formula (L) | R⁴ | R⁵ | R⁶ | A² | e |
|---|---|---|---|---|---|
| L1 | CH₃ | R²-1 | R³-1 | A²-1 | 2 |
| L2 | CH₃ | R²-1 | R³-2 | A²-1 | 2 |
| L3 | CH₃ | R²-1 | R³-3 | A²-1 | 2 |
| L4 | CH₃ | R²-1 | R³-13 | A²-1 | 2 |
| L5 | CH₃ | R²-1 | R³-17 | A²-1 | 2 |
| L6 | H | R²-1 | R³-18 | A²-1 | 2 |
| L7 | CH₃ | R²-1 | R³-22 | A²-1 | 2 |
| L8 | H | R²-1 | R³-23 | A²-1 | 2 |
| L9 | CH₃ | R²-1 | R³-28 | A²-2 | 3 |
| L10 | CH₃ | R²-1 | R³-1 | A²-2 | 4 |
| L11 | CH₃ | R²-3 | R³-4 | A²-1 | 4 |
| L12 | CH₃ | R²-3 | R³-5 | A²-1 | 4 |
| L13 | H | R²-4 | R³-6 | A²-3 | 5 |
| L14 | CH₃ | R²-4 | R³-7 | A²-3 | 5 |
| L15 | CH₃ | R²-1 | R³-1 | A²-1 | 5 |
| L16 | CH₃ | R²-5 | R³-9 | A²-1 | 6 |
| L17 | CH₃ | R²-5 | R³-10 | A²-1 | 7 |
| L18 | CH₃ | R²-5 | R³-11 | A²-1 | 8 |
| L19 | CH₃ | R²-6 | R³-12 | A²-1 | 8 |
| L20 | CH₃ | R²-6 | R³-14 | A²-1 | 8 |

Among them, preferred is a monomer (L1).

When Polymer (II) contains the structural unit derived from the monomer represented by the formula (L), the content thereof is usually 1 to 99% by mole based on 100% by mole of all the structural units of Polymer (II), preferably 10 to 90% by mole and more preferably 50 to 80% by mole.

Among the monomer (s) having the different structure from Compound (I), preferred are a monomer (L1) and α-methacryloyloxy-γ-butyrolactone.

The first photoresist composition of the present invention can contain two or more kinds of Polymer (II). The content of Polymer (II) is usually 0.1 to 5% by weight based on amount of solid component.

The first photoresist composition of the present invention contains one or more acid generators, and preferably a photoacid generator.

The acid generator is a substance which is decomposed to generate an acid by applying a radiation such as a light, an electron beam or the like on the substance itself or on a photoresist composition containing the substance. The acid generated from the acid generator acts on Resin (A) resulting in cleavage of the acid-labile group existing in Resin (A).

Examples of the acid generator include a nonionic acid generator, an ionic acid generator and the combination thereof. An ionic acid generator is preferable. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and DNQ 4-sulfonate. Examples of the ionic acid generator include an acid generator having an inorganic anion such as $BF_4^-$, $PF_6^-$, $AsF_6^-$ and $SbF_6^-$, and an acid generator having an organic anion such as a sulfonic acid anion and a bissulfonylimido anion, and an acid generator having a sulfonic acid anion is preferable. Preferable examples of the acid generator include a salt represented by the formula (B1):

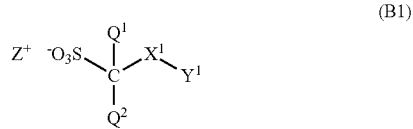

(B1)

wherein $Q^1$ and $Q^2$ each independently represent a fluorine atom or a C1-C6 perfluoroalkyl group, $X^1$ represents a single bond or a C1-C17 divalent saturated hydrocarbon group in which one or more —CH$_2$— can be replaced by —O— or —CO—, $Y^1$ represents a C1-C36 aliphatic hydrocarbon group which can have one or more substituents, a C3-C36 saturated cyclic hydrocarbon group which can have one or more substituents, or a C6-C36 aromatic hydrocarbon group which can have one or more substituents, and one or more —CH$_2$— in the aliphatic hydrocarbon group and the saturated cyclic hydrocarbon group can be replaced by —O— or —CO—, and $Z^+$ represents an organic counter cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 divalent saturated hydrocarbon group include a C1-C17 linear alkylene group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a C1-C17 branched alkylene group such as a 1-methyl-1,3-propylene group, a 2-methyl-1,3-propylene group, a 2-methyl-1,2-propylene group, a 1-methyl-1,4-butylene group, and a 2-methyl-1,4-butylene group, a divalent saturated monocyclic hydrocarbon group such as a cycloalkylene group such as a 1,3-cyclobutylene group, a 1,3-cyclopentylene group, a 1,4-cyclohexylene group, and a 1,5-cyclooctylene group, and a divalent saturated polycyclic hydrocarbon group such as a 1,4-norbornylene group, a 2,5-norbornylene group, a 1,5-adamantylene group and a 2,6-adamantylene group.

The C1-C17 divalent saturated hydrocarbon group can have one or more substituents, and examples of the substituent include a halogen atom, a hydroxyl group, a carboxyl group, a C6-C18 aromatic group, a C7-C21 aralkyl group such as a benzyl group, a phenethyl group, a phenylpropyl group, a trityl group, a naphthylmethyl group and a naphthyethyl group, a C2-C4 acyl group and a glycidyloxy group.

Examples of the C1-C17 saturated hydrocarbon group in which one or more methylene groups are replaced by —O— or —CO— include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 alkanediyl group, $L^{b3}$ represents a single bond or a C1-C12 alkanediyl group, $L^{b4}$ represents a single bond or a C1-C13 alkanediyl group, with proviso that total carbon number of $L^{b3}$ and $L^{b4}$ is 1 to 13, $L^{b5}$ represents a C1-C15 alkanediyl group, $L^{b6}$ represents a C1-C15 alkanediyl group, $L^{b9}$ represents a C1-C15 alkanediyl group, with proviso that total carbon number of $L^{b6}$ and $L^{b7}$ is 1 to 16, $L^{b8}$ represents a C1-C14 alkanediyl group, $L^{b9}$ represents a C1-C11 alkanediyl group, $L^{b10}$ represents a C1-C11 alkanediyl group, with proviso that total carbon number of $L^{b9}$ and $L^{b10}$ is 1 to 12, and * represents a binding position to —C($Q^1$)($Q^2$)-. Among them, preferred are *—CO—O-$L^{b2}$-, *—CO—O-$L^{b4}$-CO—O-$L^{b3}$-, *-$L^{b5}$-O—CO— and *-$L^{b7}$-O-$L^{b6}$-, and more preferred are *—CO—O-$L^{b2}$- and *—CO—O-$L^{b4}$-CO—O-$L^{b3}$-, and much more preferred is *—CO—O-$L^{b2}$-, and especially preferred is *—CO—O-$L^{b2}$- in which $L^{b2}$ is a single bond or —CH$_2$—.

Examples of *—CO—O-$L^{b2}$- include *—CO—O— and *—CO—O—CH$_2$—. Examples of *—CO—O-$L^{b4}$-CO—O-$L^{b3}$- include *—CO—O—CH$_2$—CO—O—, *—CO—O—(CH$_2$)$_2$—CO—O—, *—CO—O—(CH$_2$)$_3$—CO—O—, *—CO—O—(CH$_2$)$_4$—CO—O—, *—CO—O—(CH$_2$)$_6$—CO—O—, *—CO—O—(CH$_2$)$_8$—CO—O—, *—CO—O—CH$_2$—CH(CH$_3$)—CO—O— and *—CO—O—CH$_2$—C(CH$_3$)$_2$—CO—O—. Examples of *-$L^{b5}$-O—CO— include *—CH$_2$—O—CO—, *—(CH$_2$)$_2$—O—CO—, *—(CH$_2$)$_3$—O—CO—, *—(CH$_2$)$_4$—O—CO—, *—(CH$_2$)$_6$—O—CO— and *—(CH$_2$)$_8$—O—CO—. Examples of *$L^{b7}$-O-$L^{b6}$- include *—CH$_2$—O—CH$_2$—. Examples of *—CO—O-$L^{b8}$-O— include *—CO—O—CH$_2$—O—, *—CO—O—(CH$_2$)$_2$—O—, *—CO—O—(CH$_2$)$_3$—O—, *—CO—O—(CH$_2$)$_4$—O— and *—CO—O—(CH$_2$)$_6$—O—. Examples of *—CO—O-$L^{b10}$-O-$L^{b9}$-CO—O— include the followings.

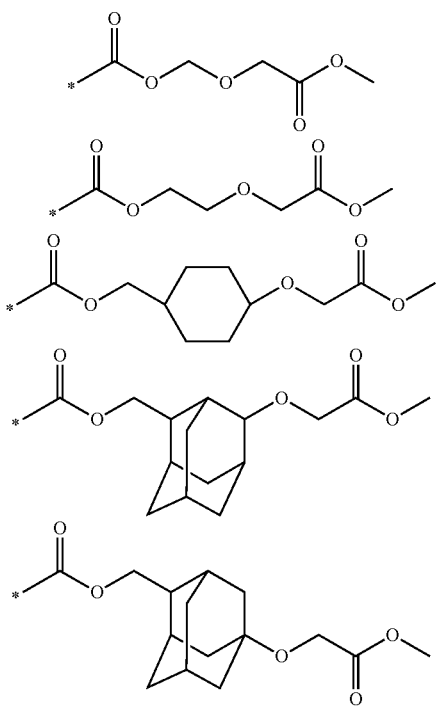

The saturated hydrocarbon group can have one or more substituents, and examples of the substituent include a halogen atom, a hydroxyl group, a carboxyl group, a C6-C18 aromatic hydrocarbon group, a C7-C21 aralkyl group such as a benzyl group, a phenethyl group, a phenylpropyl group, a trityl group, a naphthylmethyl group and a naphthyethyl group, a C2-C4 acyl group and a glycidyloxy group.

Examples of the substituent in $Y^1$ include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and $—(CH_2)_{j2}—O—CO—R^{b1}—$ in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a-1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 saturated cyclic hydrocarbon group represented by $Y^1$ include the groups represented by the formulae (Y1) to (Y26):

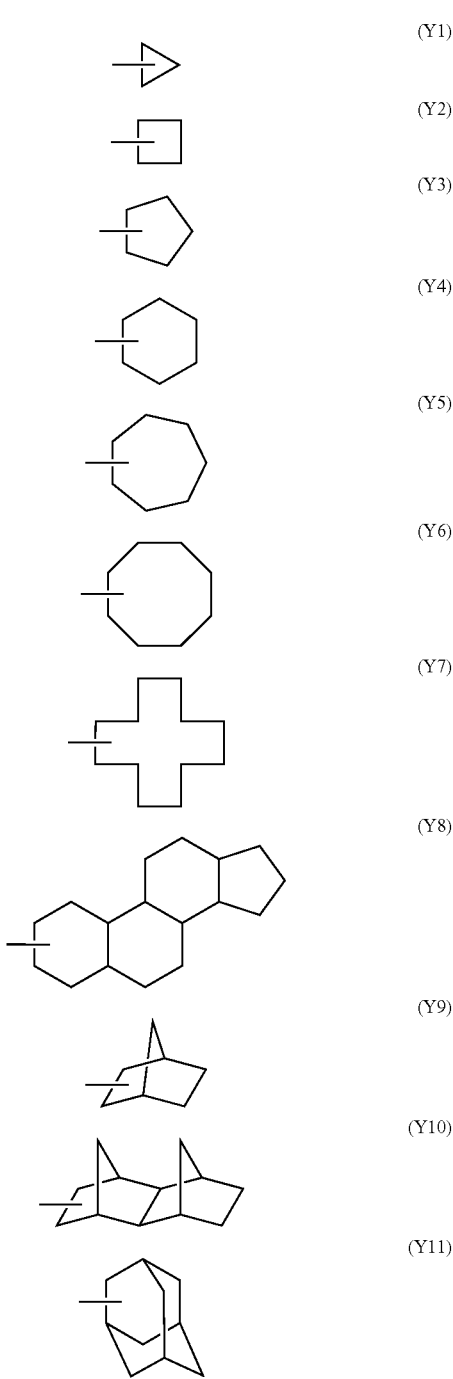

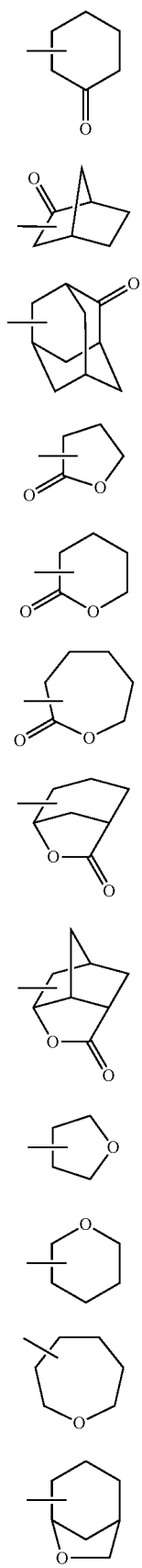
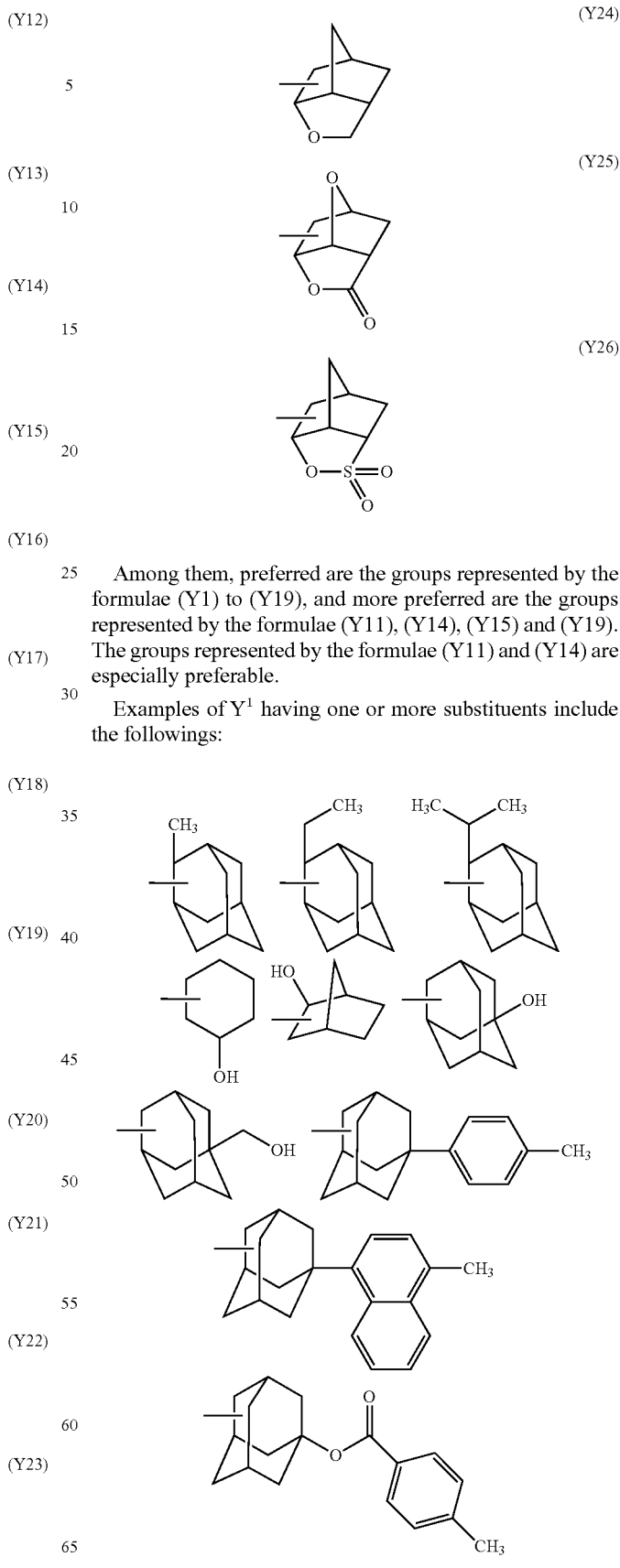
Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.
Examples of $Y^1$ having one or more substituents include the followings:

$Y^1$ is preferably an adamantyl group which can have one or more substituents, and is more preferably an adamantyl group or an oxoadamantyl group.

Among the sulfonic acid anions of the acid generator represented by the formula (B1), preferred is a sulfonic acid anion having the group represented by *—CO—O-$L^{b2}$-, and more preferred are anions represented by the formulae (b1-1-1) to (b1-1-9).

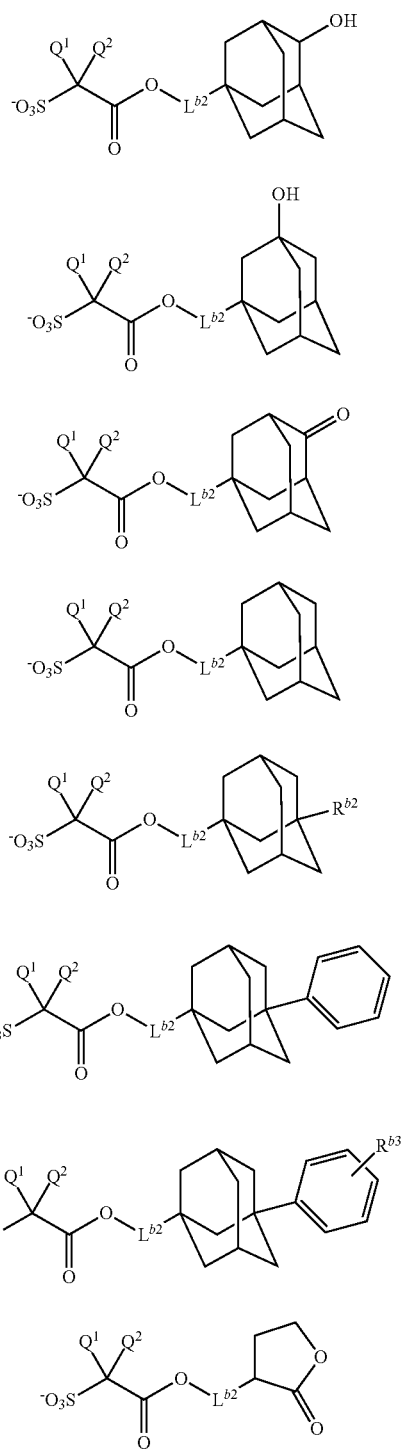

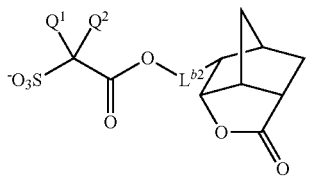

wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

Specific examples of the sulfonic acid anion include the followings.

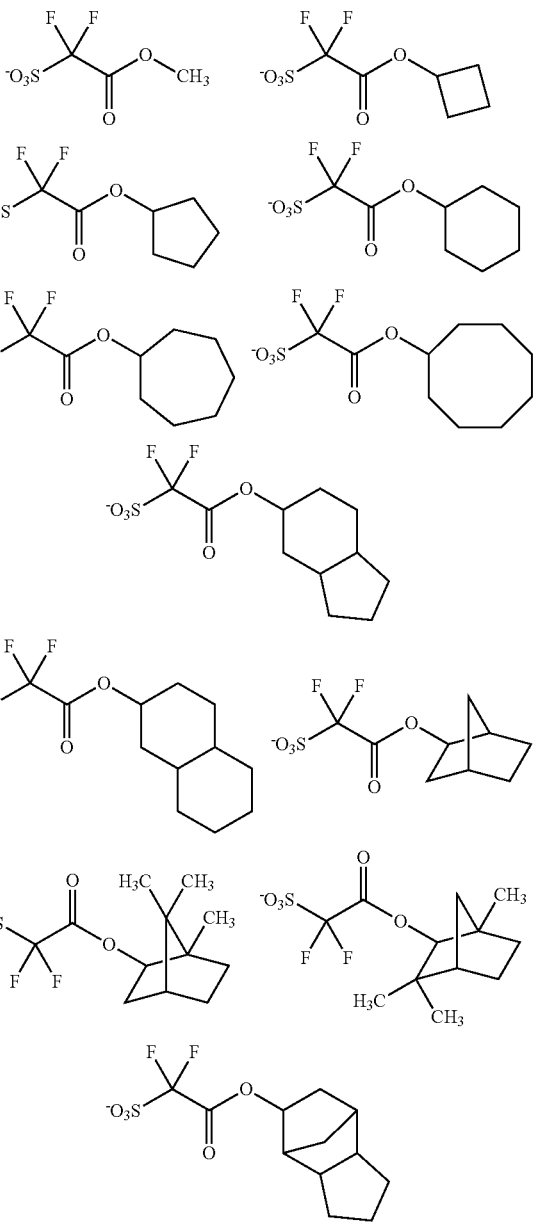

-continued
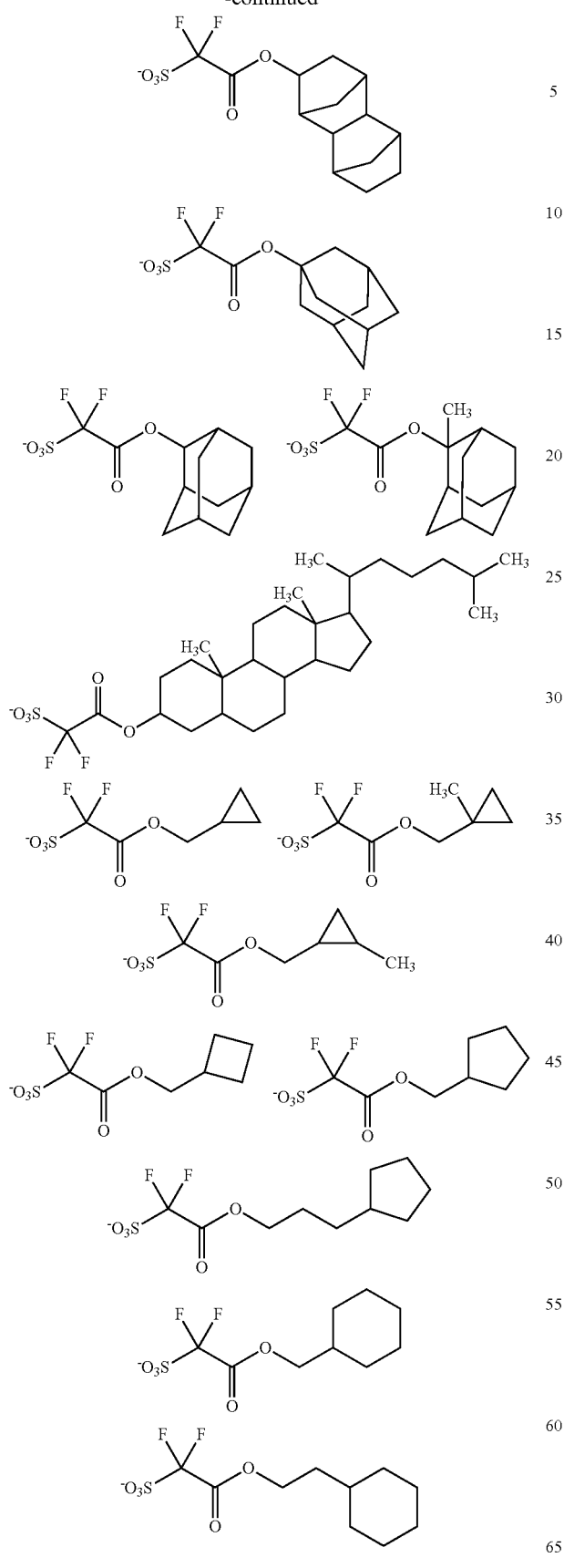
-continued
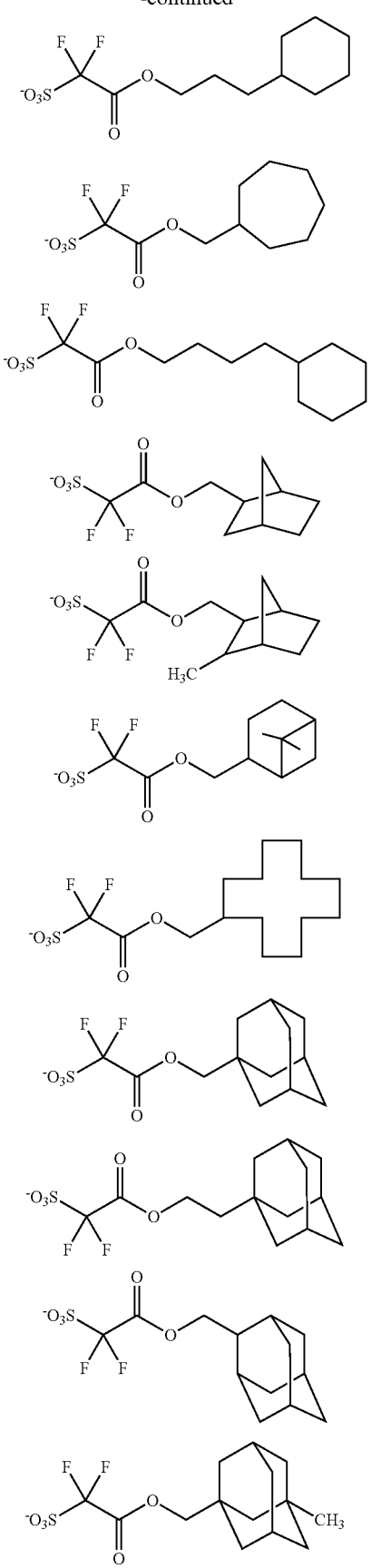

| 77 | 78 |
|---|---|
| -continued | -continued |
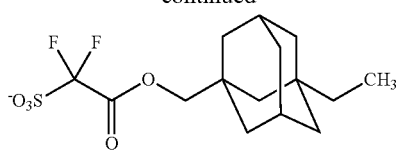
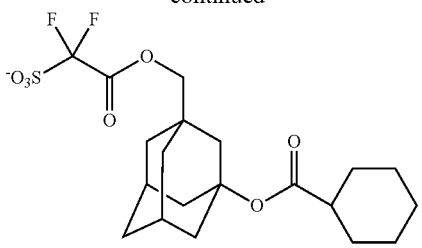
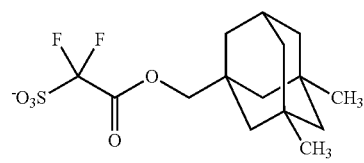
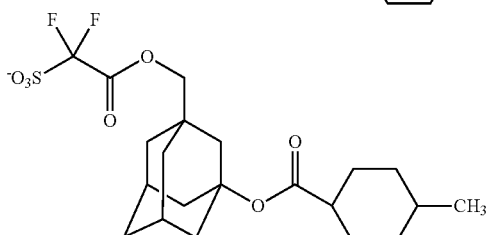
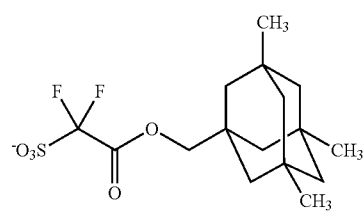
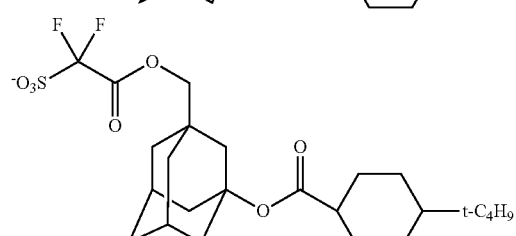
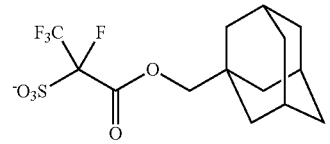
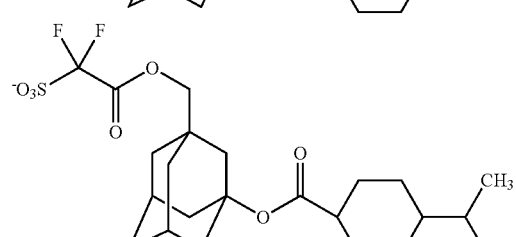
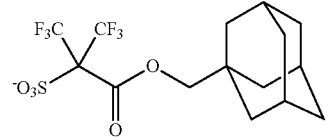
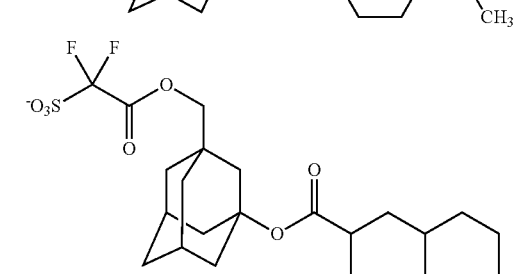
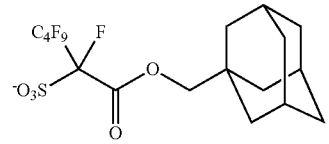
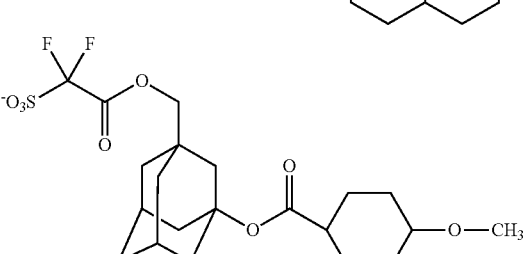
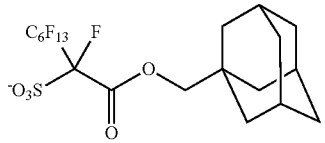
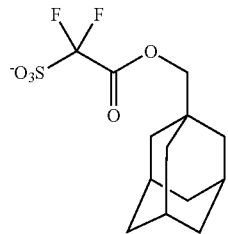
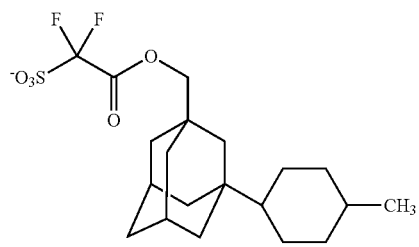
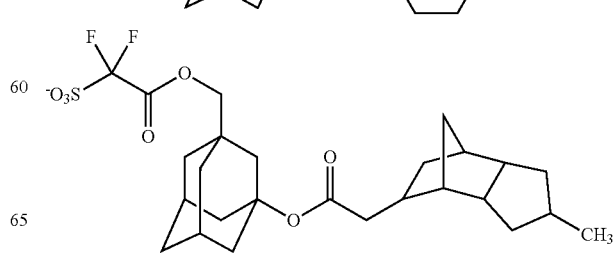
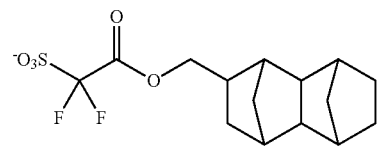

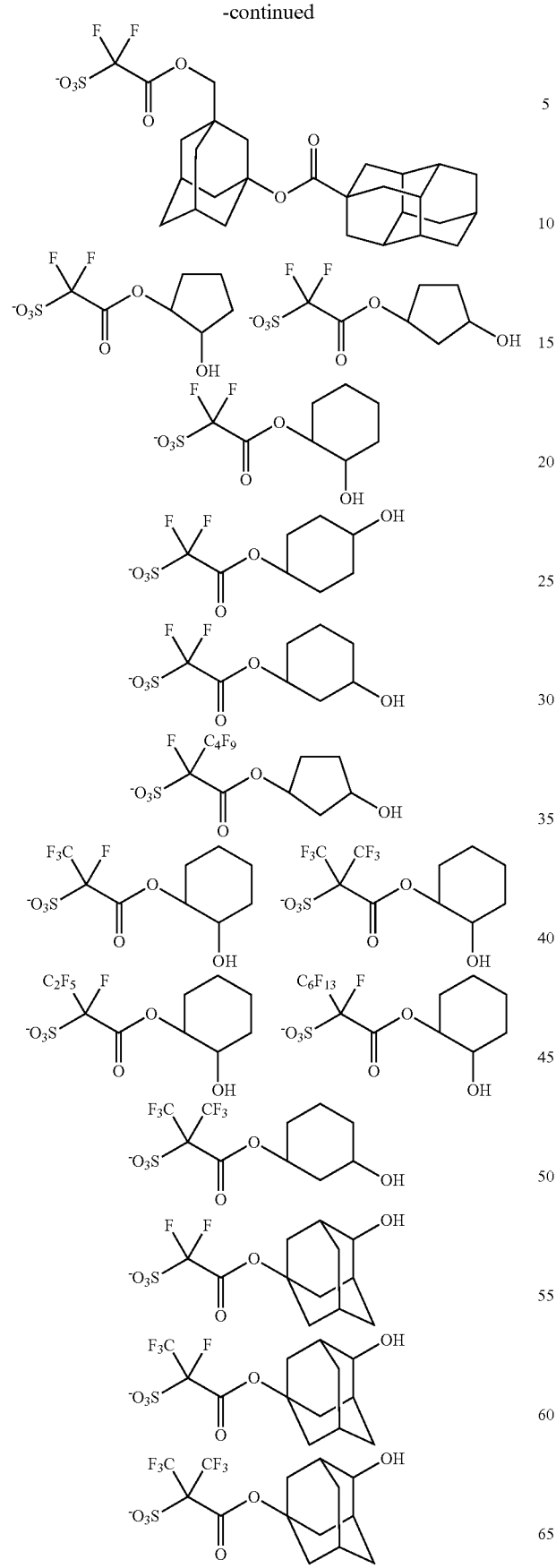
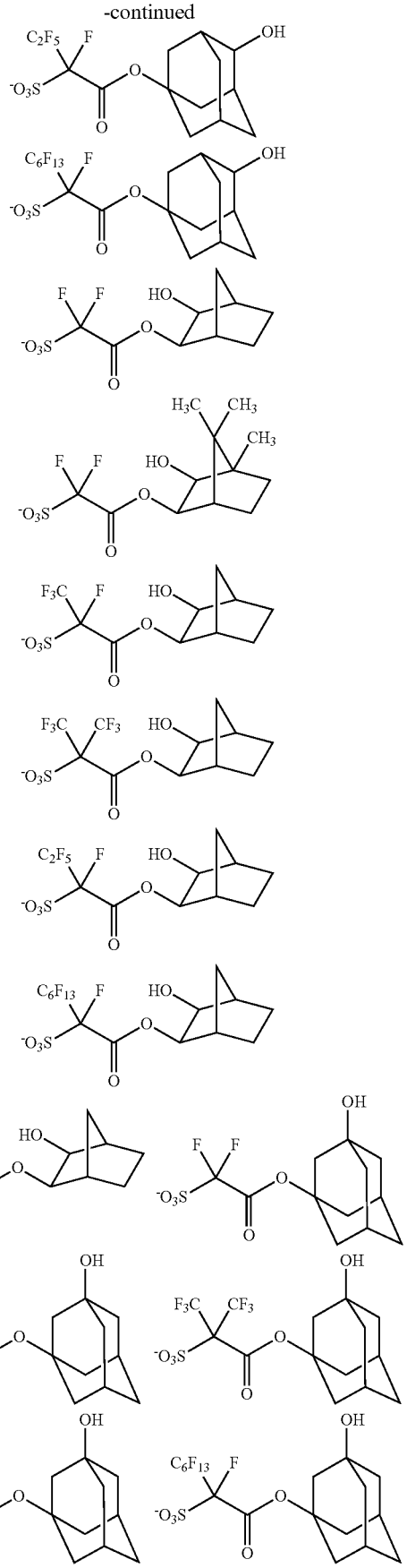

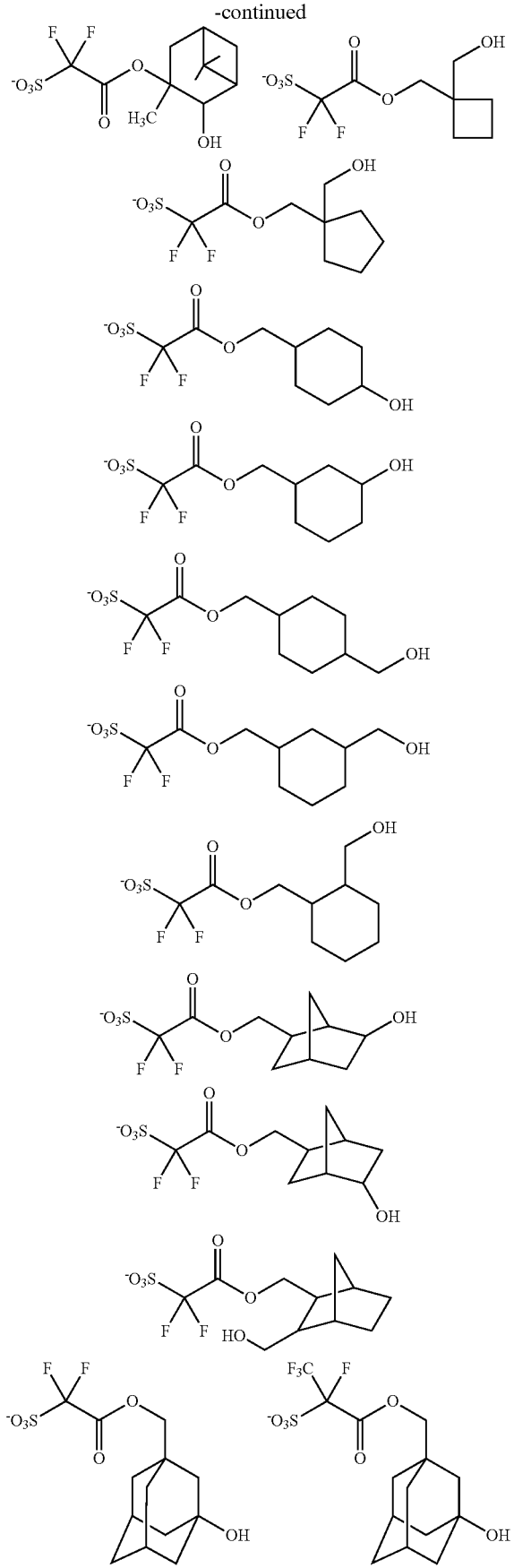
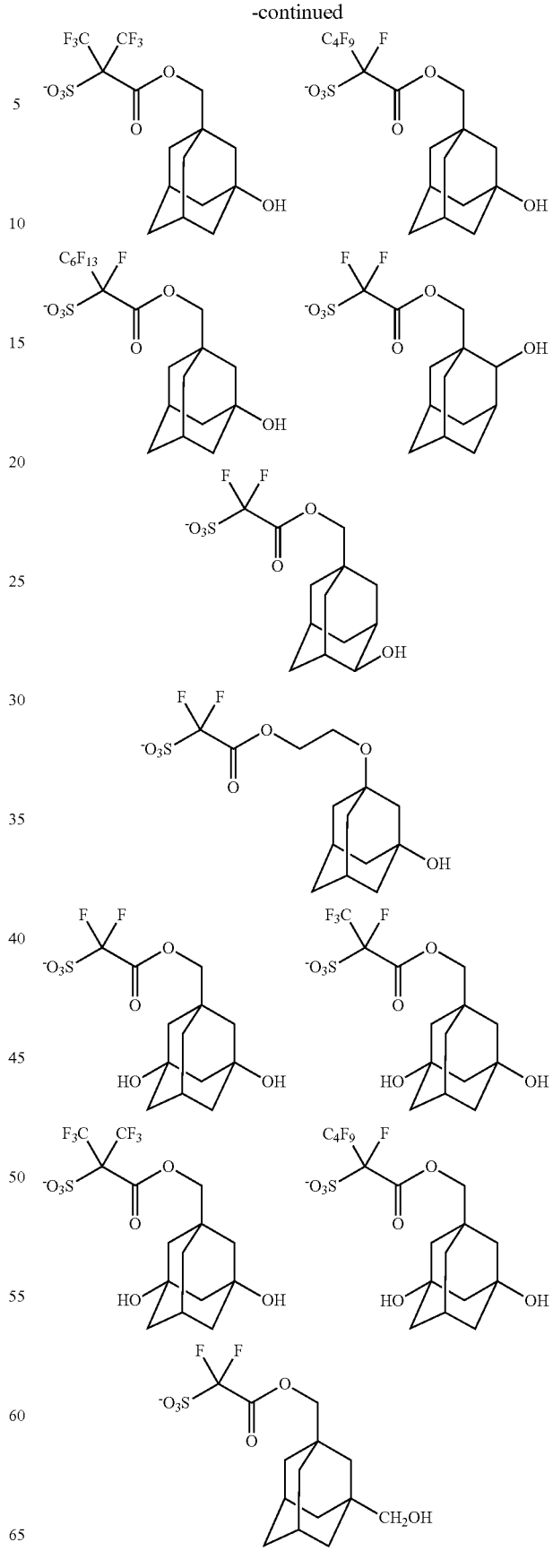

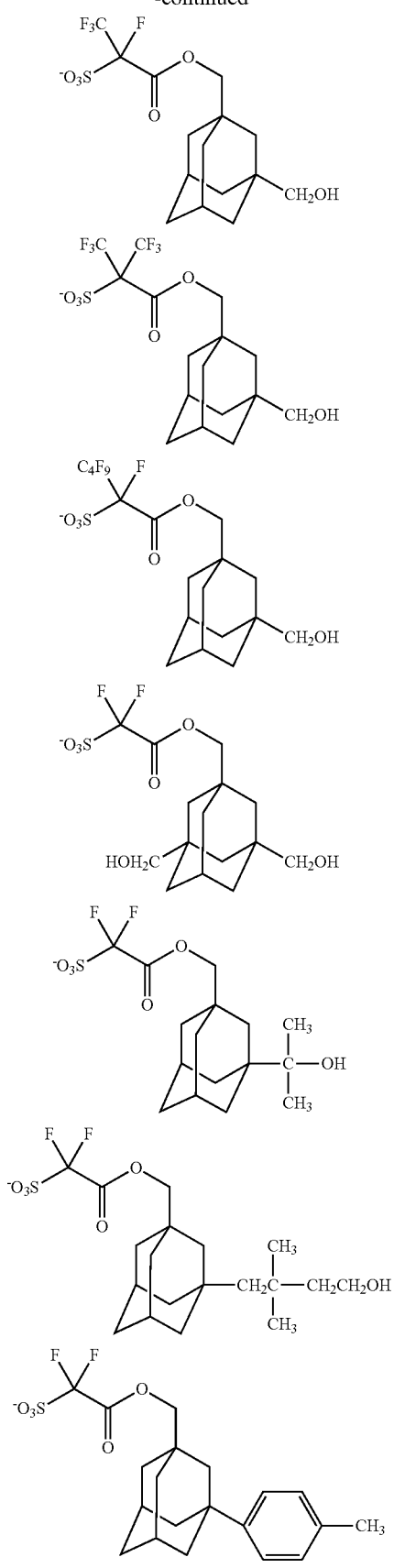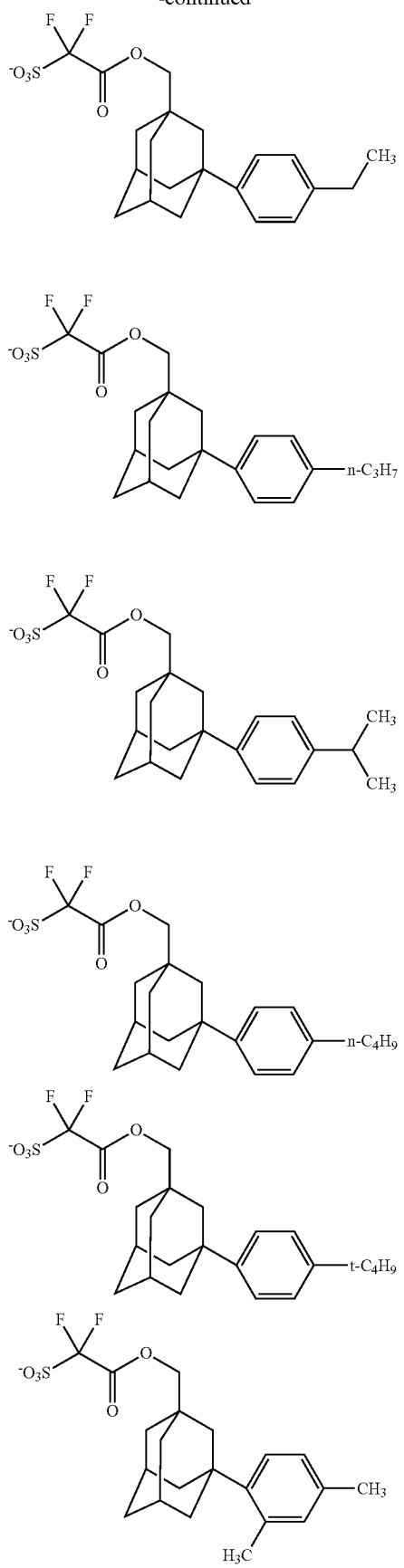

85
-continued
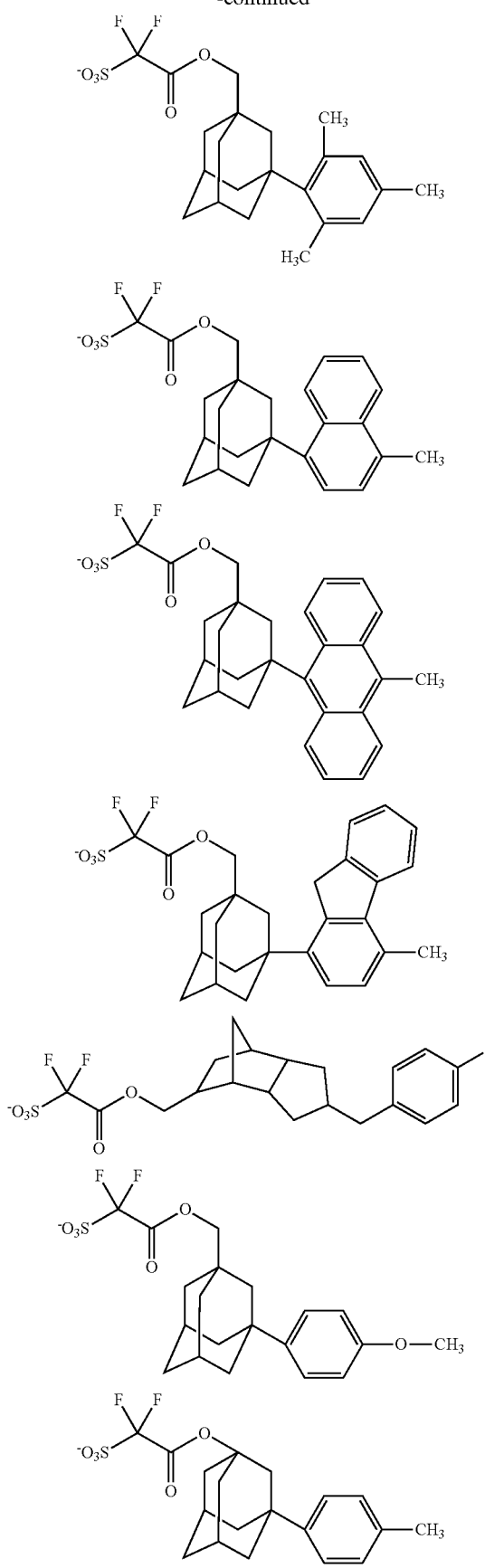
86
-continued
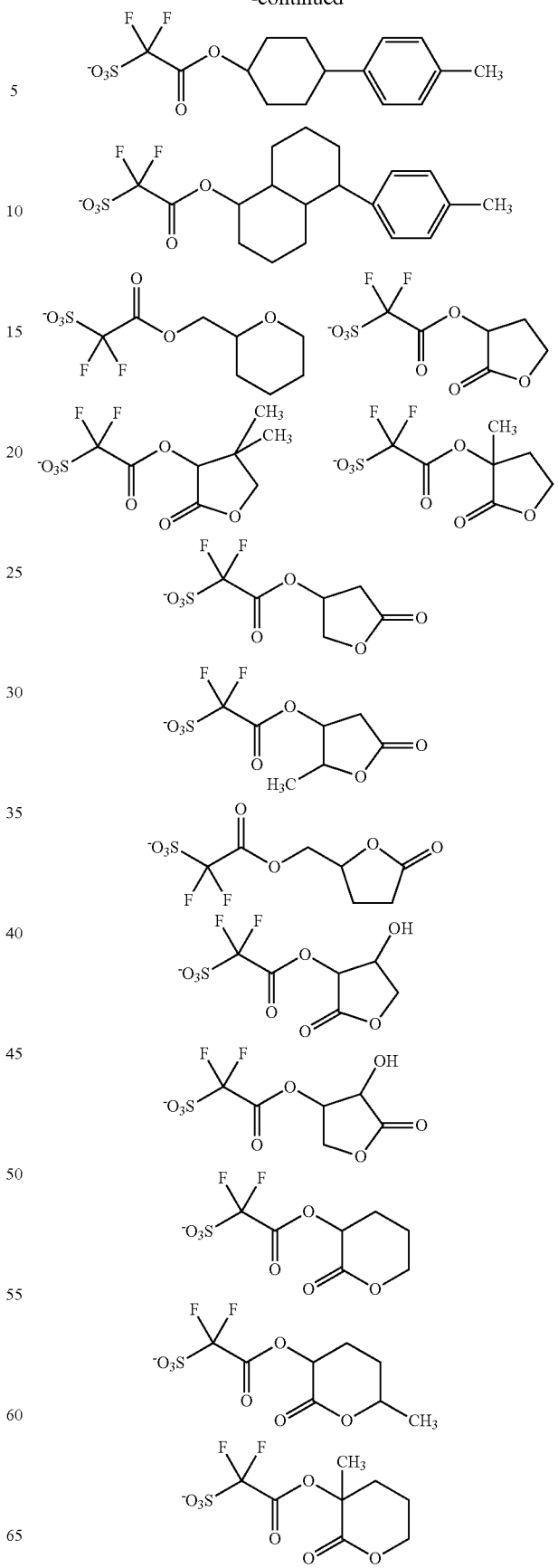

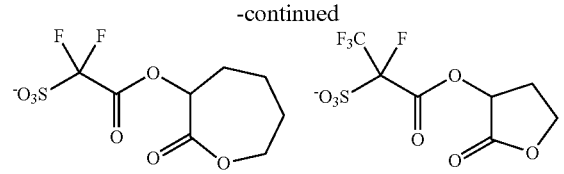
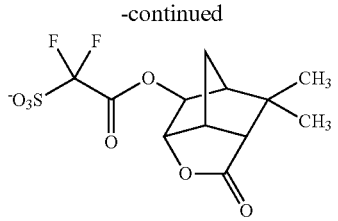
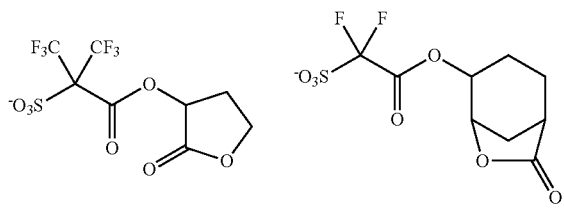
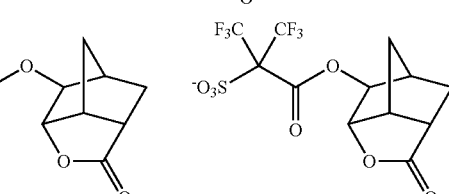
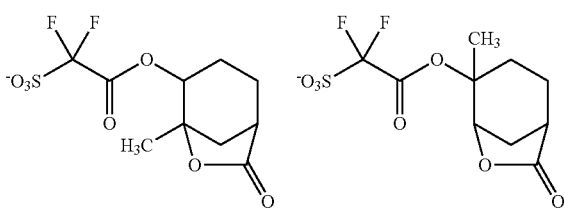
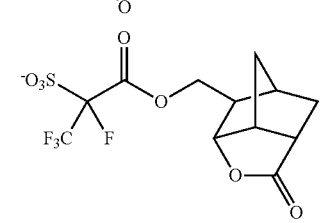
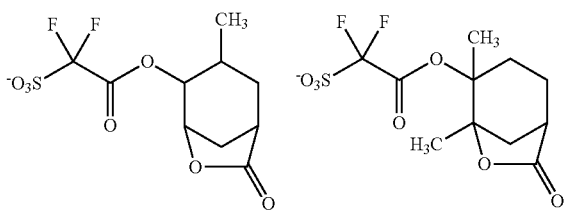
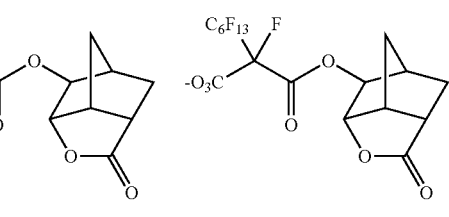
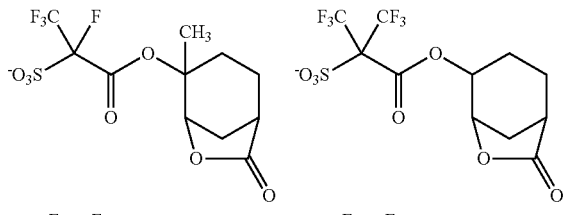
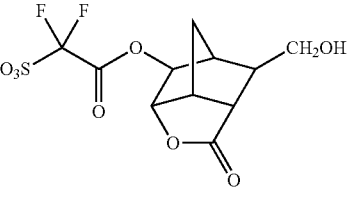
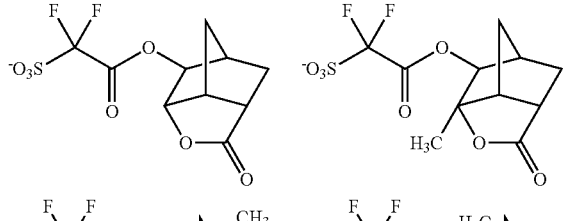
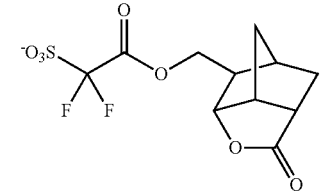
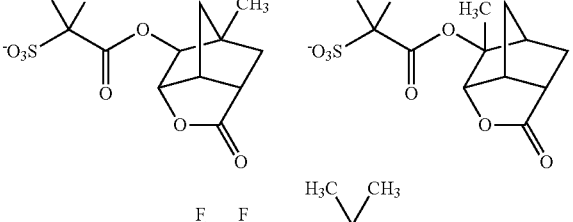
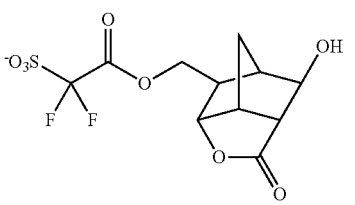
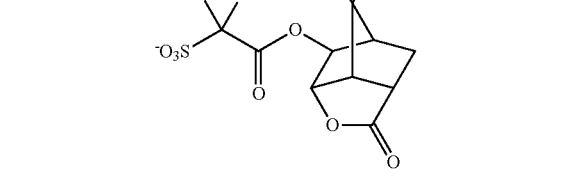
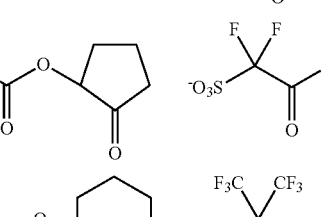
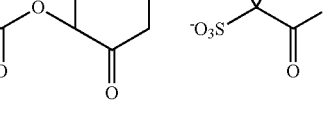

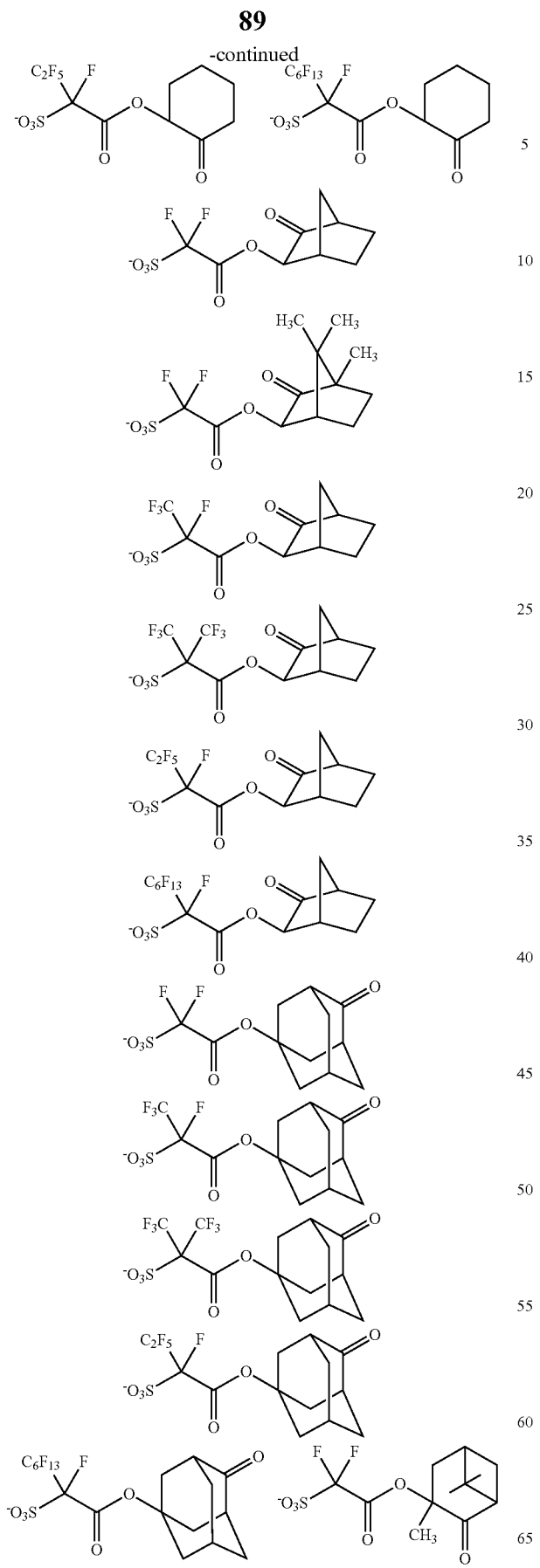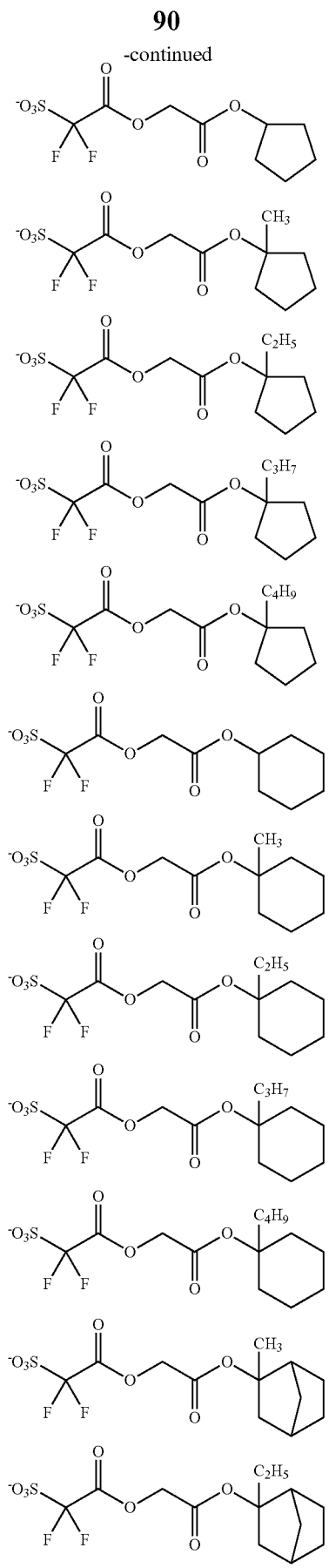

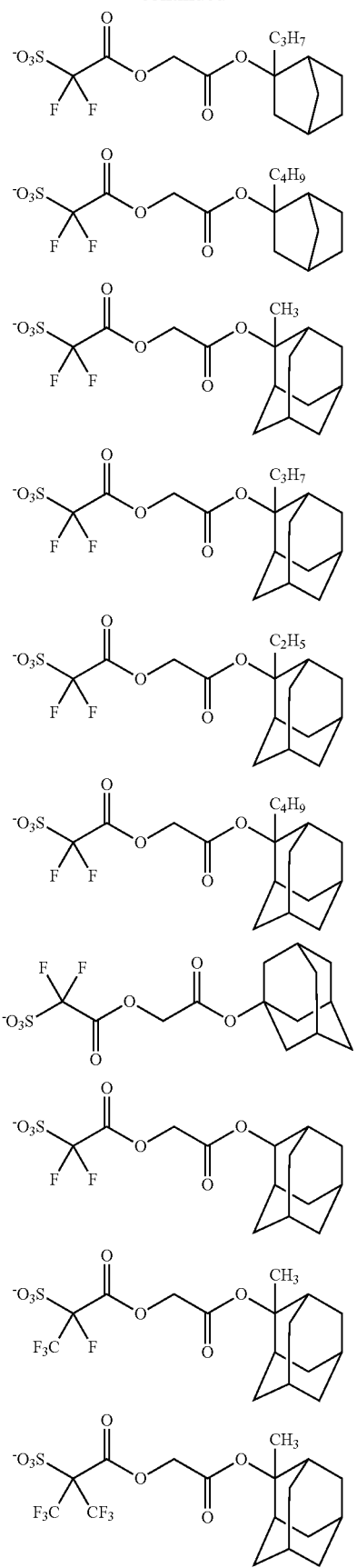
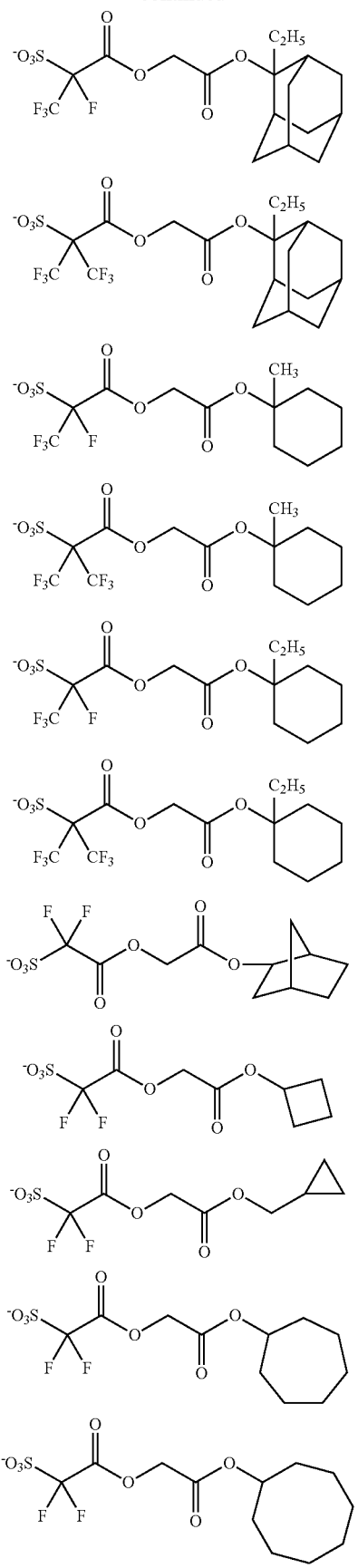

93
-continued
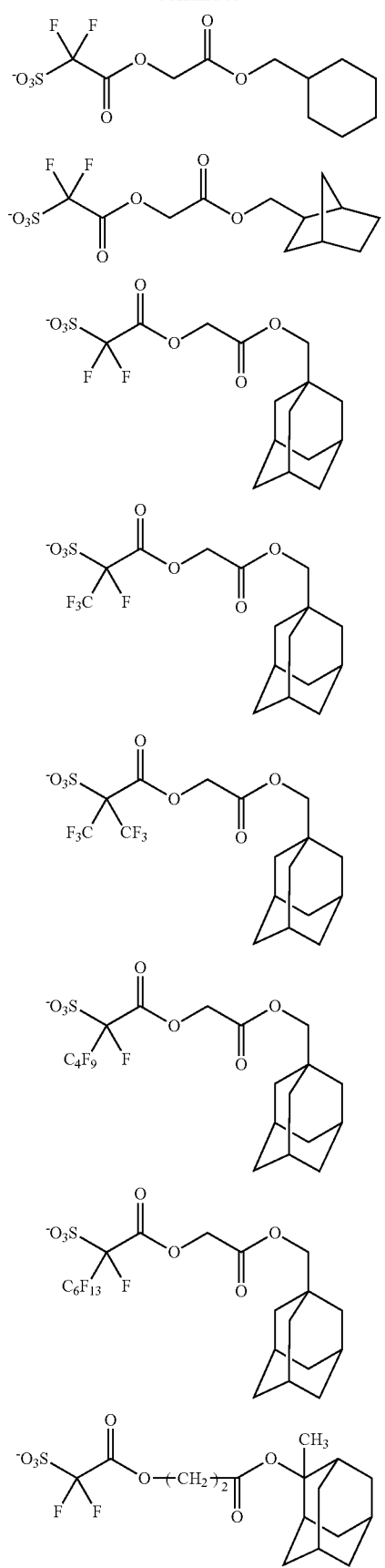
94
-continued
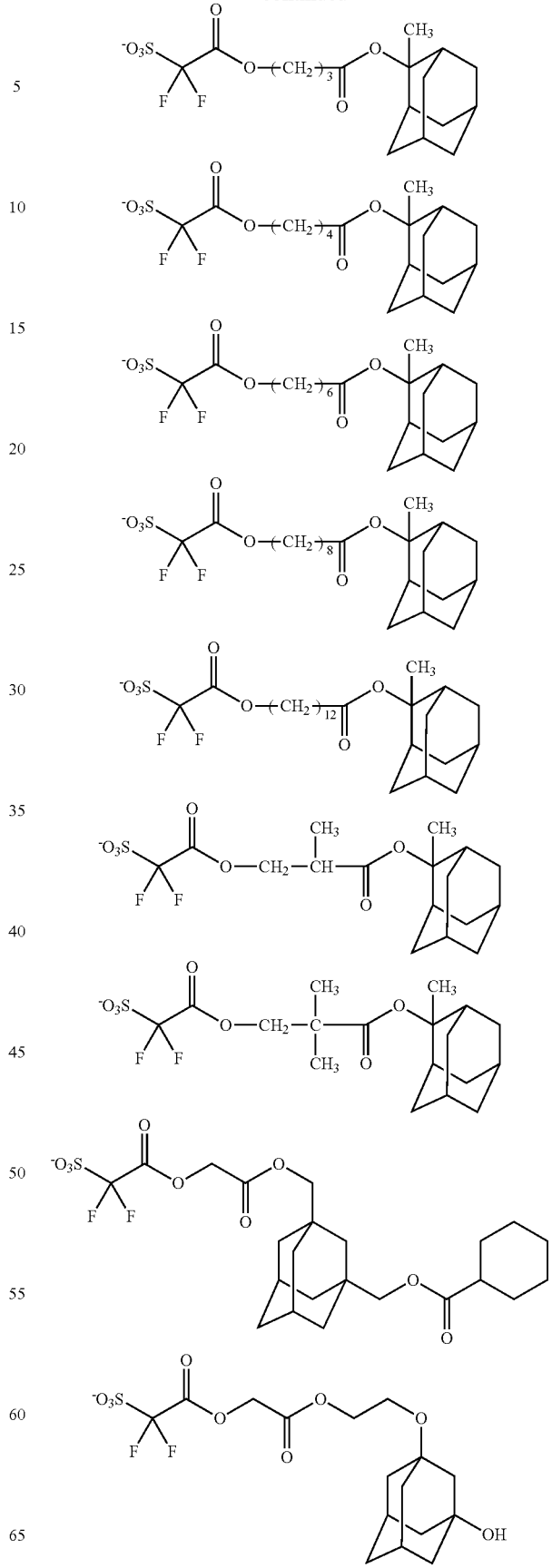

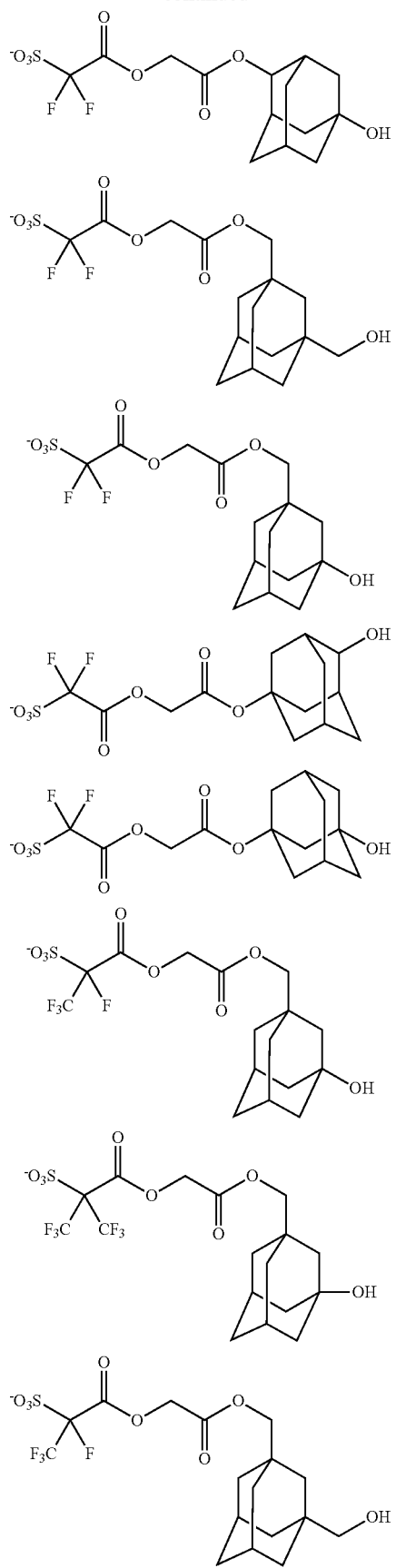
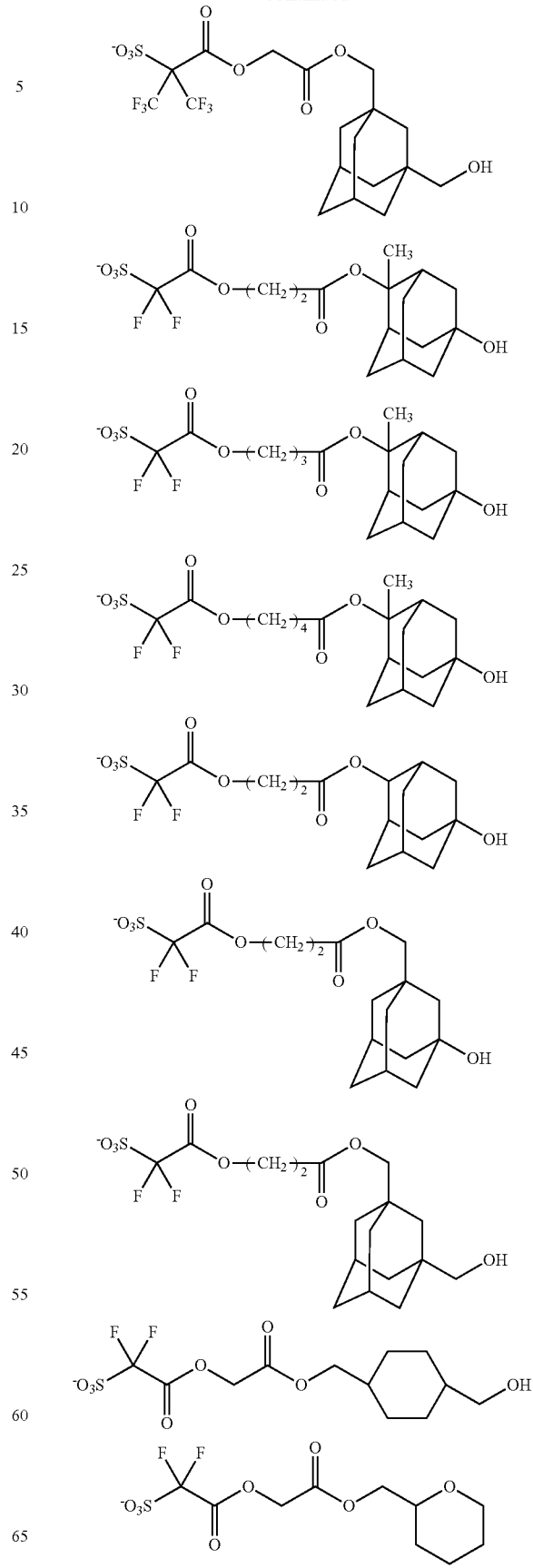

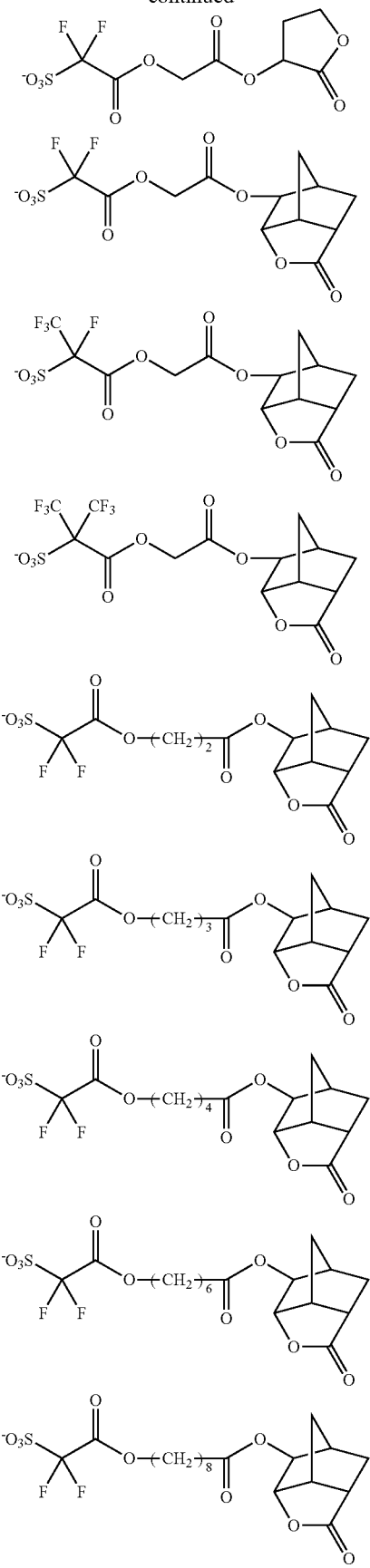
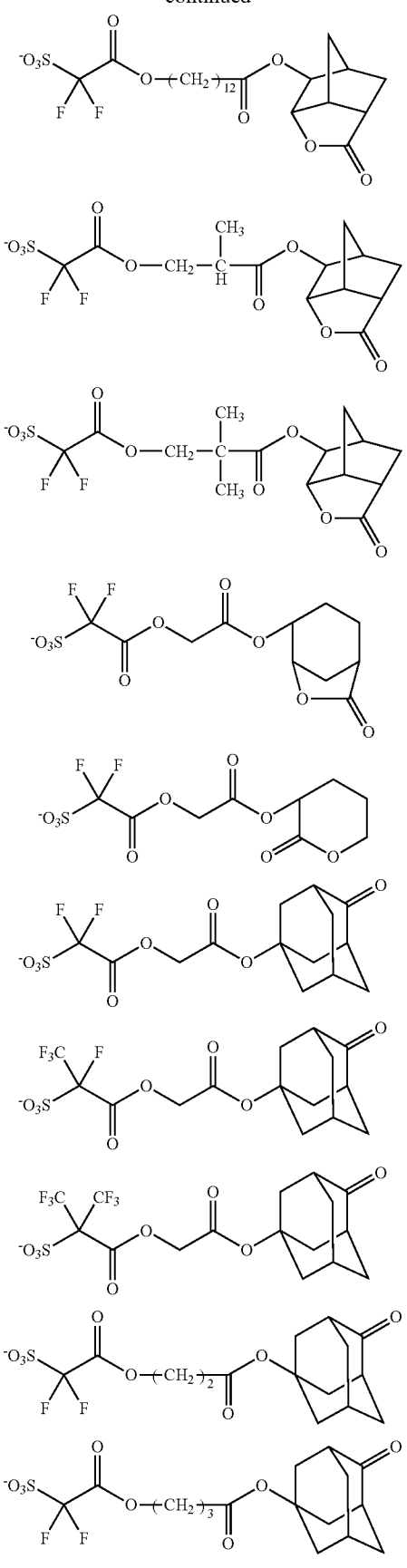

99
-continued
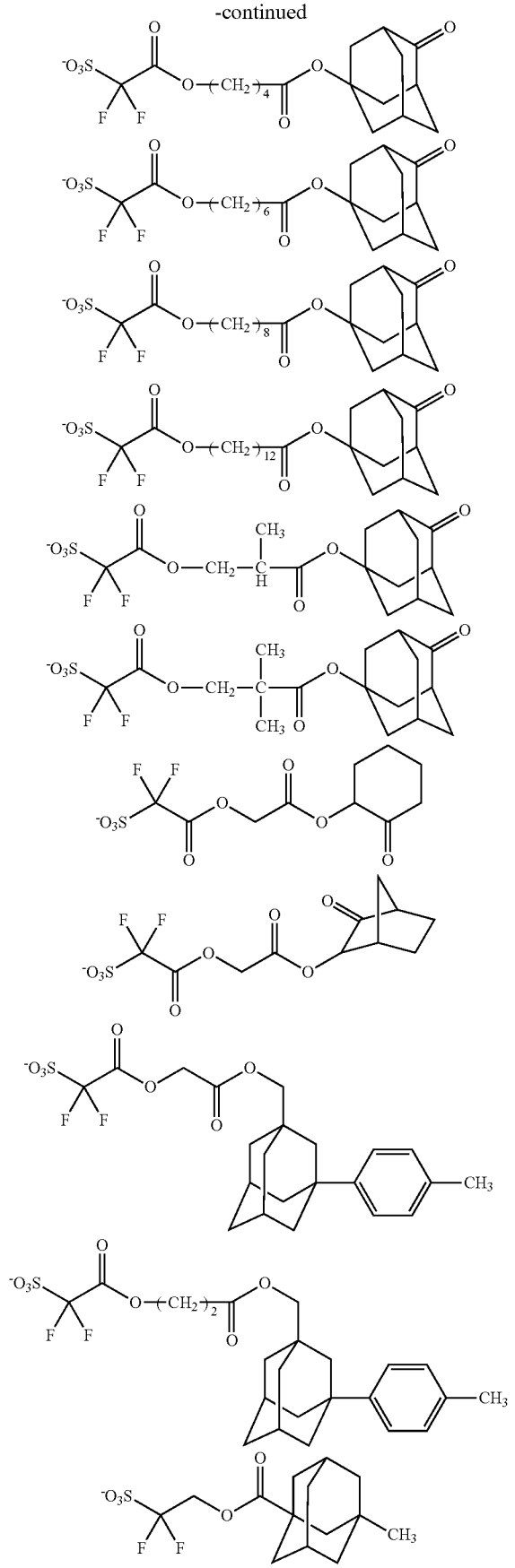
100
-continued
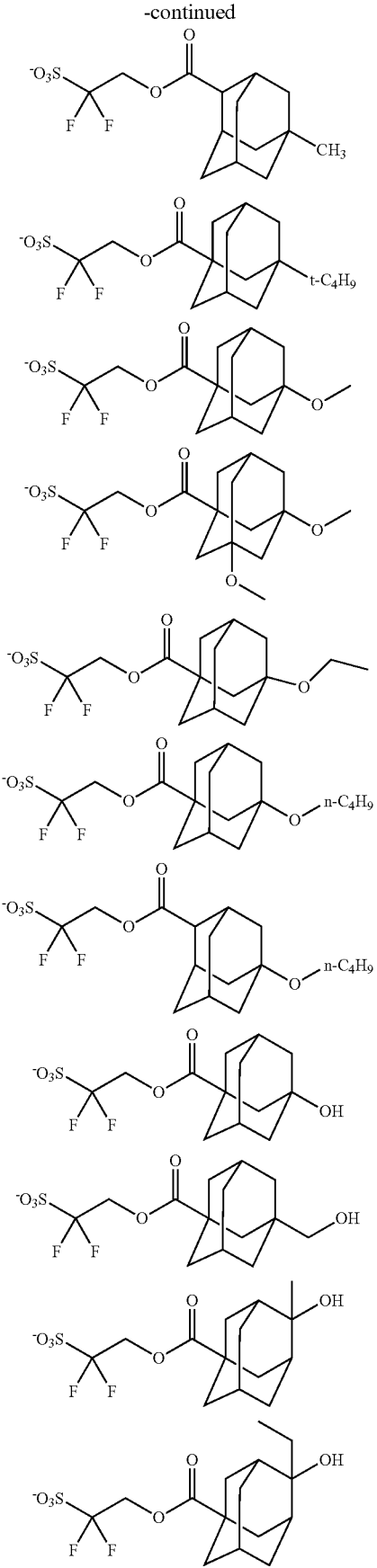

101
-continued
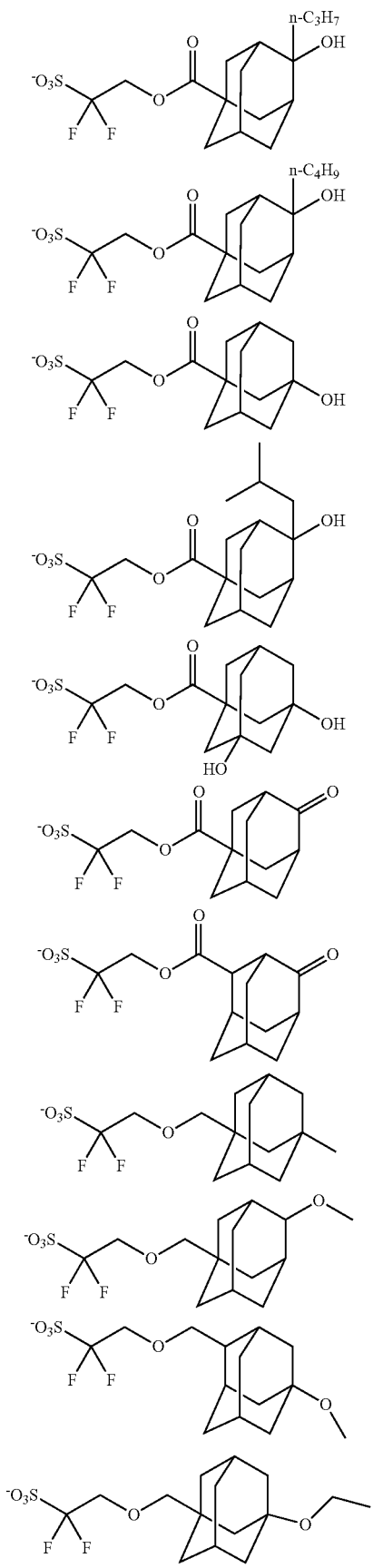
102
-continued
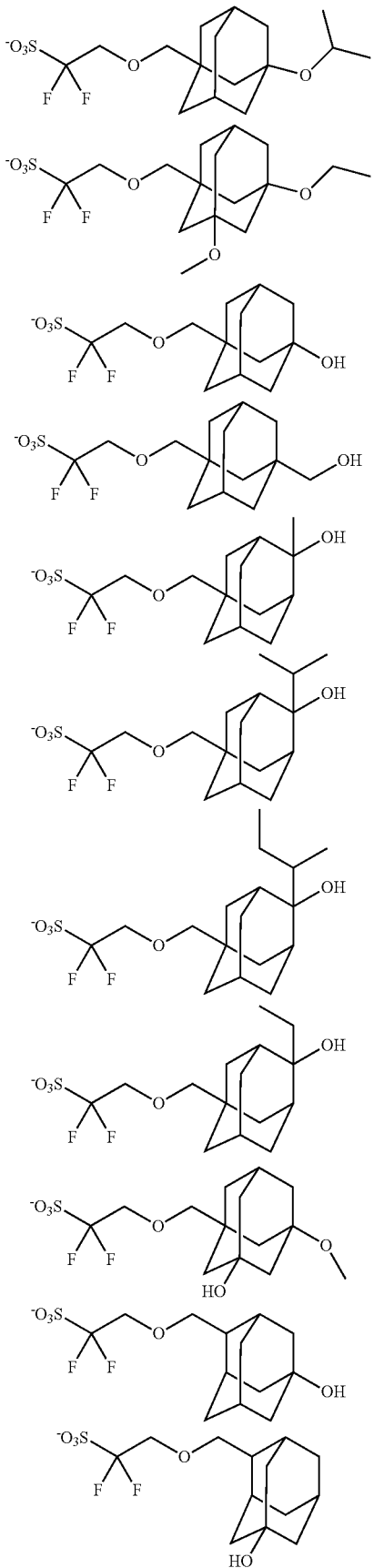

-continued

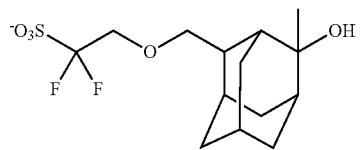

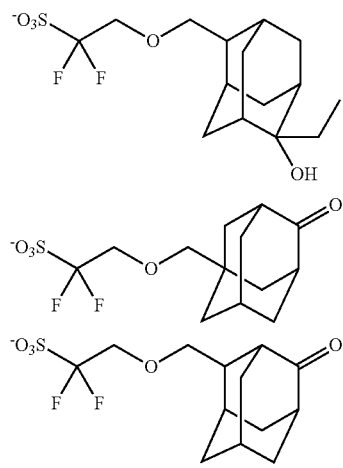

Among them, preferred are the following sulfonic anions.

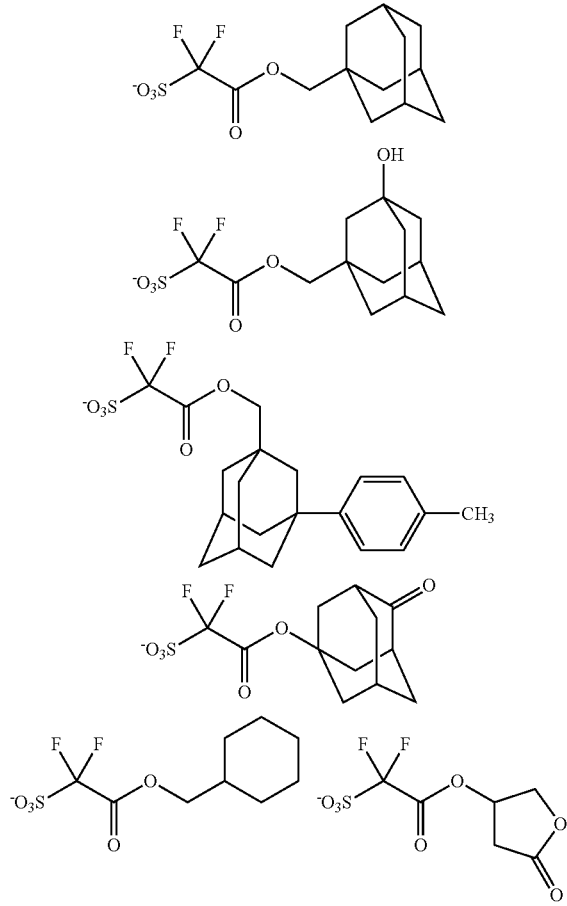

-continued

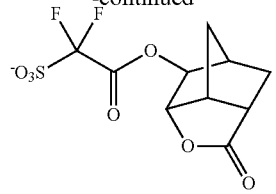

Examples of the cation part represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation part represented by $Z^+$ include the cations represented by the formulae (b2-1) to (b2-4):

  (b2-1)

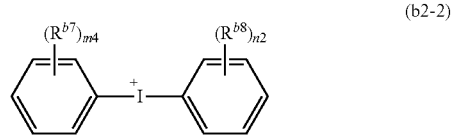  (b2-2)

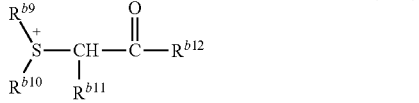  (b2-3)

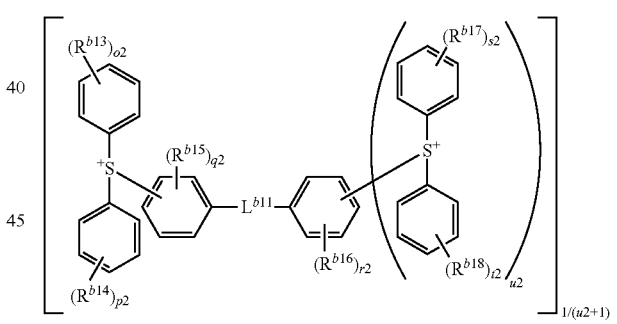  (b2-4)

wherein $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C36 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C36 aliphatic hydrocarbon group, a C3-C36 saturated cyclic hydrocarbon group or a C1-C12 alkoxy group, $R^{b7}$ and $R^{b8}$ are independently in each occurrence a hydroxyl group, a C1-C12 aliphatic hydrocarbon group or a C1-C12 alkoxy group, m4 and n2 independently represents an integer of 0 to 5, $R^{b9}$ and $R^{b10}$ each independently represent a C1-C36 aliphatic hydrocarbon group or a C3-C36 saturated cyclic hydrocarbon group, or $R^{b9}$ and $R^{b10}$ are bonded to form a C2-C11 divalent acyclic hydrocarbon group which forms a ring together with the adjacent S⁺, and one or more —CH₂— in the divalent acyclic hydrocarbon group may be replaced by —CO—, —O— or —S—, and $R^{b11}$ represents a hydrogen atom, a C1-C36 aliphatic hydrocarbon group, a C3-C36 saturated cyclic hydrocarbon group or a C6-C18 aromatic hydrocarbon group, $R^{b12}$ represents a C1-C12 aliphatic hydrocarbon group, a C6-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —CH₂— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Examples of the aliphatic hydrocarbon group, the saturated cyclic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S⁺ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

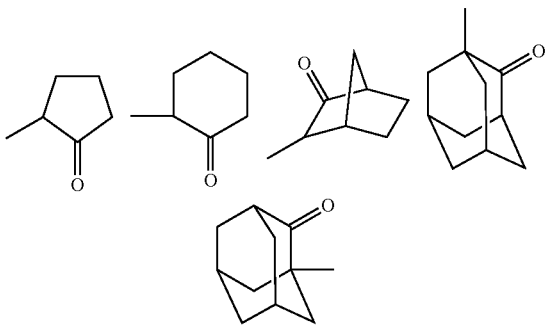

Among the above-mentioned cations, the cation represented by the formula (b2-1) is preferable, and the cation represented by the formula (b2-1-1) is more preferable and a triphenylsulfonium cation is especially preferable.

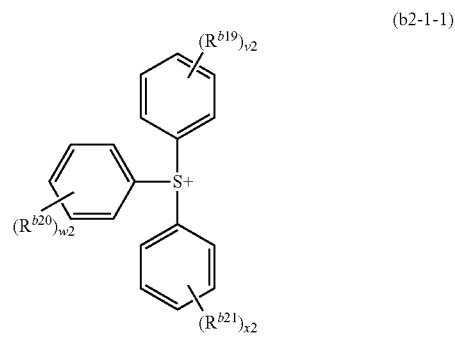

(b2-1-1)

wherein $R^{b19}$, $R^{b20}$ and $R^{b21}$ are independently in each occurrence a hydroxyl group, a C1-C36 aliphatic hydrocarbon group, a C3-C36 saturated cyclic hydrocarbon group or a C1-C12 alkoxy group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, and v2, w2 and x2 independently each represent an integer of 0 to 5. The aliphatic hydrocarbon group preferably has 1 to 12 carbon atoms, and the saturated cyclic hydrocarbon group preferably has 4 to 36 carbon atoms, and it is preferred that v2, w2 and x2 independently each represent 0 or 1. It is preferred that $R^{b19}$, $R^{b20}$ and $R^{b21}$ are independently halogen atom (preferably a fluorine atom), a hydroxyl group, a C1-C12 alkyl group or a C1-C12 alkoxy group.

Examples of the cation represented by the formula (b2-1) include the followings.

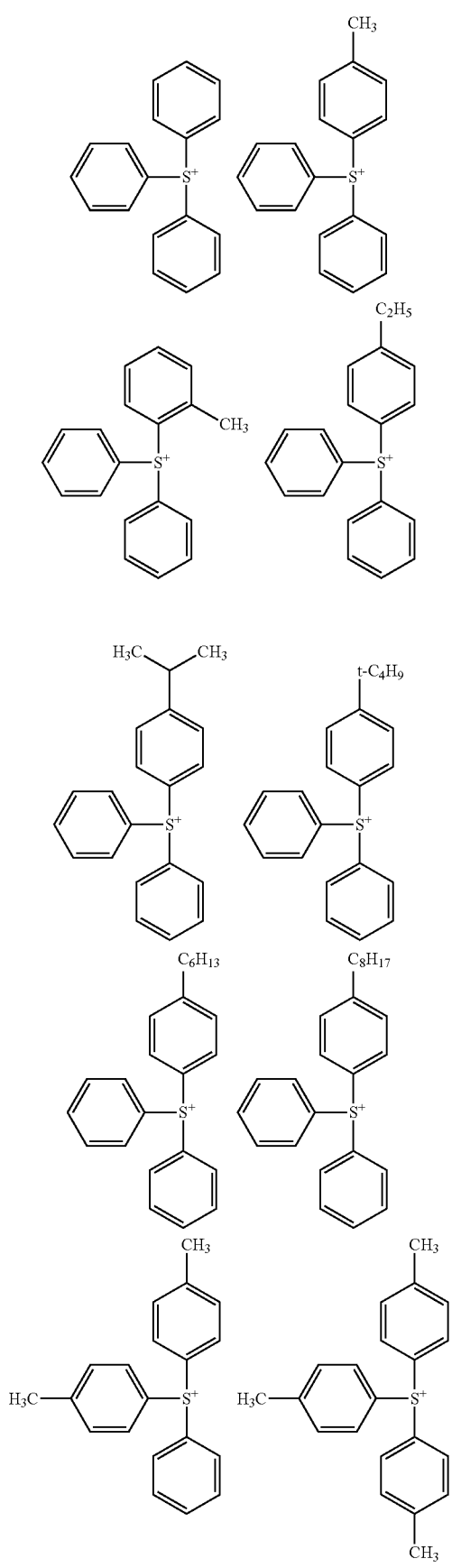
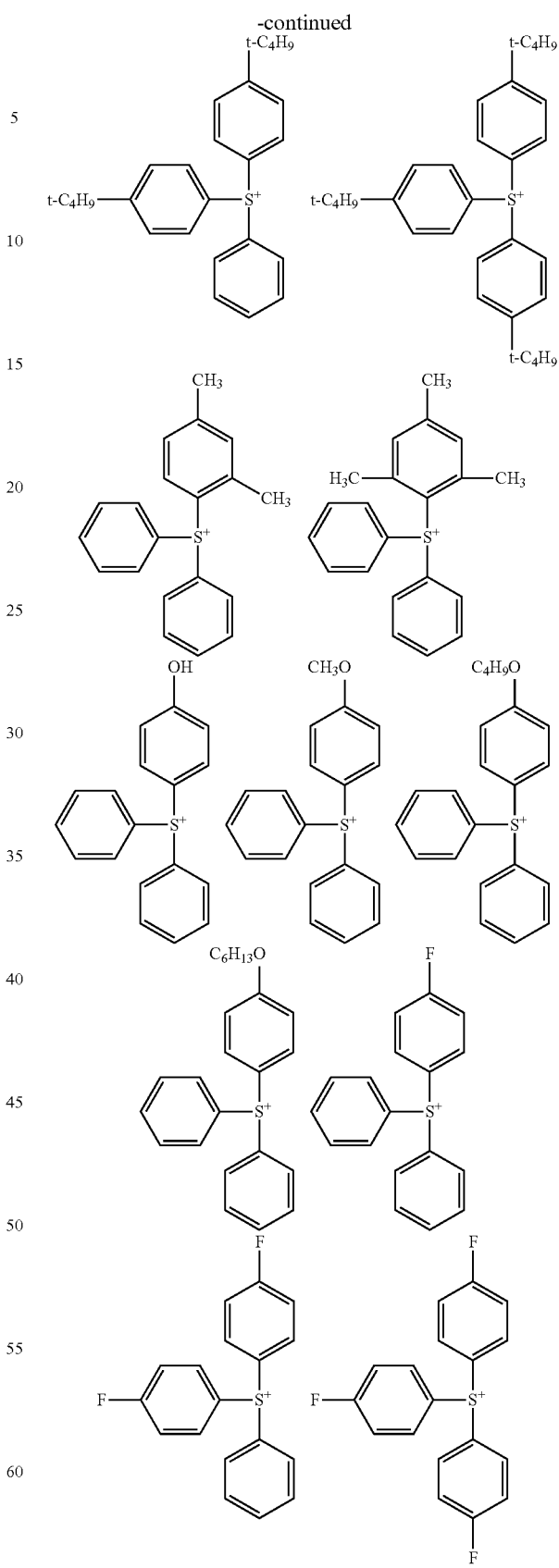
Examples of the cation represented by the formula (b2-2) include the followings.

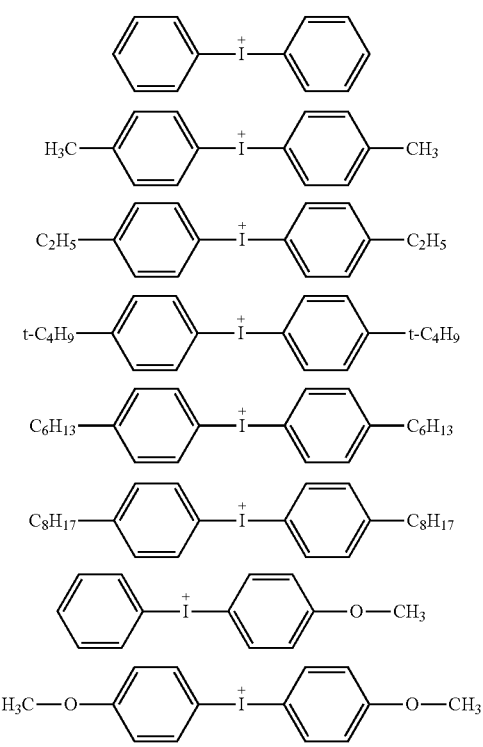
Examples of the cation represented by the formula (b2-3) include the followings.
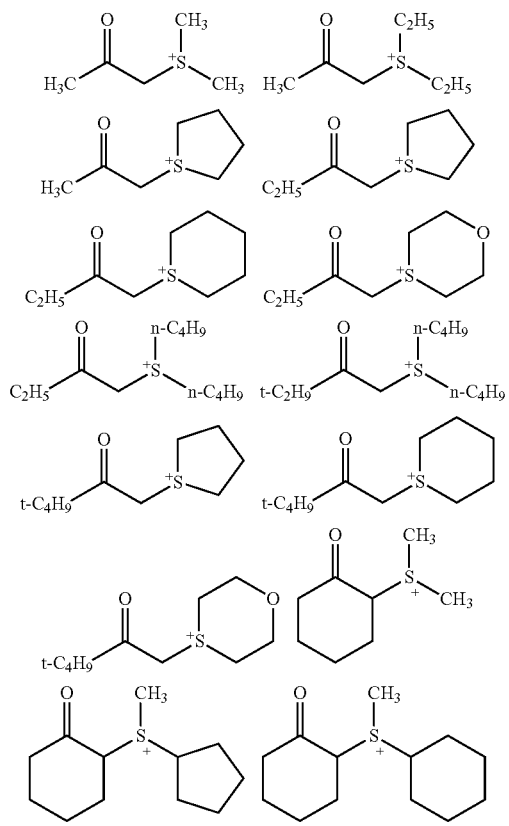
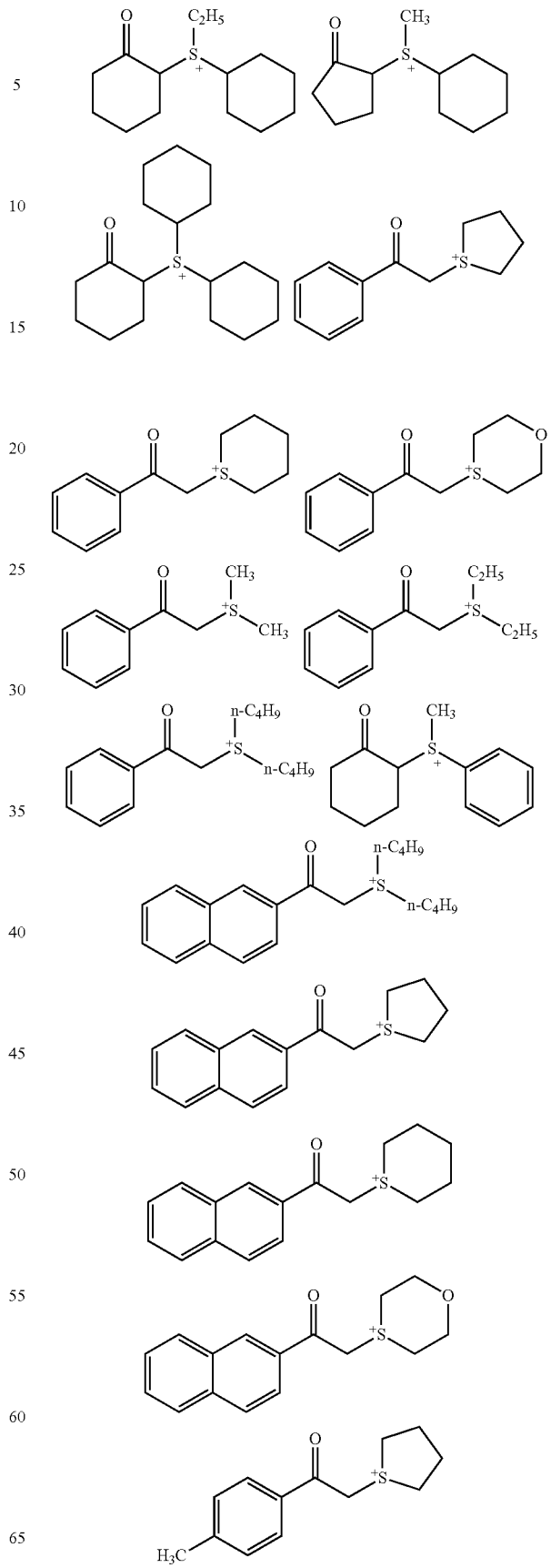

111
-continued
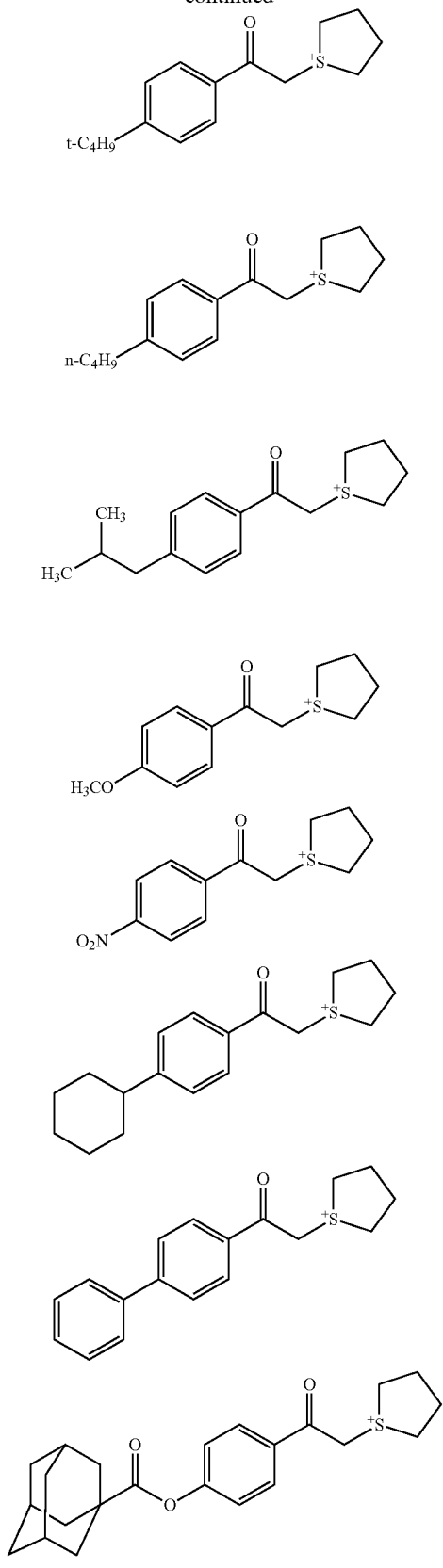
112
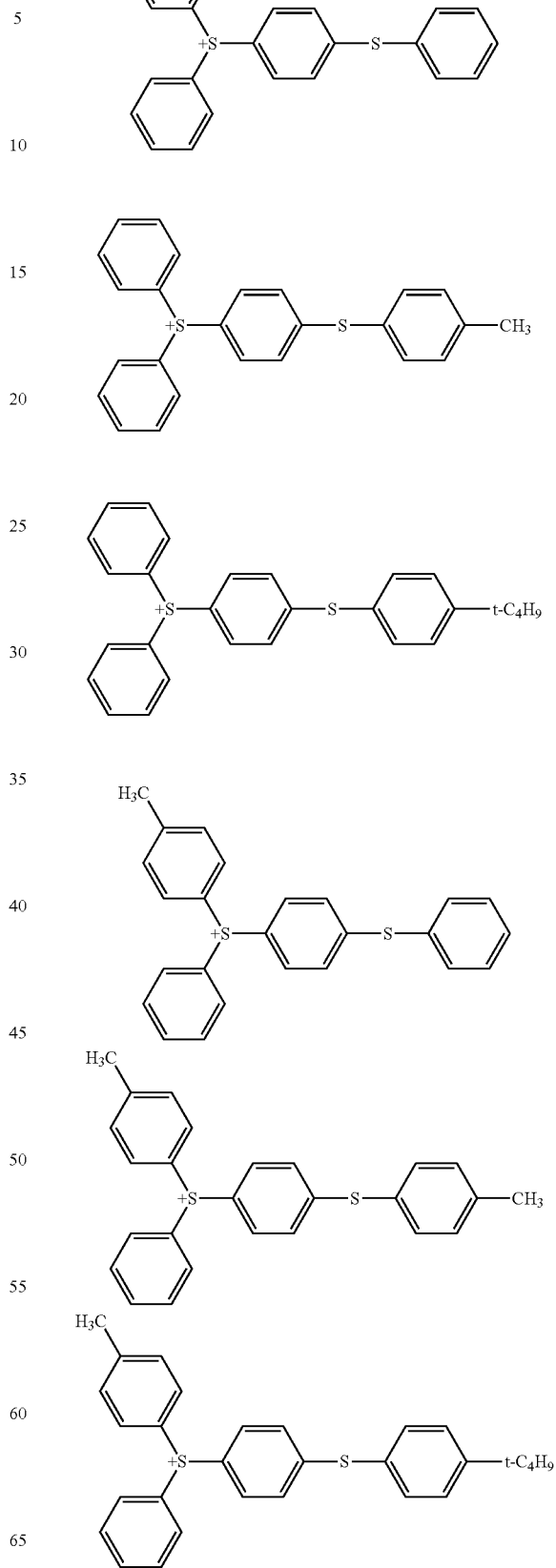
Examples of the cation represented by the formula (b2-4) include the followings.

113
-continued
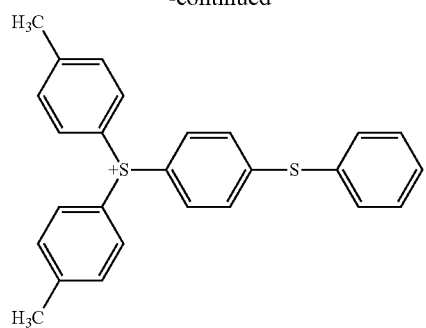
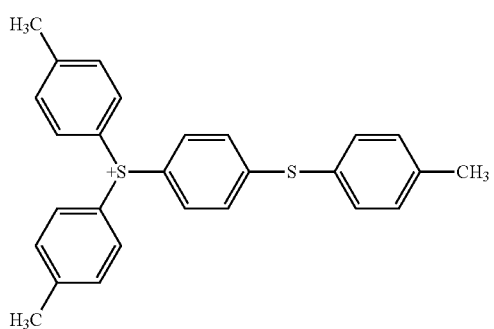
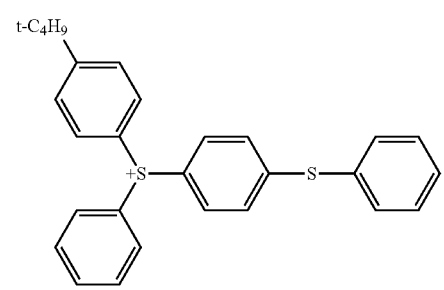
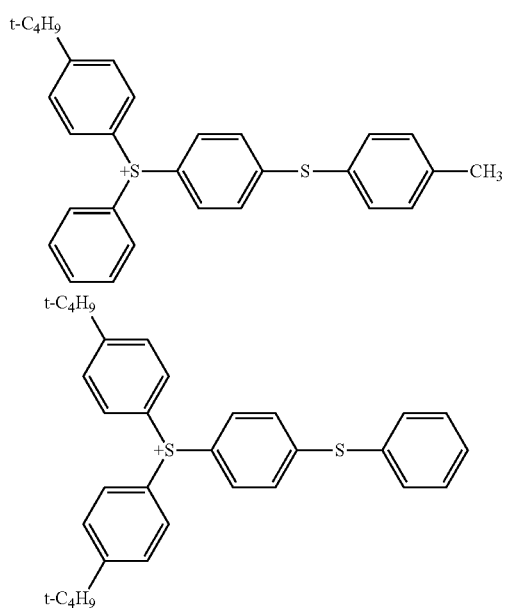
114
-continued
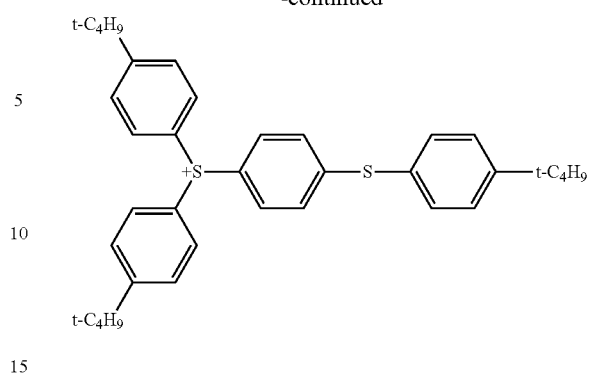
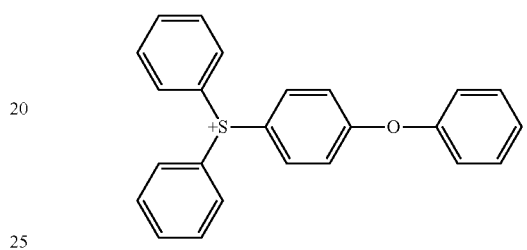
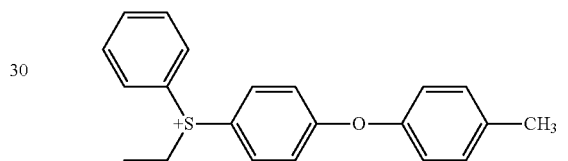
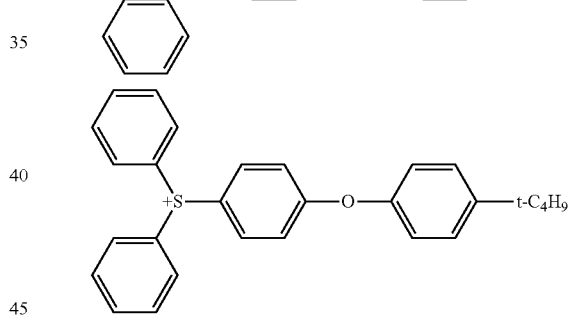
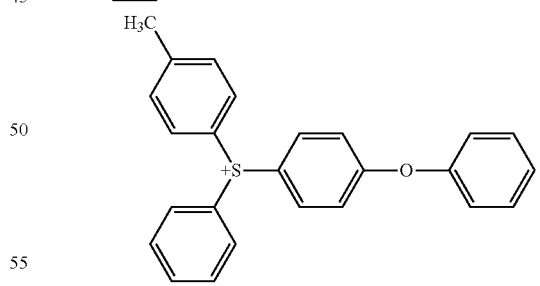
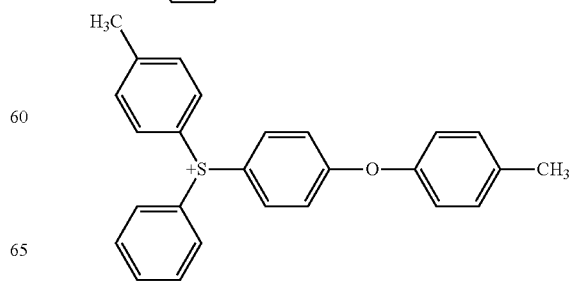

115
-continued
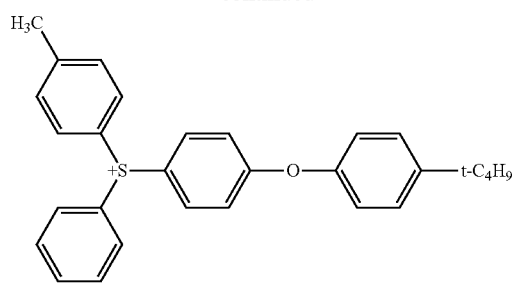
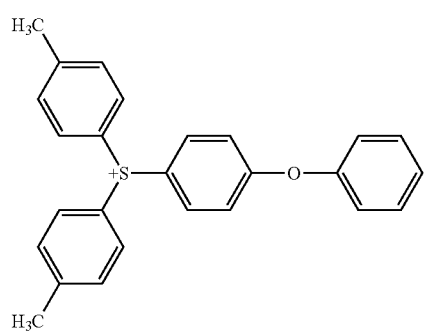
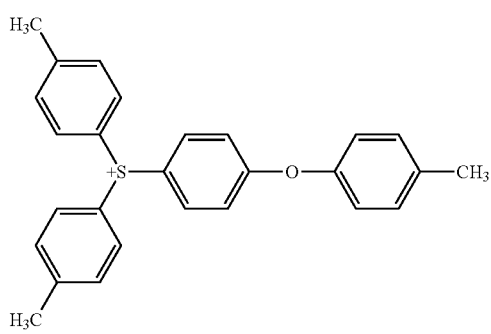
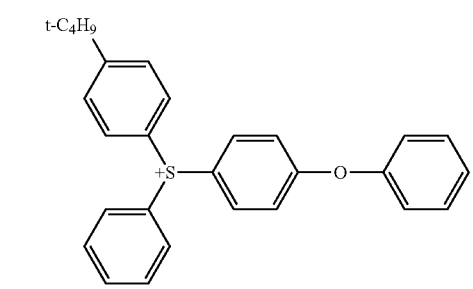
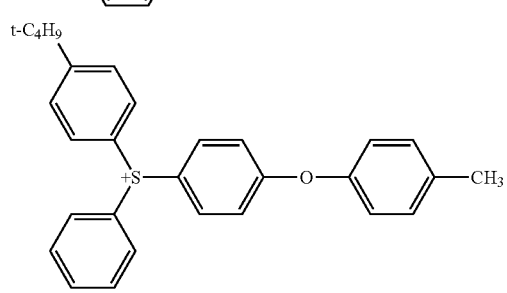
116
-continued
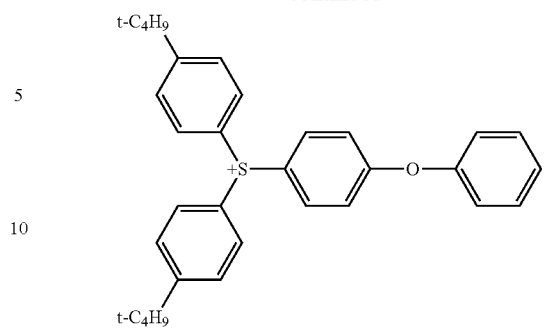
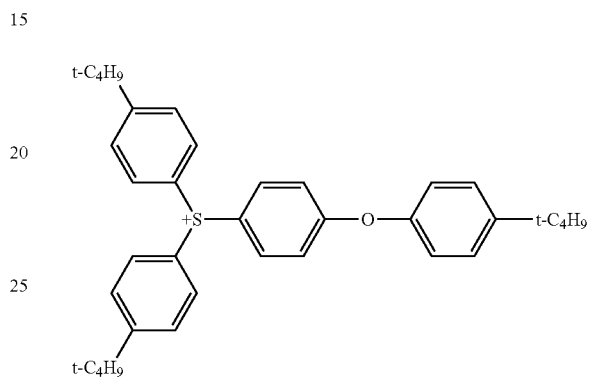
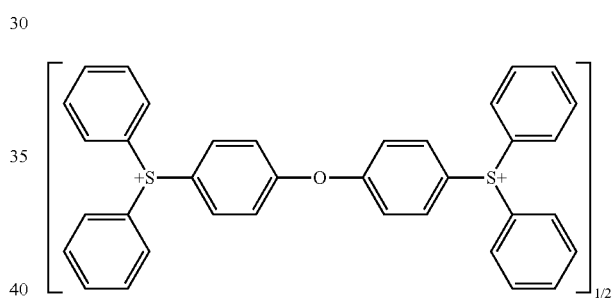
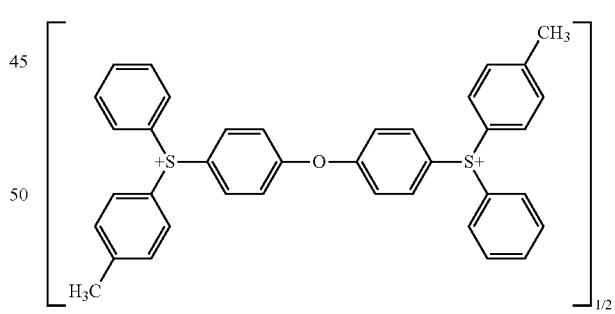
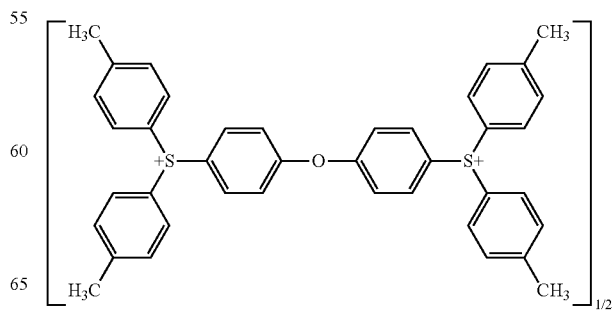

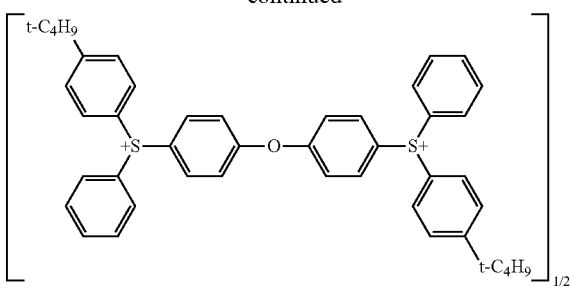
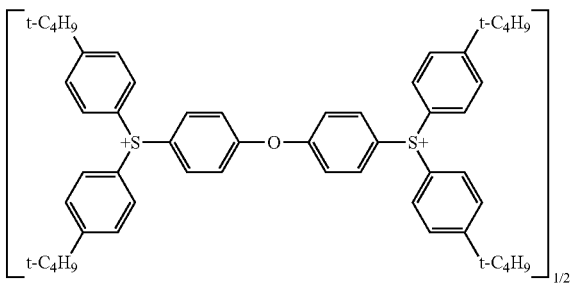
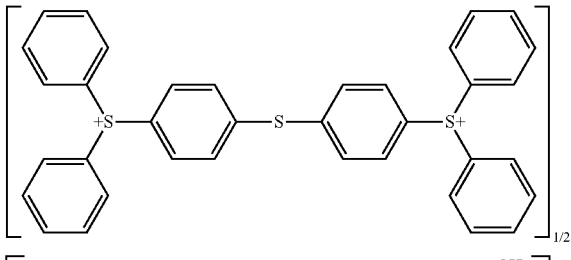
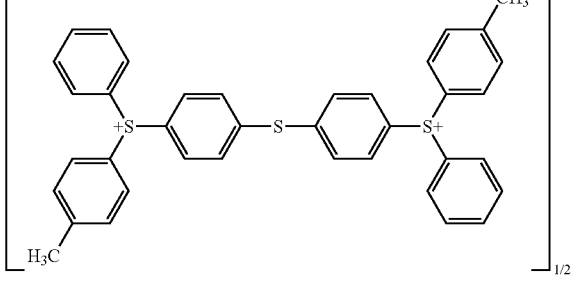
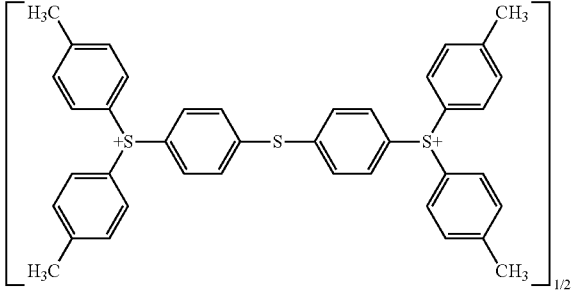
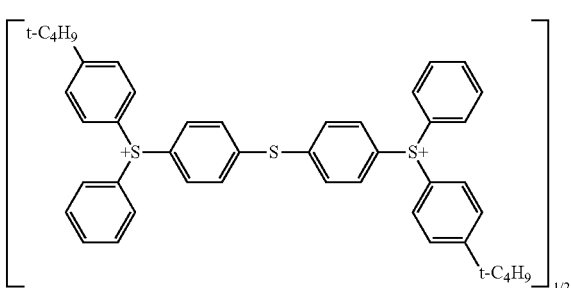

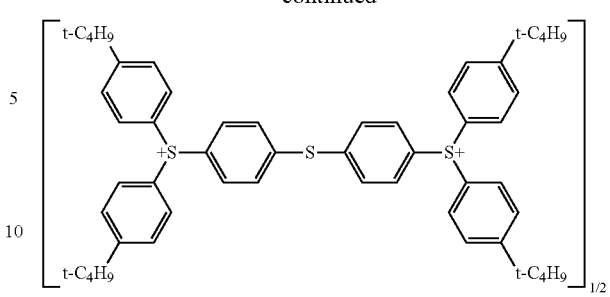

Examples of the salt represented by the formula (B1) include a salt wherein the anion part is any one of the above-mentioned anion part and the cation part is any one of the above-mentioned cation part. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3).

The salt represented by the formulae (B1-1) to (B1-17) are preferable, and the salt represented by the formulae (B1-1), (B1-2), (B1-6), (B1-11), (B1-12), (B1-13) and (B1-14) are more preferable.

(B1-1)

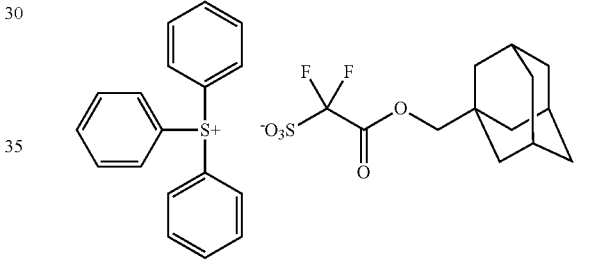

(B1-2)

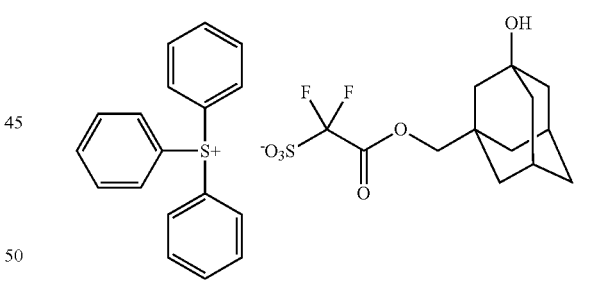

(B1-3)

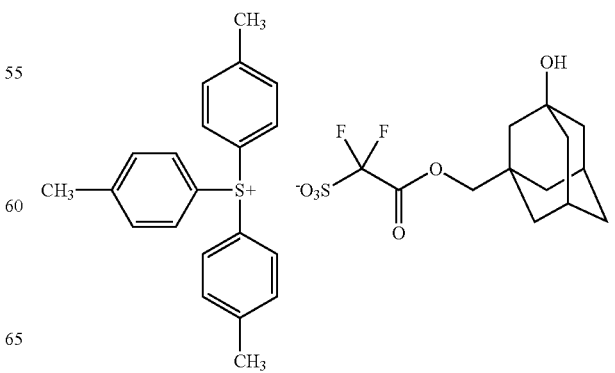

(B1-4)
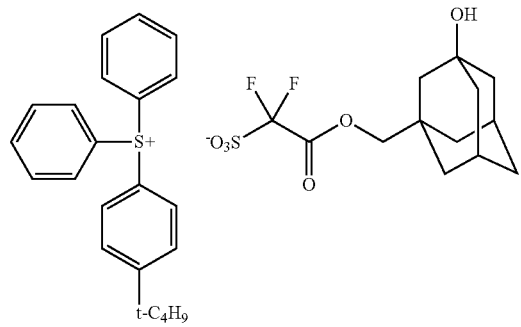
(B1-8)
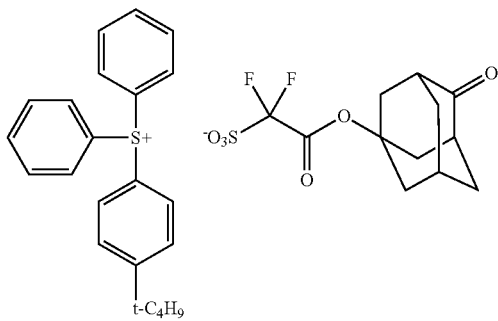
(B1-5)
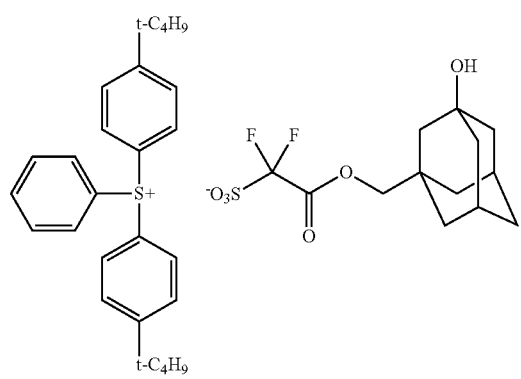
(B1-9)
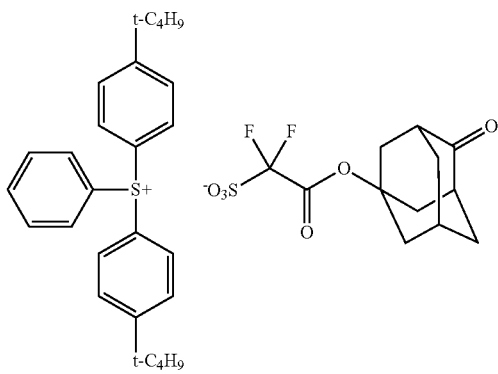
(B1-6)
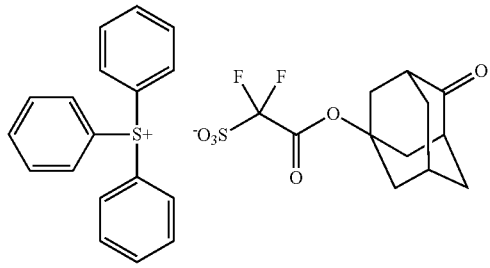
(B1-10)
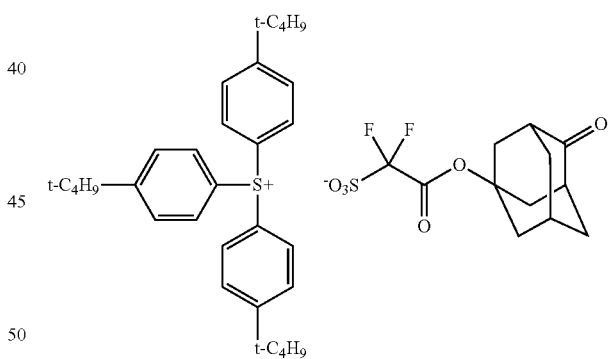
(B1-7)
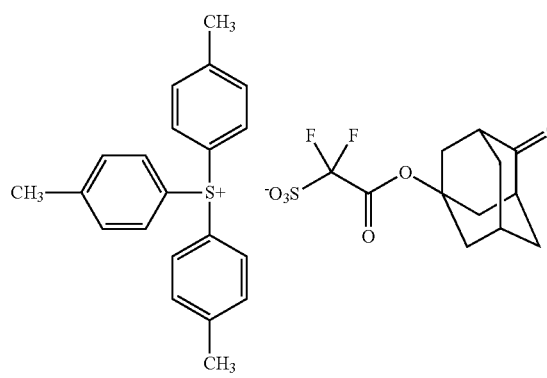
(B1-11)
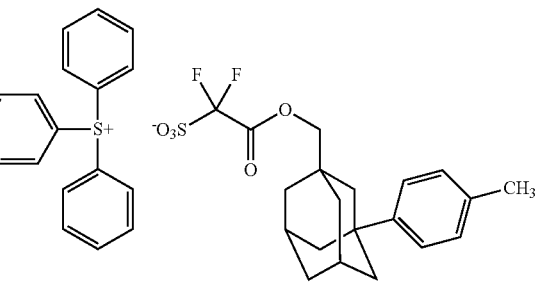

-continued

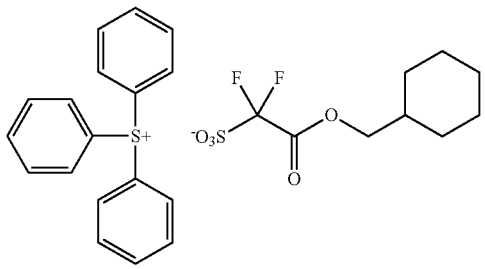
(B1-12)

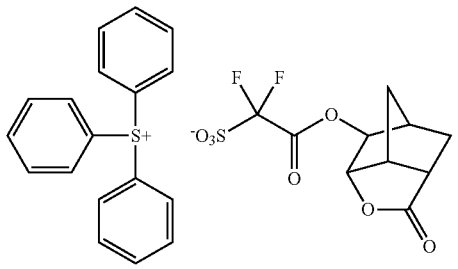
(B1-13)

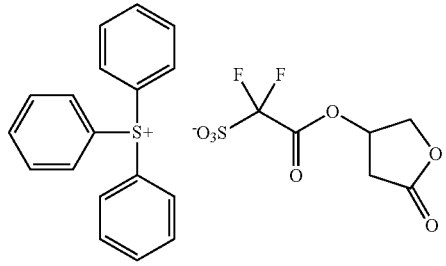
(B1-14)

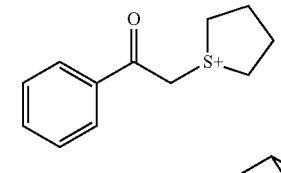
(B1-15)

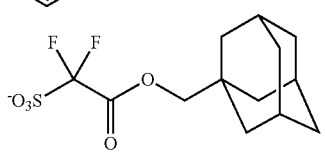
(B1-16)

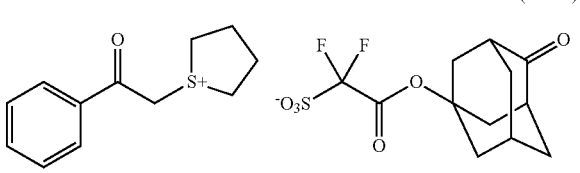
(B1-17)

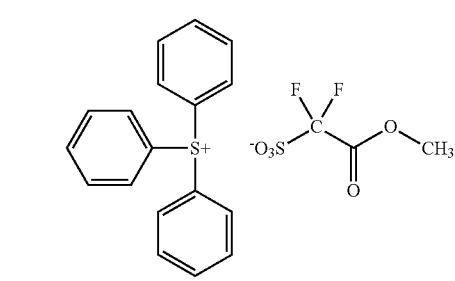

Two or more kinds of the acid generator can be used in combination.

The content of the acid generator is preferably 1 part by weight or more and more preferably 3 parts by weight or more per 100 parts by weight of Resin (A). The content of the acid generator is preferably 20 parts by weight or less and more preferably 15 parts by weight or less per 100 parts by weight of Resin (A).

Next, the second photoresist composition of the present invention will be illustrated.

The second photoresist composition comprises a copolymer comprising a structural unit derived from Compound (I) and a structural unit having an acid-labile group, and being insoluble or poorly soluble in an aqueous alkali solution but becoming soluble in an aqueous alkali solution by the action of an acid (hereinafter, simply referred to as Copolymer (III)), and an acid generator.

Examples of Compound (I) include the same as described above.

Examples of the structural unit having an acid-labile group include the same as described above, and the structural unit derived from the monomer represented by the formulae (a1-1) or (a1-2) is preferable.

The content of the structural unit having an acid-labile group is usually 10 to 80% by mole based on 100% by mole of all the structural units of Copolymer (III), and preferably 20 to 60% by mole. The content of the structural unit derived from Compound (I) is usually 20 to 90% by mole based on 100% by mole of all the structural units of Copolymer (III), and preferably 40 to 80% by mole.

Copolymer (III) preferably contains the structural unit derived from the monomer having no acid-labile group and having one or more hydroxyl groups or a lactone ring, in addition to the structural unit derived from Compound (I) and the structural unit having an acid-labile group. When Copolymer (III) contains the structural unit derived from the monomer having no acid-labile group and having one or more hydroxyl groups or a lactone ring, the content thereof is usually 1 to 60% by mole based on 100% by mole of sum of the structural unit other than the structural unit having an acid-labile group, and preferably 1 to 40% by mole and more preferably 1 to 20% by mole.

Examples of the monomer having no acid-labile group and having one or more hydroxyl groups or a lactone ring include the same as described above.

Copolymer (III) can be produced according to known polymerization methods such as radical polymerization.

The second photoresist composition of the present invention can contain two or more kinds of Copolymer (III).

Copolymer (III) usually has 2,500 or more of the weight-average molecular weight, and preferably 3,000 or more of the weight-average molecular weight. Resin (A) usually has 50,000 or less of the weight-average molecular weight, and preferably has 30,000 or less of the weight-average molecular weight. The weight-average molecular weight can be measured with gel permeation chromatography.

Examples of the acid generator include the same as described above.

The content of the acid generator is preferably 1 part by weight or more and more preferably 3 parts by weight or more per 100 parts by weight of Copolymer (III). The content of the acid generator is preferably 20 parts by weight or less and more preferably 15 parts by weight or less per 100 parts by weight of Copolymer (III).

The first and second photoresist compositions of the present invention can contain a basic compound as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

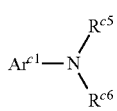

(C2)

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

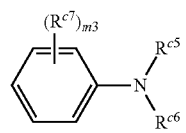

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

(C3)

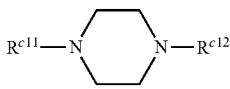

(C4)

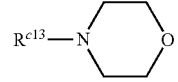

(C5)

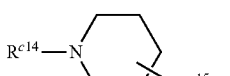

(C6)

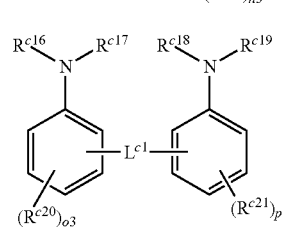

(C7)

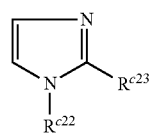

(C8)

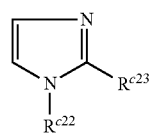

(C9)

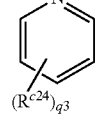

(C10)

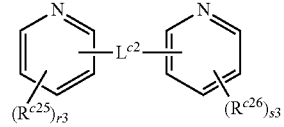

(C11)

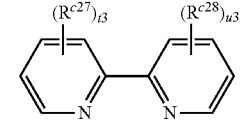

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

When the basic compound is used, the photoresist composition preferably includes 0.01 to 1% by weight of the basic compound based on sum of solid component.

The first and second photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The first and second photoresist compositions of the present invention can contain, if necessary, a small amount of various additives such as a sensitizer, a dissolution inhibitor, other polymers, a surfactant, a stabilizer and a dye as long as the effect of the present invention is not prevented.

The first and second photoresist compositions of the present invention are useful for a chemically amplified photoresist composition.

A photoresist pattern can be produced by the following steps (1) to (5):

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Line Width Roughness (LWR), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography. Furthermore, the photoresist composition of the present invention can also be used in double imaging.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns): TSKgel Multipore HXL-M, manufactured by TOSOH CORPORATION, Solvent: tetrahydrofuran] using standard polystyrene as a standard reference material. Structures of compounds were determined by NMR (GX-270 Type or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Synthesis Example 1

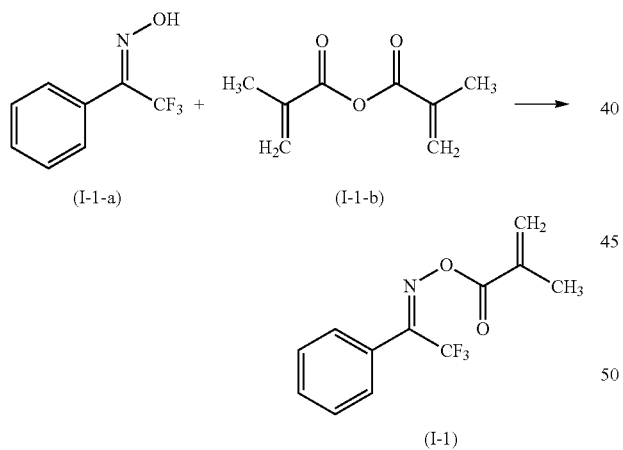

To a solution prepared by mixing 50.0 parts of the compound represented by the formula (I-1-a) and 250 parts of tetrahydrofuran, 29.4 parts of N-methylpyrrolidine and 48.9 parts of the compound represented by the formula (I-1-b) were added. The resultant mixture was stirred at room temperature for 3 hours. To the obtained mixture, 63 parts of 5% hydrochloric acid and 200 parts of ion-exchanged water were added, and then, the resultant mixture was extracted with 500 parts of ethyl acetate. The obtained organic layer was mixed with 146 parts of 10% aqueous potassium carbonate solution, and the resultant mixture was stirred over night followed by removing an aqueous layer. The obtained organic layer was washed with ion-exchanged water and then, concentrated under reduced pressure to obtain 66.2 parts of the compound represented by the formula (I-1). The obtained compound is called as Monomer (I-1).

$^1$H-NMR (dimethylsulfoxide-$d_6$): δ (ppm) 7.66-7.52 (5H, m), 5.85-5.82 (1H, m), 5.80-5.76 (1H, m), 1.81-1.76 (3H, m)

MS (ESI(+)) Spectrum): [M+Na]$^+$=280.1 ($C_{12}H_{10}F_3NO_2$=257.1)

Synthesis Example 2

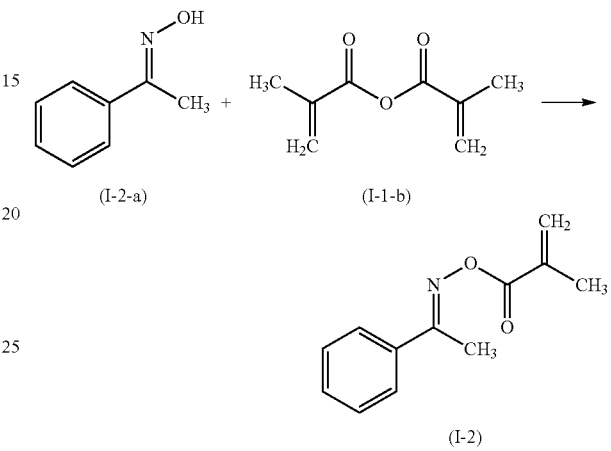

The compound represented by the formula (I-2) was obtained according to the same manner in Synthesis Example 1 except that the compound represented by the formula (I-2-a) was used in place of the compound represented by the formula (I-1-a). The obtained compound is called as Monomer (I-2).

MS (ESI(+)) Spectrum): [M+Na]$^+$=226.1 ($C_{12}H_{13}NO_2$=203.1)

Synthesis Example 3

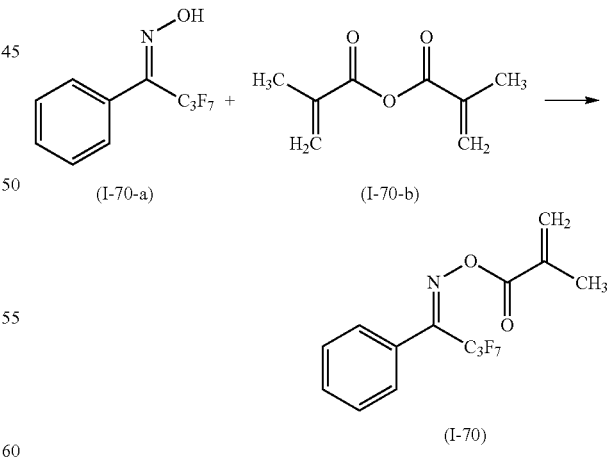

To a solution prepared by mixing 42.3 parts of the compound represented by the formula (I-70-a) and 170 parts of ethyl acetate, 13.7 parts of N-methylpyrrolidine and 24.8 parts of the compound represented by the formula (I-70-b) were added. The resultant mixture was stirred at room temperature for 3 hours. To the obtained mixture, 35 parts of 5% hydrochloric acid and 135 parts of ion-exchanged water were added, and then, the resultant mixture was extracted with 330 parts of ethyl acetate. The obtained organic layer was mixed with 111 parts of 10% aqueous potassium carbonate solution, and the resultant mixture was stirred over night followed by removing an aqueous layer. The obtained organic layer was washed with ion-exchanged water and then, concentrated under reduced pressure to obtain 52.3 parts of the compound represented by the formula (I-70). The obtained compound is called as Monomer (I-70).

$^1$H-NMR (dimethylsulfoxide-$d_6$): δ (ppm) 7.65-7.51 (5H, m), 5.75-5.82 (2H, m), 3.05 (3H, s)

MS (ESI(+)  Spectrum):  [M+Na]$^+$=357.1 ($C_{14}H_{10}F_7NO_2$=357.1)

Synthesis Example 4

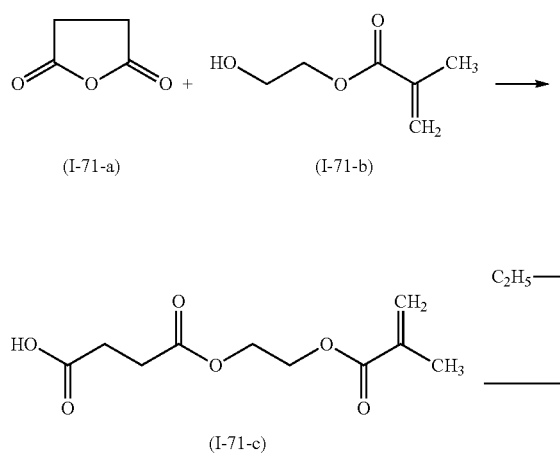

MS (ESI(+))  Spectrum):  [M+Na]$^+$=424.1 ($C_{18}H_{18}F_3NO_6$=401.1)

Synthesis Example 5

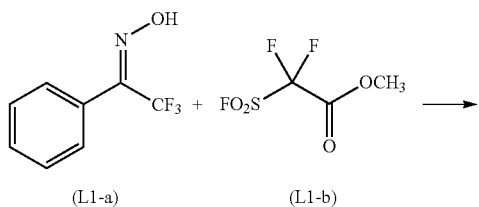

To a solution prepared by mixing 5.0 parts of the compound represented by the formula (I-71-a) and 35 parts of tetrahydrofuran, 4.67 parts of N-methylpyrrolidine and 4.62 parts of the compound represented by the formula (I-71-b) were added. The resultant mixture was stirred at room temperature for 18 hours. To the obtained mixture, 5.72 parts of the compound represented by the formula (I-71-d) and 7.27 parts of the compound represented by the formula (I-71-e) were added. The resultant mixture was stirred at room temperature for 3 hours. To the obtained mixture, 87 parts of aqueous saturated ammonium chloride solution was added, and then, the resultant mixture was extracted with 175 parts of ethyl acetate. The obtained organic layer was washed with ion-exchanged water and then, concentrated under reduced pressure. The obtained residue was purified with silica gel chromatography (solvent: ethyl acetate/heptane=7/1) to obtain 12.3 parts of the compound represented by the formula (I-71). The obtained compound is called as Monomer (I-71).

$^1$H-NMR (dimethylsulfoxide-$d_6$): δ (ppm) 7.65-7.55 (5H, m), 6.02 (1H, s), 5.71-5.52 (1H, m), 4.38-4.21 (4H, m), 2.73-2.68 (2H, m), 2.61-2.51 (2H, m), 1.86 (3H, s)

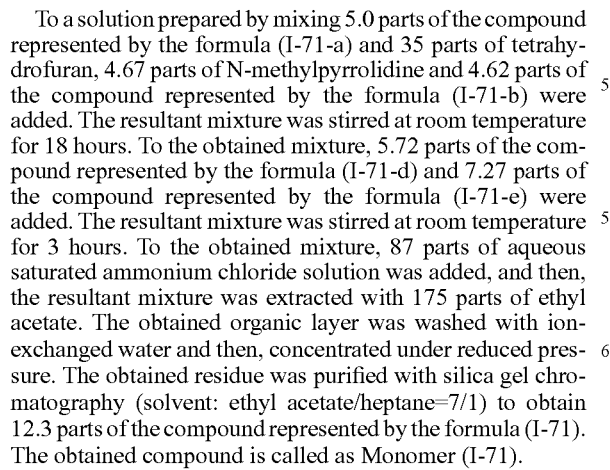

-continued

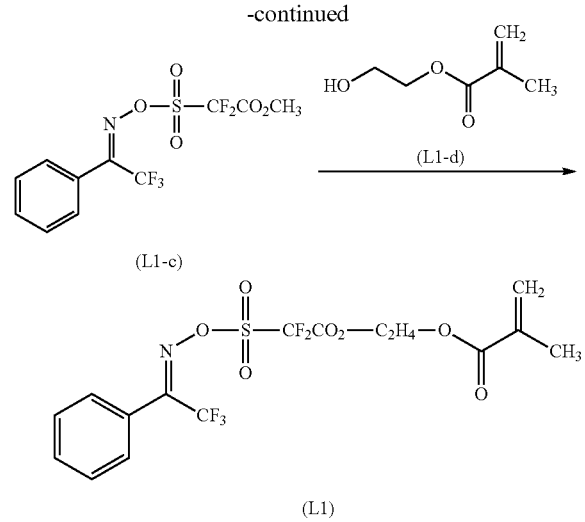

To a solution prepared by mixing 20 parts of the compound represented by the formula (L1-a) and 30 parts of N,N-dimethylformamide, 9 parts of 2,6-lutidine and 16 parts of the compound represented by the formula (L1-b) were added. The resultant mixture was stirred at room temperature for 17 hours. To the obtained mixture, an aqueous saturated ammonium chloride solution was added, and then, the resultant mixture was extracted with ethyl acetate. The obtained organic layer was washed with ion-exchanged water and then, concentrated under reduced pressure. The obtained residue was purified with silica gel chromatography to obtain 30 parts of the compound represented by the formula (L1-c).

$^1$H-NMR (dimethylsulfoxide-$d_6$): δ (ppm) 7.74–7.60 (5H, m), 3.98 (3H, s)

$^{19}$F-NMR (dimethylsulfoxide-$d_6$): δ (ppm) –99.50, –62.25

To a solution prepared by mixing 30 parts of the compound represented by the formula (L1-c) and 150 parts of chloroform, 12.15 parts of the compound represented by the formula (L1-d), 0.04 part of hydroquinone monomethyl ether and 1.27 parts of samarium triisopropoxide were added. The resultant mixture was stirred under reflux for 23 hours. The obtained mixture was cooled down to room temperature, and 12 parts of silica gel was added thereto. The obtained mixture was stirred for 30 minutes and then, filtrated. The obtained filtrate was concentrated under reduced pressure, and the obtained residue was mixed with heptane and ion-exchanged water to conduct extraction. The obtained organic layer was washed three times with ion-exchanged water and then, concentrated under reduced pressure to obtain 25.5 parts of the compound represented by the formula (L1). The obtained compound is called as Monomer (L1).

$^1$H-NMR (dimethylsulfoxide-$d_6$): δ (ppm) 7.74–7.59 (5H, m), 6.03 (1H, s), 5.67–5.66 (1H, m), 4.72–4.69 (2H, m), 4.41–4.38 (2H, m), 1.85 (3H, s)

$^{19}$F-NMR (dimethylsulfoxide-$d_6$): δ (ppm) –99.65, –62.33

In Resin Synthesis Examples, Monomer (M-1), Monomer (M-2), Monomer (M-3), Monomer (M-4), Monomer (M-5), Monomer (M-6) and Monomer (M-8) represented by the followings were used in addition to monomers prepared in the above.

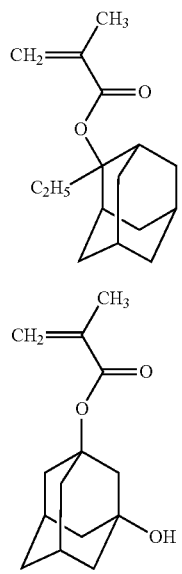

(M-1)

(M-2)

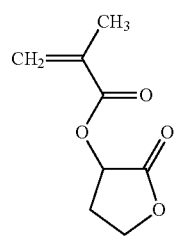

(M-3)

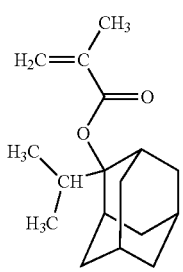

(M-4)

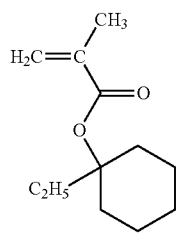

(M-5)

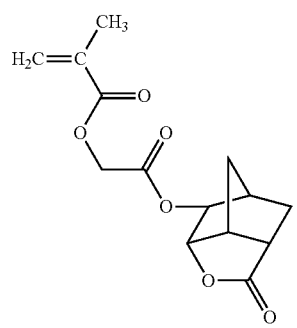

(M-6)

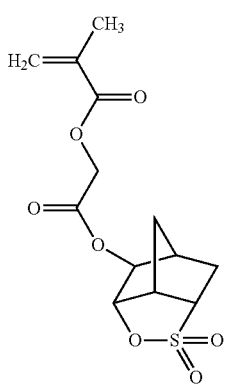

(M-8)

Resin Synthesis Example 1

To a four-necked flask equipped with a stirrer, a thermometer and a reflux condenser, 2.9 parts of 1,4-dioxane was added. After heating it up to 72° C., a solution prepared by mixing 9.8 parts of Monomer (I-1), 0.09 part of 2,2'-azobisisobutyronitrile, 0.42 part of 2,2'-azobis(2,4-dimethylvaleronitrile) and 11.7 parts of 1,4-dioxane was added dropwise thereto over 2 hour. The resultant mixture was stirred for 5 hours at 72° C. The obtained reaction mixture was diluted with 10.7 parts of 1,4-dioxane and then, the resultant mixture was poured into 127 parts of heptane to cause precipitation. The precipitate was isolated and dissolved in propylene glycol monomethyl ether acetate. The obtained solution was concentrated to obtain 30 parts of a solution containing a polymer consisting of the structural unit represented by the following:

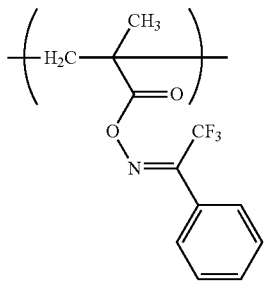

having a weight-average molecular weight (Mw) of $1.4 \times 10^4$ and a dispersion degree (Mw/Mn) of 2.2. The content of solid components in the solution was 33%. This polymer is called as Polymer (II-1).

Resin Synthesis Example 2

To a four-necked flask equipped with a stirrer, a thermometer and a reflux condenser, 2.9 parts of 1,4-dioxane was added. After heating it up to 72° C., a solution prepared by mixing 9.8 parts of Monomer (I-1), 0.06 part of 2,2'-azobisisobutyronitrile, 0.28 part of 2,2'-azobis(2,4-dimethylvaleronitrile) and 11.7 parts of 1,4-dioxane was added dropwise thereto over 2 hour. The resultant mixture was stirred for 5 hours at 72° C. The obtained reaction mixture was diluted with 10.7 parts of 1,4-dioxane and then, the resultant mixture was poured into 127 parts of heptane to cause precipitation. The precipitate was isolated and dissolved in propylene glycol monomethyl ether acetate. The obtained solution was concentrated to obtain 28 parts of a solution containing a polymer consisting of the structural unit represented by the following:

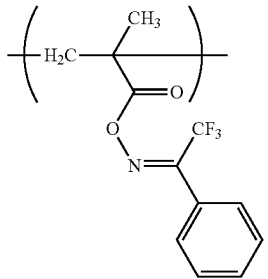

having a weight-average molecular weight (Mw) of $2.3 \times 10^4$ and a dispersion degree (Mw/Mn) of 3.0. The content of solid components in the solution was 34%. This polymer is called as Polymer (II-2).

Resin Synthesis Example 3

To a four-necked flask equipped with a stirrer, a thermometer and a reflux condenser, 2.9 parts of 1,4-dioxane was added. After heating it up to 72° C., a solution prepared by mixing 9.8 parts of Monomer (I-1), 0.15 part of 2,2'-azobisisobutyronitrile, 0.71 part of 2,2'-azobis(2,4-dimethylvaleronitrile) and 11.7 parts of 1,4-dioxane was added dropwise thereto over 2 hour. The resultant mixture was stirred for 5 hours at 72° C. The obtained reaction mixture was diluted with 10.7 parts of 1,4-dioxane and then, the resultant mixture was poured into 127 parts of heptane to cause precipitation. The precipitate was isolated and dissolved in propylene glycol monomethyl ether acetate. The obtained solution was concentrated to obtain 30 parts of a solution containing a polymer consisting of the structural unit represented by the following:

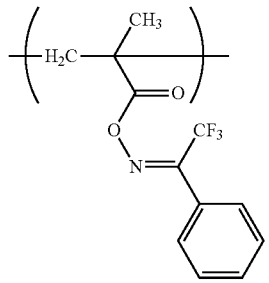

having a weight-average molecular weight (Mw) of $9.1 \times 10^3$ and a dispersion degree (Mw/Mn) of 2.2. The content of solid components in the solution was 32%. This polymer is called as Polymer (II-3).

Resin Synthesis Example 4

To a four-necked flask equipped with a stirrer, a thermometer and a reflux condenser, 3.7 parts of 1,4-dioxane was added. After heating it up to 72° C., a solution prepared by mixing 7.7 parts of Monomer (I-1), 4.6 parts of Monomer (L1), 0.20 part of 2,2'-azobisisobutyronitrile, 0.89 part of 2,2'-azobis(2,4-dimethylvaleronitrile) and 14.8 parts of 1,4-dioxane was added dropwise thereto over 2 hour. The resultant mixture was stirred for 5 hours at 72° C. The obtained reaction mixture was diluted with 13.5 parts of 1,4-dioxane and then, the resultant mixture was poured into 160 parts of heptane to cause precipitation. The precipitate was isolated and dissolved in propylene glycol monomethyl ether acetate. The obtained solution was concentrated to obtain 30 parts of a solution containing a polymer consisting of the structural units represented by the followings:

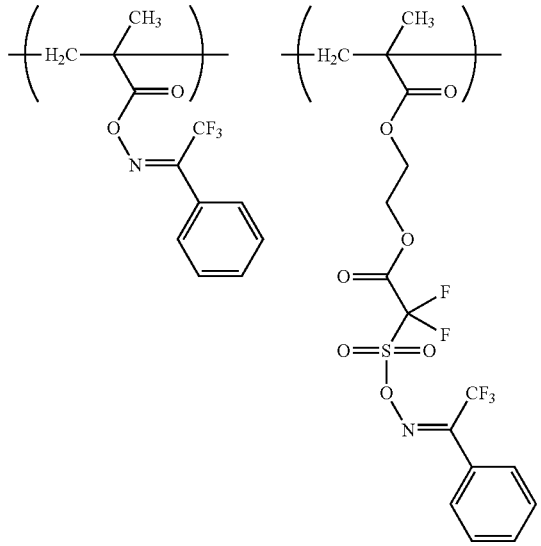

having a weight-average molecular weight (Mw) of 7.9×10³ and a dispersion degree (Mw/Mn) of 1.8. The content of solid components in the solution was 34%. This polymer is called as Polymer (II-4).

Resin Synthesis Example 5

To a four-necked flask equipped with a stirrer, a thermometer and a reflux condenser, 4.3 parts of 1,4-dioxane was added. After heating it up to 72° C., a solution prepared by mixing 5.1 parts of Monomer (I-1), 9.2 parts of Monomer (L1), 0.20 part of 2,2'-azobisisobutyronitrile, 0.89 part of 2,2'-azobis(2,4-dimethylvaleronitrile) and 17.2 parts of 1,4-dioxane was added dropwise thereto over 2 hour. The resultant mixture was stirred for 5 hours at 72° C. The obtained reaction mixture was diluted with 15.8 parts of 1,4-dioxane and then, the resultant mixture was poured into 186 parts of heptane to cause precipitation. The precipitate was isolated and dissolved in propylene glycol monomethyl ether acetate. The obtained solution was concentrated to obtain 30 parts of a solution containing a polymer consisting of the structural units represented by the followings:

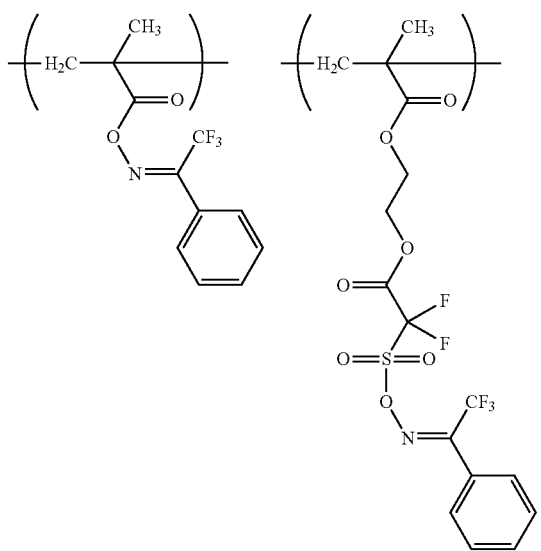

having a weight-average molecular weight (Mw) of 8.7×10³ and a dispersion degree (Mw/Mn) of 1.8. The content of solid components in the solution was 42%. This polymer is called as Polymer (II-5).

Resin Synthesis Example 6

To a four-necked flask equipped with a stirrer, a thermometer and a reflux condenser, 4.3 parts of 1,4-dioxane was added. After heating it up to 72° C., a solution prepared by mixing 2.3 parts of Monomer (I-1), 12.1 parts of Monomer (L1), 0.17 part of 2,2'-azobisisobutyronitrile, 0.78 part of 2,2'-azobis(2,4-dimethylvaleronitrile) and 17.2 parts of 1,4-dioxane was added dropwise thereto over 2 hour. The resultant mixture was stirred for 5 hours at 72° C. The obtained reaction mixture was diluted with 15.7 parts of 1,4-dioxane and then, the resultant mixture was poured into 186 parts of heptane to cause precipitation. The precipitate was isolated and dissolved in propylene glycol monomethyl ether acetate. The obtained solution was concentrated to obtain 30 parts of a solution containing a polymer consisting of the structural units represented by the followings:

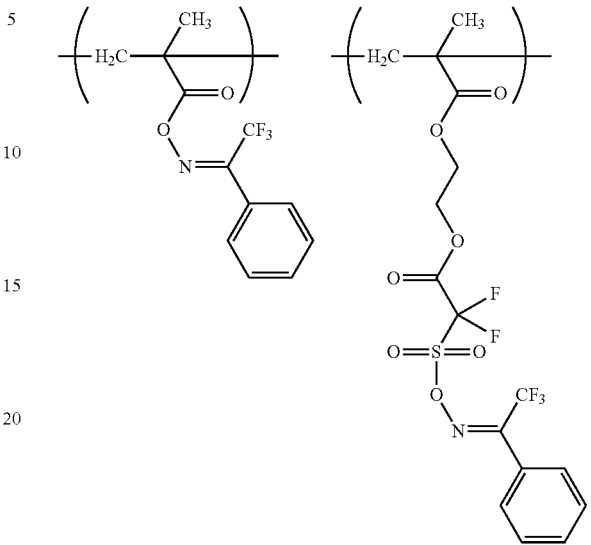

having a weight-average molecular weight (Mw) of 9.5×10³ and a dispersion degree (Mw/Mn) of 1.8. The content of solid components in the solution was 43%. This polymer is called as Polymer (II-6).

Resin Synthesis Example 7

To a four-necked flask equipped with a stirrer, a thermometer and a reflux condenser, 3.9 parts of 1,4-dioxane was added. After heating it up to 72° C., a solution prepared by mixing 7.7 parts of Monomer (I-1), 5.1 parts of Monomer (M-3), 0.30 part of 2,2'-azobisisobutyronitrile, 1.34 parts of 2,2'-azobis(2,4-dimethylvaleronitrile) and 15.4 parts of 1,4-dioxane was added dropwise thereto over 2 hour. The resultant mixture was stirred for 5 hours at 72° C. The obtained reaction mixture was diluted with 13.5 parts of 1,4-dioxane and then, the resultant mixture was poured into 167 parts of heptane to cause precipitation. The precipitate was isolated and dissolved in propylene glycol monomethyl ether acetate. The obtained solution was concentrated to obtain 30 parts of a solution containing a polymer consisting of the structural units represented by the followings:

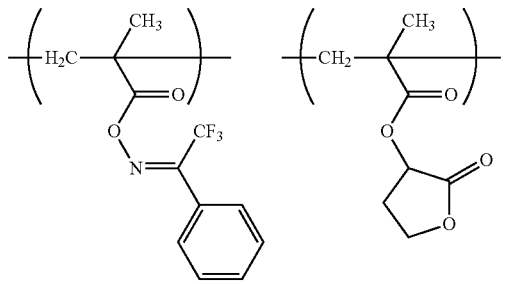

having a weight-average molecular weight (Mw) of 6.5×10³ and a dispersion degree (Mw/Mn) of 2.4. The content of solid components in the solution was 34%. This polymer is called as Polymer (II-7).

Resin Synthesis Example 8

To a four-necked flask equipped with a stirrer, a thermometer and a reflux condenser, 3.4 parts of 1,4-dioxane was added. After heating it up to 75° C., a solution prepared by mixing 5.1 parts of Monomer (I-1), 6.3 parts of Monomer (M-8), 0.20 part of 2,2'-azobisisobutyronitrile, 0.89 part of 2,2'-azobis(2,4-dimethylvaleronitrile) and 13.8 parts of 1,4-dioxane was added dropwise thereto over 2 hour. The resultant mixture was stirred for 5 hours at 75° C. The obtained reaction mixture was diluted with 13.5 parts of 1,4-dioxane and then, the resultant mixture was poured into 149 parts of heptane to cause precipitation. The precipitate was isolated and dissolved in propylene glycol monomethyl ether acetate. The obtained solution was concentrated to obtain 30 parts of a solution containing a polymer consisting of the structural units represented by the followings:

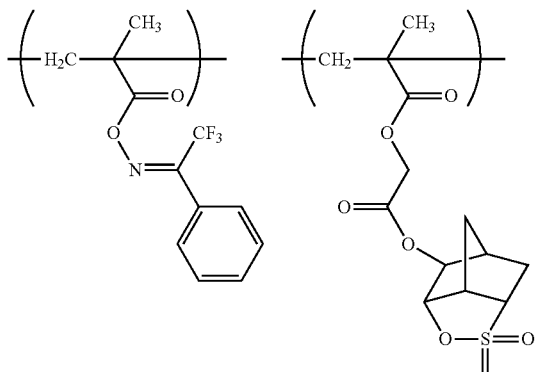

having a weight-average molecular weight (Mw) of $7.1 \times 10^3$ and a dispersion degree (Mw/Mn) of 1.9. The content of solid components in the solution was 34%. This polymer is called as Polymer (II-8).

Resin Synthesis Example 9

To a four-necked flask equipped with a stirrer, a thermometer and a reflux condenser, 4.8 parts of 1,4-dioxane was added. After heating it up to 72° C., a solution prepared by mixing 10.7 parts of Monomer (I-70), 5.1 parts of Monomer (M-3), 0.30 part of 2,2'-azobisisobutyronitrile, 1.34 parts of 2,2'-azobis(2,4-dimethylvaleronitrile) and 19.0 parts of 1,4-dioxane was added dropwise thereto over 2 hour. The resultant mixture was stirred for 5 hours at 72° C. The obtained reaction mixture was diluted with 16.6 parts of 1,4-dioxane and then, the resultant mixture was poured into 206 parts of heptane to cause precipitation. The precipitate was isolated and dissolved in propylene glycol monomethyl ether acetate. The obtained solution was concentrated to obtain 35 parts of a solution containing a polymer consisting of the structural units represented by the followings:

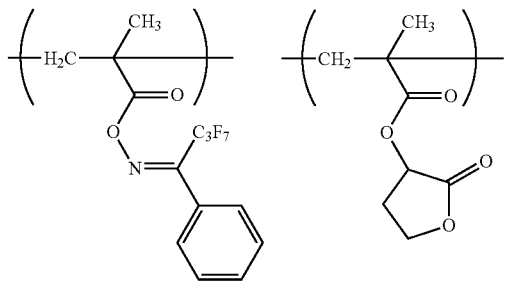

having a weight-average molecular weight (Mw) of $7.0 \times 10^3$ and a dispersion degree (Mw/Mn) of 2.4. The content of solid components in the solution was 35%. This polymer is called as Polymer (II-9).

Resin Synthesis Example 10

To a four-necked flask equipped with a stirrer, a thermometer and a reflux condenser, 1.9 parts of 1,4-dioxane was added. After heating it up to 72° C., a solution prepared by mixing 6.4 parts of Monomer (I-71), 0.04 part of 2,2'-azobisisobutyronitrile, 0.18 parts of 2,2'-azobis(2,4-dimethylvaleronitrile) and 7.7 parts of 1,4-dioxane was added dropwise thereto over 2 hour. The resultant mixture was stirred for 5 hours at 72° C. The obtained reaction mixture was diluted with 7.1 parts of 1,4-dioxane and then, the resultant mixture was poured into 83 parts of heptane to cause precipitation. The precipitate was isolated and dissolved in propylene glycol monomethyl ether acetate. The obtained solution was concentrated to obtain 20 parts of a solution containing a polymer consisting of the structural units represented by the followings:

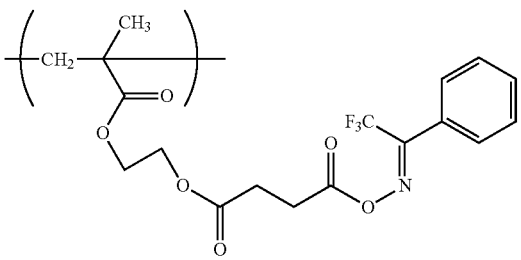

having a weight-average molecular weight (Mw) of $3.8 \times 10^4$ and a dispersion degree (Mw/Mn) of 3.2. The content of solid components in the solution was 25%. This polymer is called as Polymer (II-10).

Resin Synthesis Example 11

Monomer (M-4), Monomer (M-5), Monomer (M-2), Monomer (M-6), Monomer (M-3) and Monomer (I-2) were mixed in a molar ratio of 45/5/10/20/15/5 (Monomer (M-4)/Monomer (M-5)/Monomer (M-2)/Monomer (M-6)/Monomer (M-3)/Monomer (I-2)), and 1,4-dioxane of which amount was 1.5 times part based on total parts of all monomers was added to prepare a mixture. To the mixture, 2,2'-azobisisobutyronitrile as an initiator in a ratio of 1.05 mol % based on all monomer molar amount and 2,2'-azobis(2,4-dimethylvaleronitrile) as an initiator in a ratio of 3.15 mol % based on all monomer molar amount were added, and the obtained mixture was heated at 73° C. for about 5 hours. The reaction mixture obtained was poured into a large amount of a mixture of methanol and water (methanol/water=4/1) to cause precipitation. The precipitate was isolated and then washed three times with methanol. The precipitate was dried under reduced pressure to obtain a copolymer having a weight-average molecular weight of about $8.4 \times 10^3$ in a yield of 73%. The copolymer had the following structural units. This is called as Copolymer (III-1).

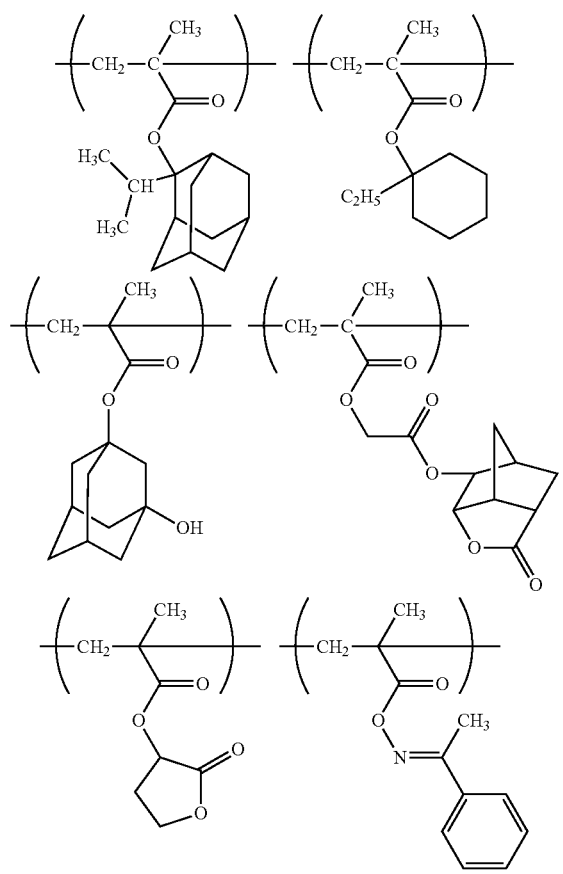

Resin Synthesis Example 12

Monomer (M-4), Monomer (M-5), Monomer (M-2) and Monomer (M-3) were mixed in a molar ratio of 35/10/11/44 (Monomer (M-4)/Monomer (M-5)/Monomer (M-2)/Monomer (M-3)), and 1,4-dioxane of which amount was 1.5 times part based on total parts of all monomers was added to prepare a mixture. To the mixture, 2,2'-azobisisobutyronitrile as an initiator in a ratio of 1 mol % based on all monomer molar amount and 2,2'-azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (methanol/water=4/1) to cause precipitation. The precipitate was isolated and then the operation wherein the precipitate was mixed with a large amount of a mixture of methanol and water followed by isolation of the precipitate was repeated three times for purification. As the result, a resin having a weight-average molecular weight of about 7,800 was obtained in a yield of 76%. The resin had the following structural units. This is called as Resin A1.

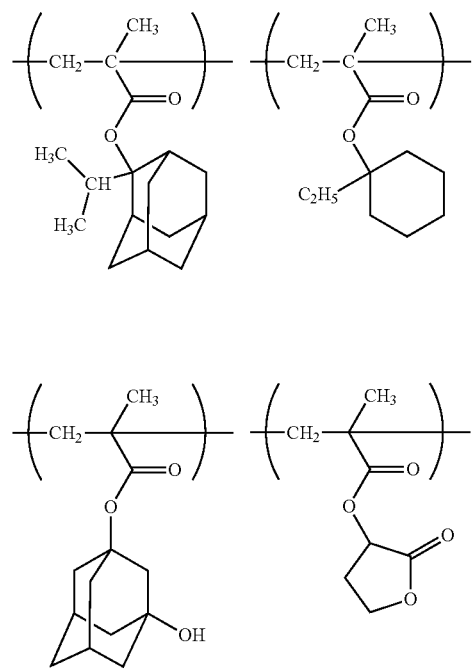

Resin Synthesis Example 13

Monomer (M-4), Monomer (M-5), Monomer (M-2), Monomer (M-6) and Monomer (M-3) were mixed in a molar ratio of 28/14/6/21/31 (Monomer (M-4)/Monomer (M-5)/ Monomer (M-2)/Monomer (M-6)/Monomer (M-3)), and 1,4-dioxane of which amount was 1.5 times part based on total parts of all monomers was added to prepare a mixture. To the mixture, 2,2'-azobisisobutyronitrile as an initiator in a ratio of 1 mol % based on all monomer molar amount and 2,2'-azobis (2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water (methanol/water=4/1) to cause precipitation. The precipitate was isolated and then the operation wherein the precipitate was mixed with a large amount of a mixture of methanol and water followed by isolation of the precipitate was repeated three times for purification. As the result, a resin having a weight-average molecular weight of about $8.9 \times 10^3$ in a yield of 72%. The resin had the following structural units. This is called as Resin A2.

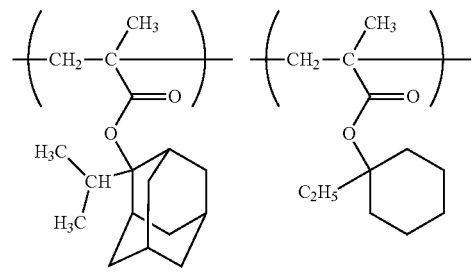

-continued

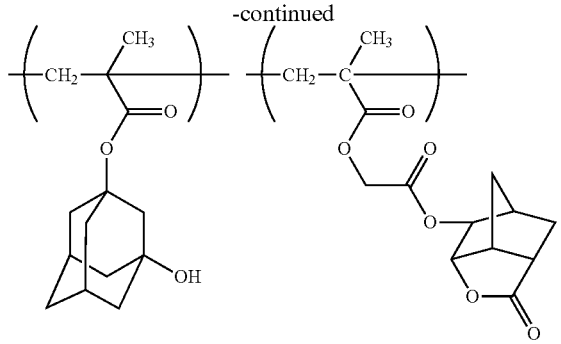

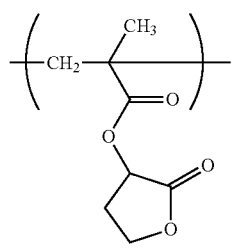

Resin Synthesis Example 14

Into a flask, 15.00 parts of Monomer (M-1), 4.89 parts of Monomer (M-2), 11.12 parts of Monomer (M-6) and 8.81 parts of Monomer (M-3) were added (molar ratio: 35/12/23/30 (Monomer (M-1)/Monomer (M-2)/Monomer (M-6)/Monomer (M-3)), and 1,4-dioxane of which amount was 1.5 times part based on total parts of all monomers was added thereto to prepare a solution. To the solution, 2,2'-azobisisobutyronitrile as an initiator in a ratio of 1 mol % based on all monomer molar amount and 2,2'-azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a large amount of a mixture of methanol and water to cause precipitation. The precipitate was isolated and then the operation wherein the precipitate was mixed with a large amount of a mixture of methanol and water followed by isolation of the precipitate was repeated three times for purification. As the result, a resin having a weight-average molecular weight of about $8.1 \times 10^3$ in a yield of 78%. The resin had the following structural units. This is called as Resin A3.

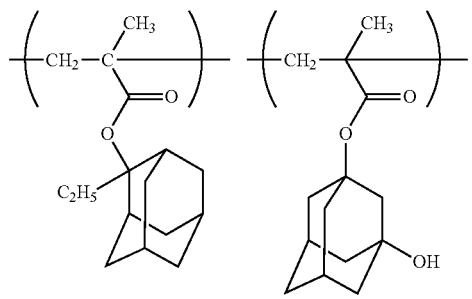

-continued

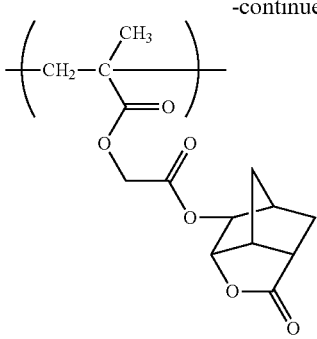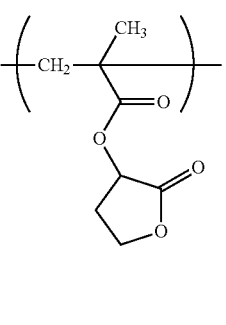

Examples 1 to 11 and Reference Example 1

Resin

Resin A1, A2, A3
Polymer (II-1), (II-3), (II-5), (II-6), (II-7), (II-8), (II-9), (II-10) Copolymer (III-1)
<Acid Generator>
B1:

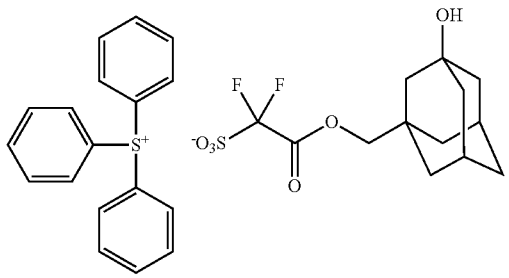

<Quencher>
C1: 2,6-diisopropylaniline
<Solvent>

| S1: propylene glycol monomethyl ether acetate | 220 parts |
| --- | --- |
| propylene glycol monomethyl ether | 20 parts |
| 2-heptanone | 20 parts |
| γ-butyrolactone | 3.5 parts |

The following components were mixed and dissolved, further, filtrated through a fluorine resin filter having pore diameter of 0.2 μm, to prepare photoresist compositions.
Resin (kind and amount are described in Table 5)
Acid generator (kind and amount are described in Table 5)
Quencher (kind and amount are described in Table 5)
Solvent S1

TABLE 5

| Ex. No. | Resin (kind/amount (part)) | Acid generator (kind/amount (part)) | Quencher (kind/amount (part)) | PB (° C.) | PEB (° C.) |
| --- | --- | --- | --- | --- | --- |
| Ex. 1 | A1/10 (II-1)/0.1 | B1/2.2 | C1/0.03 | 100 | 80 |
| Ex. 2 | A2/10 (II-1)/0.1 | B1/1.2 | C1/0.095 | 100 | 85 |

TABLE 5-continued

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 3 | A2/10 (II-6)/0.1 | B1/1.2 | C1/0.095 | 100 | 85 |
| Ex. 4 | A2/10 (II-7)/0.1 | B1/1.2 | C1/0.095 | 100 | 85 |
| Ex. 5 | A2/10 (II-8)/0.1 | B1/1.2 | C1/0.095 | 100 | 85 |
| Ex. 6 | A3/10 (II-6)/0.1 | B1/0.51 | C1/0.065 | 100 | 105 |
| Ex. 7 | A2/10 (II-3)/0.1 | B1/1.2 | C1/0.095 | 100 | 85 |
| Ex. 8 | A2/10 (II-5)/0.1 | B1/1.2 | C1/0.095 | 100 | 85 |
| Ex. 9 | A2/10 (II-9)/0.1 | B1/1.2 | C1/0.095 | 100 | 85 |
| Ex. 10 | A2/10 (II-10)/0.1 | B1/1.2 | C1/0.095 | 100 | 85 |
| Ex. 11 | (III-1)/10 | B1/1.2 | — | 100 | 85 |
| Ref. Ex. 1 | A3/10 | B1/0.51 | C1/0.065 | 100 | 105 |

Silicon wafers having a diameter of 12 inches were each coated with "ARC-29", which is an organic anti-reflective coating composition available from Nissan Chemical Industries, Ltd., and then baked under the conditions: 205° C., 60 seconds, to form a 780 Å-thick organic anti-reflective coating. Each of the photoresist compositions prepared as above was spin-coated over the anti-reflective coating so that the thickness of the resulting film became 75 nm after drying. The silicon wafers thus coated with the respective photoresist compositions were each prebaked on a direct hotplate at a temperature shown in column of "PB" of Table 5 for 60 seconds. Using an ArF excimer stepper ("XT-1900Gi" manufactured by ASML, NA=1.35, 3/4 Annular, X-Y deflection), each wafer thus formed with the respective photoresist film was subjected to line and space pattern immersion exposure, with the exposure quantity being varied stepwise.

After the exposure, each wafer was subjected to post-exposure baking on a hotplate at a temperature shown in column of "PEB" of Table 5 for 60 seconds and then to paddle development for 60 seconds with an aqueous solution of 2.38% tetramethylammonium hydroxide.

Each of line and space patterns developed on the organic anti-reflective coating substrate after the development was observed with a scanning electron microscope, the results of which are shown in Tables 6.

Effective Sensitivity (ES): It is expressed as the amount of exposure that the line pattern and the space pattern become 1:1 after exposure through 50 nm line and space pattern mask and development.

Line Width Roughness (LWR): The photoresist pattern was observed with a scanning electron microscope. The line widths of the line and space pattern at the exposure amount of ES were measured and the values of 3σ thereof were calculated based on the results of the measurement and shown in Table 6. The value of 3σ is one of index showing a variability of the line width, and the smaller the value of 3σ is, the better LWR is.

TABLE 6

| Ex. No. | LWR |
|---|---|
| Ex. 1 | 6.0 |
| Ex. 2 | 6.0 |
| Ex. 3 | 5.6 |

TABLE 6-continued

| Ex. No. | LWR |
|---|---|
| Ex. 4 | 6.0 |
| Ex. 5 | 5.8 |
| Ex. 6 | 8.2 |
| Ex. 7 | 6.0 |
| Ex. 8 | 5.8 |
| Ex. 9 | 6.0 |
| Ex. 10 | 6.0 |
| Ex. 11 | 5.9 |
| Ref. Ex. 1 | 9.1 |

The photoresist composition of the present invention provides a good photoresist pattern having good Line Width Roughness.

What is claimed is:

1. A photoresist composition comprising a polymer comprising a structural unit derived from a compound represented by the formula (I):

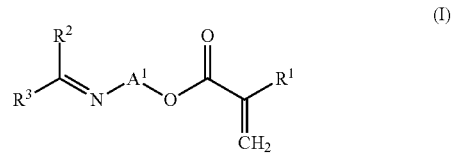

wherein $R^1$ represents a hydrogen atom or a methyl group, $R^2$ represents a phenyl group, $R^3$ represents a cyano group or a C1-C12 hydrocarbon group which can have one or more substituents and which can contain one or more heteroatoms, $A^1$ represents a single bond, —$(CH_2)_g$—CO—O—* or —$(CH_2)_h$—O—CO—$(CH_2)_i$—CO—O—* wherein g, h and i each independently represent an integer of 1 to 6 and * represents a binding position to the nitrogen atom, a resin having an acid-labile group and being insoluble or poorly soluble in an aqueous alkali solution but becoming soluble in an aqueous alkali solution by the action of an acid, and an acid generator.

2. The photoresist composition according to claim 1, wherein the resin comprises a structural unit derived from a monomer having an acid-labile group and at least one structural unit selected from the group consisting of a structural unit derived from an acrylate monomer having a hydroxyl-containing adamantyl group, a structural unit derived from a methacrylate monomer having a hydroxyl-containing adamantyl group, a structural unit derived from an acrylate monomer having a lactone ring and a structural unit derived from a methacrylate monomer having a lactone ring.

3. The photoresist composition according to claim 1, wherein the resin comprises a copolymer obtained by polymerizing at least a (meth)acrylate monomer having a hydroxyl-containing adamantyl group.

4. The photoresist composition according to claim 1, wherein the resin comprises a copolymer obtained by polymerizing at least a (meth)acrylate monomer having a lactone ring.

5. The photoresist composition according to claim 1, wherein the acid generator is a salt represented by the formula (B1):

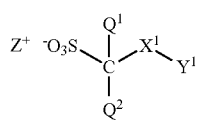

(B1)

wherein Q¹ and Q² each independently represent a fluorine atom or a C1-C6 perfluoroalkyl group, X¹ represents a single bond or a C1-C17 divalent saturated hydrocarbon group in which one or more —CH₂— can be replaced by —O— or —CO—, Y¹ represents a C1-C36 aliphatic hydrocarbon group which can have one or more substituents, a C3-C36 saturated cyclic hydrocarbon group which can have one or more substituents, or a C6-C36 aromatic hydrocarbon group which can have one or more substituents, and one or more —CH₂— in the aliphatic hydrocarbon group and the saturated cyclic hydrocarbon group can be replaced by —O— or —CO—, and Z⁺ represents an organic counter cation.

6. A process for producing a photoresist pattern comprising the following steps (1) to (5):
(1) a step of applying the photoresist composition according to claim 1 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

7. A compound represented by the formula (I-A):

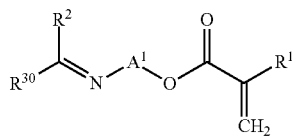

(I-A)

wherein R¹ represents a hydrogen atom or a methyl group, R² represents a C6-C12 aromatic hydrocarbon group which can have one or more substituents, R³⁰ represents a C1-C4 fluorinated alkyl group, A¹ represents a single bond, —(CH₂)_g—CO—O—* or —(CH₂)_h—O—CO—(CH₂)_i—CO—O—* wherein g, h and i each independently represent an integer of 1 to 6 and * represents a binding position to the nitrogen atom.

8. A polymer comprising a structural unit derived from a compound represented by the formula (I-A):

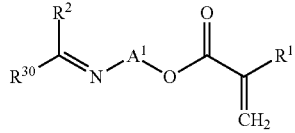

(I-A)

wherein R¹ represents a hydrogen atom or a methyl group, R² represents a C6-C12 aromatic hydrocarbon group which can have one or more substituents, R³⁰ represents a C1-C4 fluorinated alkyl group, A¹ represents a single bond, —(CH₂)_g—CO—O—* or —(CH₂)_h—O—CO—(CH₂)_i—CO—O—* wherein g, h and i each independently represent an integer of 1 to 6 and * represents a binding position to the nitrogen atom.

9. A photoresist composition comprising a copolymer comprising a structural unit derived from a compound represented by the formula (I):

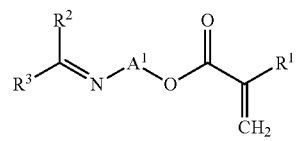

(I)

wherein R¹ represents a hydrogen atom or a methyl group, R² represents a phenyl group, R³ represents a cyano group or a C1-C12 hydrocarbon group which can have one or more substituents and which can contain one or more heteroatoms, A¹ represents a single bond, —(CH₂)_g—CO—O—* or —(CH₂)_h—O—CO—(CH₂)_i—CO—O—* wherein g, h and i each independently represent an integer of 1 to 6 and * represents a binding position to the nitrogen atom, and a structural unit having an acid-labile group, and being insoluble or poorly soluble in an aqueous alkali solution but becoming soluble in an aqueous alkali solution by the action of an acid, and
an acid generator.

10. The photoresist composition according to claim 9, wherein the copolymer further comprises at least one structural unit selected from the group consisting of a structural unit derived from an acrylate monomer having a hydroxyl-containing adamantyl group, a structural unit derived from a methacrylate monomer having a hydroxyl-containing adamantyl group, a structural unit derived from an acrylate monomer having a lactone ring and a structural unit derived from a methacrylate monomer having a lactone ring.

11. The photoresist composition according to claim 9, wherein the acid generator is a salt represented by the formula (B1):

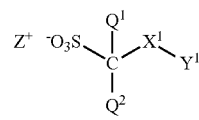

(B1)

wherein Q¹ and Q² each independently represent a fluorine atom or a C1-C6 perfluoroalkyl group, X¹ represents a single bond or a C1-C17 divalent saturated hydrocarbon group in which one or more —CH₂— can be replaced by —O— or —CO—, Y¹ represents a C1-C36 aliphatic hydrocarbon group which can have one or more substituents, a C3-C36 saturated cyclic hydrocarbon group which can have one or more substituents, or a C6-C36 aromatic hydrocarbon group which can have one or more substituents, and one or more —CH₂— in the aliphatic hydrocarbon group and the saturated cyclic hydrocarbon group can be replaced by —O— or —CO—, and Z⁺ represents an organic counter cation.

12. A process for producing a photoresist pattern comprising the following steps (1) to (5):
(1) a step of applying the photoresist composition according to claim 9 on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

* * * * *